(12) United States Patent
Matsumoto et al.

(10) Patent No.: US 7,268,145 B2
(45) Date of Patent: Sep. 11, 2007

(54) THIOBENZIMIDAZOLE DERIVATIVES

(75) Inventors: Yoshiyuki Matsumoto, Hino (JP); Susumu Takeuchi, Hino (JP); Naoki Hase, Hino (JP)

(73) Assignee: Teijin Pharma Limited, Tokyo (JP)

( * ) Notice: Subject to any disclaimer, the term of this patent is extended or adjusted under 35 U.S.C. 154(b) by 481 days.

(21) Appl. No.: 10/963,710

(22) Filed: Oct. 14, 2004

(65) Prior Publication Data
US 2006/0040976 A1 Feb. 23, 2006

Related U.S. Application Data

(63) Continuation of application No. 09/743,483, filed as application No. PCT/JP99/03799 on Jul. 14, 1999, now abandoned.

(30) Foreign Application Priority Data

Jul. 15, 1998 (JP) .................. 10-200250

(51) Int. Cl.
A01N 43/42 (2006.01)
A01N 43/52 (2006.01)
A61K 31/44 (2006.01)
A61K 31/415 (2006.01)
C07D 513/02 (2006.01)

(52) U.S. Cl. .................. 514/303; 514/394; 546/118; 548/307.1; 544/298; 544/269

(58) Field of Classification Search ............ 546/118; 548/307.1; 514/303, 394, 269; 544/298
See application file for complete search history.

(56) References Cited

U.S. PATENT DOCUMENTS

| | | | |
|---|---|---|---|
| 5,021,443 A | 6/1991 | Bru-Magneez et al. |
| 5,124,336 A | 6/1992 | Bru-Magneez et al. |
| 5,128,327 A | 7/1992 | Chakravarty et al. |
| 5,128,339 A | 7/1992 | Dunlap et al. |
| 5,128,359 A | 7/1992 | Bru-Magniez et al. |
| 5,191,086 A | 3/1993 | Poss |
| 5,374,615 A | 12/1994 | Poss |
| 5,444,068 A | 8/1995 | Heitsch et al. |
| 5,449,682 A | 9/1995 | Greenlee et al. |
| 5,468,764 A | 11/1995 | Heitsch et al. |
| 5,635,525 A | 6/1997 | Heitsch et al. |
| 5,691,335 A | 11/1997 | Fukmai et al. |
| 5,814,631 A | 9/1998 | Fukmai et al. |
| 5,948,785 A | 9/1999 | Akahoshi et al. |
| 6,080,738 A | 6/2000 | Akahoshi et al. |

FOREIGN PATENT DOCUMENTS

| | | |
|---|---|---|
| AT | 389 107 B | 10/1989 |
| CA | 2336909 A1 | 1/2000 |
| EP | 0 251 536 A1 | 1/1987 |
| EP | 0 292 051 A2 | 11/1988 |
| EP | 0 398 600 A2 | 11/1990 |
| EP | 0 400 974 A2 | 12/1990 |
| EP | 0442 8201 A1 | 8/1991 |
| EP | 0 501 269 A1 | 9/1992 |
| EP | 0533058 A1 | 3/1993 |
| EP | 0721944 A1 | 7/1996 |
| EP | 0795548 A1 | 9/1997 |
| EP | 0826671 A1 | 3/1998 |
| EP | 0 849 259 A1 | 6/1998 |
| EP | 1097926 A1 | 5/2001 |
| FR | 2430950 A1 | 2/1980 |
| HU | 213266 | 12/1991 |
| JP | 62-212386 | 9/1987 |
| JP | 1-265089 | 10/1989 |
| JP | 03014566 A | 1/1991 |
| JP | 5-112559 * | 5/1993 |
| JP | 5-112559 A2 | 5/1993 |
| JP | 5-155858 | 6/1993 |

(Continued)

OTHER PUBLICATIONS

Seki et al., "2-Benzimidazolethiol derivatives. I. Synthesis and analgesic effects", (Yakugaku Zasshi, vol. 82, 1962, pp. 1620-1624)
Chemical Abstracts, vol. 59, No. 2, 1963 Columbus, OH US; column 1616; XP002210546.

(Continued)

Primary Examiner—Margaret D. Seaman
Assistant Examiner—Niloofar Rahmani
(74) Attorney, Agent, or Firm—Sughrue Mion, PLLC

(57) ABSTRACT

The present invention is a thiobenzimidazole derivative represented by the following formula (1)

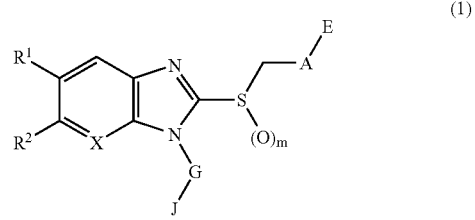

or a medically acceptable salt thereof wherein said thiobenzimidazole derivative and a medically acceptable salt thereof have a potent activity of inhibiting human chymase. Thus, they are potential preventive and/or therapeutic agents clinically applicable to various diseases in which human chymase is involved.

13 Claims, No Drawings

FOREIGN PATENT DOCUMENTS

| | | | |
|---|---|---|---|
| JP | 08 020 584 A | 1/1996 |
| JP | 08208654 A | 8/1996 |
| JP | 09031061 A | 2/1997 |
| WO | 96/04248 A1 | 2/1996 |
| WO | 9711941 A1 | 4/1997 |
| WO | WO98/08818 A1 | 3/1998 |
| WO | 9926932 A1 | 6/1999 |
| WO | WO99/57103 A1 | 11/1999 |
| WO | 0003997 A1 | 1/2000 |
| WO | 0100615 A1 | 1/2001 |
| WO | 9633974 A1 | 10/2006 |

OTHER PUBLICATIONS

Anan Eva et al. "Cyclic thioamides in nucleophilic addition reactions II" (UZB. Khim Zh., vol. 17, No. 5, 1973 pp. 56-59) Chemical Abstracts vol. 80, No. 9, 1974, Columbus, OH US; abstract No. 47905r, p. 356; XP002210547.

Nicolai, Eric, et al., "Synthesis and Structure-Acticity Relationships of Novel Benzimidazole and Imidazo[4,5-*b*] pyridine Acid Derivatives as Thromboxane $A_2$ Receptor Antagonists" J. Med. Chem., 1993 vol. 36, p. 1175-1187 XP002926392.

European Search Report.

Hungarian Patent Office Novelty Search Report.

Nakayama et al. Nipon rinsho. Japanese Journal of Clinical Medicine, 1997, 55(8): 1903-8.

Saarinen et al. Allergy, 2001, 56(1):58-64.

Journal of Med. Chem. 36(9( 1175-87 (1993).

Chemical Abstracts, vol. 85. 172661 (1976).

Ahsan Husain, "The Chymase—angiotensin system in humans,"Journal of Hypertension, Current Science, Nov. 11, 1993, pp. 1155-1159, vol. 11, No. 11, US.

H. Urata, et al., "Cardiac angiotensin II formation: the agniotensin—I converting enzyme and human chymase", European Heart Journal, The European Society of Cardiology, 1993, pp. 177-182, vol. 14, Supplement J, Europe.

H. Fukami, et al., Chymase: Its Pathophysiological Roles and Inhibitors, : Current Pharmaceutical Design, 1998, pp. 439-453. vol. 4, No. 6, Bentham Science Publishers, Netherlands.

Yoshida et al., CA 115: 71600, 1991.

Golub et al., Science, vol. 286, Oct. 15, 1999, pp. 531-537.

Screening Collection abstract, catalog published Mar. 28, 2000, CAS Registry No. 309281-42-3.

Screening Collection abstract, catalog published Mar. 28, 2000, CAS Registry No. 309281-37-6.

Screening Collection abstract, catalog published Mar. 28, 2000, CAS Registry No. 312505-00-3.

Peekdale Fine Chemicals Product List, catalog published Jul. 7, 2000, CAS Registry No. 392233-94-2.

\* cited by examiner

THIOBENZIMIDAZOLE DERIVATIVES

This is a continuation of Application No. 09/743,483 filed Jan. 10, 2001, now abandoned which is a National Stage of International Application No. PCT/JP99/03799, filed Jul. 14, 1999.

TECHNICAL FIELD

The present invention relates to thiobenzimidazole derivatives represented by the formula (1) and, more specifically, thiobenzimidazole derivatives useful as inhibitors of human chymase activity.

BACKGROUND ART

Chymase is one of the neutral proteases present in mast cell granules, and is deeply involved in a variety of biological processes in which mast cells participate. Various effects have been reported including, for example, the promotion of degranulation from mast cells, the activation of interleukin-1β (IL-1β), the activation of matrix protease, the decomposition of fibronectin and type IV collagen, the promotion of the release of transforming growth factor-β (TGF-β), the activation of substance P and vasoactive intestinal polypeptide (VIP), the conversion of angiotensin I (Ang I) to Ang II, the conversion of endothelin, and the like.

The above indicates that inhibitors of said chymase activity may be promising as preventive and/or therapeutic agents for diseases of respiratory organs such as bronchial asthma, inflammatory/allergic diseases, for example allergic rhinitis, atopic dermatitis, and urticaria; diseases of circulatory organs, for example. sclerosing vascular lesions, intravascular stenosis, disturbances of peripheral circulation, renal failure, and cardiac failure; diseases of bone/cartilage metabolism such as rheumatoid arthritis and osteoarthritis, and the like.

As inhibitors of chymase activity, there are known triazine derivatives (Japanese Unexamined Patent Publication (Kokai) No. 8-208654); hydantoin derivatives (Japanese Unexamined Patent Publication (Kokai) No. 9-31061); imidazolidine derivatives (PCT Application WO 96/04248); quinazoline derivatives (PCT Application Wo 97/11941); heterocyclic amide derivatives (PCT Application WO 96/33974); and the like. However, the structures of these compounds are entirely different from those of the compounds of the present invention.

On the other hand, an art related to the compounds of the present invention is disclosed in U.S. Pat. No. 5,124,336. Said specification describes thiobenzimidazole derivatives as having an activity of antagonizing thromboxane receptor. The specification, however, makes no mention of the activity of said compounds to inhibit human chymase.

Thus, it is an object of the present invention to provide novel compounds that are potential and clinically applicable inhibitors of human chymase.

DISCLOSURE OF THE INVENTION

Thus, after intensive research to attain the above objective, the applicants of the present invention have found the following 1 to 15 and have thereby completed the present invention.

1. A thiobenzimidazole derivative represented by the following formula (1):

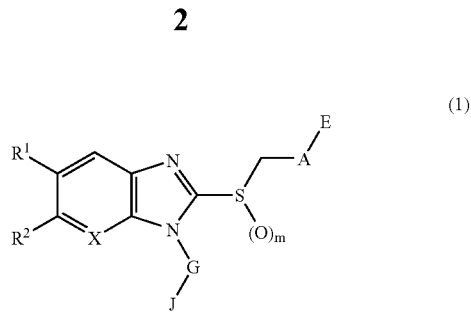

wherein, $R^1$ and $R^2$, simultaneously or independently of each other, represent a hydrogen atom, a halogen atom, a trihalomethyl group, a cyano group, a hydroxy group, an alkyl group having 1 to 4 carbons or an alkoxy group having 1 to 4 carbons, or $R^1$ and $R^2$ together form —O—CH$_2$—O—, —O—CH$_2$—CH$_2$—O— or —CH$_2$—CH$_2$—CH$_2$—, in which the carbons may be substituted with one or a plurality of alkyl groups having 1 to 4 carbons;

A represents a single bond, a substituted or unsubstituted, linear or branched alkylene group having 1 to 6 carbons, a substituted or unsubstituted arylene group having 6 to 11 carbons, or a substituted or unsubstituted heteroarylene group having 4 to 10 carbons that may contain one or a plurality of oxygen, nitrogen and sulfur atoms on the ring, in which the substituent represents a halogen atom, OH, NO$_2$, CN, a linear or branched alkyl group having 1 to 6 carbons, a linear or branched alkoxy group having 1 to 6 carbons (the substituents may be joined to each other at adjacent sites via an acetal bond), a linear or branched alkylthio group having 1 to 6 carbons, a linear or branched alkylsulfonyl group having 1 to 6 carbons, a linear or branched acyl group having 1 to 6 carbons, a linear or branched acylamino group having 1 to 6 carbons, a trihalomethyl group, a trihalomethoxy group, a phenyl group, an oxo group, or a phenoxy group that may be substituted with one or more halogen atoms, and in which the substituents may be independently substituted at any one or more sites of the ring or the alkylene group;

E represents COOR$^3$, SO$_3$R$^3$, CONHR$^3$, SO$_2$NHR$^3$, a tetrazole group, a 5-oxo-1,2,4-oxadiazole group or a 5-oxo-1,2,4-thiadiazole group in which R$^3$ represents a hydrogen atom, or a linear or branched alkyl group having 1 to 6 carbons;

G represents a substituted or unsubstituted, linear or branched alkylene group having 1-6 carbons that may be interrupted with one or a plurality of O, S, SO$_2$, and NR$^3$, in which R$^3$ is as defined above and the substituent represents a halogen atom, OH, NO$_2$, CN, a linear or branched alkyl group having 1 to 6 carbons, a linear or branched alkoxy group having 1 to 6 carbons (the substituents may be joined to each other at adjacent sites via an acetal bond), a trihalomethyl group, a trihalomethoxy group, a phenyl group, or an oxo group;

m represents an integer of 0 to 2;

when m is 0 and A is a substituted or unsubstituted, linear or branched alkylene group having 1 to 6 carbons, then J represents a substituted or unsubstituted, linear, cyclic or branched alkyl group having 3 to 6 carbons, a substituted or unsubstituted aryl group having 7 to 9 carbons, a substituted aryl group having 10 to 11 carbons, a substituted or unsubstituted heteroaryl group (excluding unsubstituted pyridyl groups) having 4 to 10 carbons that may contain one or a plurality of oxygen, nitrogen and sulfur atoms on the ring;

when m is 0 and A is a substituted or unsubstituted arylene group having 6 to 11 carbons or a substituted or unsubstituted heteroarylene group having 4 to 10 carbons that may contain one or a plurality of oxygen, nitrogen and sulfur atoms on the ring, then J represents a substituted or unsubstituted, linear, cyclic or branched alkyl group having 1 to 6 carbons, a substituted or unsubstituted aryl group having 6 to 11 carbons, or a substituted or unsubstituted heteroaryl group (excluding unsubstituted pyndyl groups) having 4 to 10 carbons that may contain one or a plurality of oxygen, nitrogen and sulfur atoms on the ring; or when m is 0 and A is a single bond or when m is 1 or 2, then J represents a substituted or unsubstituted, linear, cyclic or branched alkyl group having 1 to 6 carbons, a substituted or unsubstituted aryl group having 6 to 11 carbons, or a substituted or unsubstituted heteroaryl group (excluding unsubstituted pyridyl groups) having 4 to 10 carbons that may contain one or a plurality of oxygen, nitrogen and sulfur atoms on the ring, in which the substituent represents a halogen atom, OH, $NO_2$, CN, a linear or branched alkyl group having 1 to 6 carbons, a linear or branched alkoxy group having 1 to 6 carbons (the substituents may be joined to each other at adjacent sites via an acetal bond), a linear or branched alkylthio group having 1 to 6 carbons, a linear or branched alkylsulfonyl group having 1 to 6 carbons, a linear or branched acyl group having 1 to 6 carbons, a linear or branched acylamino group having 1 to 6 carbons, a substituted or unsubstituted anilide group, a trihalomethyl group, a trihalomethoxy group, a phenyl group, an oxo group, a $COOR^3$ group, or a phenoxy group that may be substituted with one or more halogen atoms, and in which the substituents may be independently substituted at any one or more sites of the ring or the alkylene group; and X represents CH or a nitrogen atom;

or a medically acceptable salt thereof (hereinafter referred to as "the thiobenzimidazole derivative of the present invention").

2. The thiobenzimidazole derivative characterized in that, in the above formula (1), A is a substituted or unsubstituted, linear or branched alkylene group having 1 to 6 carbons, a substituted or unsubstituted arylene group having 6 to 11 carbons, or a substituted or unsubstituted heteroarylene group having 4 to 10 carbons that may contain one or a plurality of oxygen, nitrogen and sulfur atoms on the ring, or a medically acceptable salt thereof.

3. The thiobenzimidazole derivative characterized in that, in the above formula (1), A is a substituted or unsubstituted heteroarylene group having 4 to 10 carbons that may contain one or a plurality of oxygen, nitrogen and sulfur atoms on the ring, or a medically acceptable salt thereof.

4. The thiobenzimidazole derivative characterized in that, in the above formula (1), m is 1, or a medically acceptable salt thereof.

5. The thiobenzimidazole derivative characterized in that, in the above formula (1), m is 2, or a medically acceptable salt thereof.

6. The thiobenzimidazole derivative characterized in that, in the above formula (1), m is 0, A is a substituted or unsubstituted, linear or branched alkylene group having 1 to 6 carbons, and J is a substituted or unsubstituted aryl group having 7 to 9 carbons, a substituted aryl group having 10 to 11 carbons, or a substituted or unsubstituted heteroaryl group having 4 to 10 carbons that may contain one or a plurality of oxygen, nitrogen and sulfur atoms on the ring, or a medically acceptable salt thereof.

7. The thiobenzimidazole derivative characterized in that, in the above formula (1), m is 0, A is a substituted or unsubstituted arylene group having 6 to 11 carbons or a substituted or unsubstituted heteroarylene group having 4 to 10 carbons that may contain one or a plurality of oxygen, nitrogen and sulfur atoms on the ring, and J is a substituted or unsubstituted aryl group having 6 to 11 carbons or a substituted or unsubstituted heteroaryl group having 4 to 10 carbons that may contain one or a plurality of oxygen, nitrogen and sulfur atoms on the ring, or a medically acceptable salt thereof.

8. The thiobenzimidazole derivative characterized in that, in the above formula (1), G is —$CH_2$—, —$CH_2$—$CH_2$—, —$CH_2CO$—, —$CH_2CH_2O$—, —$CH_2CONH$—, —CO—, —$SO_2$—, —$CH_2SO_2$—, —$CH_2S$—or —$CH_2CH_2S$—, or a medically acceptable salt thereof.

9. The thiobenzimidazole derivative characterized in that, in the above formula (1), $R^1$ and $R^2$ simultaneously represent a hydrogen atom, a halogen atom, an alkyl group having 1 to 4 carbons or an alkoxy group having 1 to 4 carbons, or $R^1$ and $R^2$, independently of each other, represent a hydrogen atom, a halogen atom, an alkyl group having 1 to 4 carbons, an alkoxy group having 1 to 4 carbons, a trihalomethyl group, a cyano group, or a hydroxy group, or a medically acceptable salt thereof.

10. The thiobenzimidazole derivative characterized in that, in the above formula (1), E represents COOH or a tetrazole group, or a medically acceptable salt thereof.

11. The thiobenzimidazole derivative characterized in that, in the above formula (1), X represents CH, or a medically acceptable salt thereof.

12. A thiobenzimidazole derivative characterized by having an activity of inhibiting human chymase, or a medically acceptable salt thereof.

13. A pharmaceutical composition comprising an at least one thiobenzimidazole derivative or a medically acceptable salt thereof and a pharmaceutically acceptable carrier.

14. A pharmaceutical composition which is a preventive and/or therapeutic agent for a disease.

15. A preventive and/or therapeutic agent wherein said disease is an inflammatory disease, an allergic disease, a disease of respiratory organs, a disease of circulatory organs, or a disease of bone/cartilage metabolism.

BEST MODE FOR CARRYING OUT THE INVENTION

The present invention will now be explained in more detail below.

The above definitions concerning the substituents of the compounds of formula (1) of the present invention are as follows:

$R^1$ and $R^2$, simultaneously or independently of each other, represent a hydrogen atom, a halogen atom, a trihalomethyl group, a cyano group, a hydroxy group, an alkyl group having 1 to 4 carbons or an alkoxy group having 1 to 4 carbons, or $R^1$ and $R^2$ together form —O—$CH_2$—O—, —O—$CH_2$—$CH_2$—O— or —$CH_2$—$CH_2$—$CH_2$—, in which the carbons may be substituted with one or a plurality of alkyl groups having 1 to 4 carbons. As the alkyl group having 1 to 4 carbons, there can be mentioned a methyl group, an ethyl group, a (n, i-) propyl group and a (n, i, s, t-) butyl group, and preferably a methyl group may be mentioned. Preferably $R^1$ and $R^2$ simultaneously represent a hydrogen atom, a halogen atom, an alkyl group having 1 to 4 carbons or an alkoxy group having 1 to 4 carbons, or $R^1$ and $R^2$, independently of each other, represent a hydrogen atom, a halogen atom, a trihalomethyl group, a cyano group, a hydroxy group, an alkyl group having 1 to 4 carbons, or an alkoxy group having 1 to 4 carbons. As the halogen atom, as used herein, there can be mentioned a fluorine atom, a chlorine atom, a bromine atom and the like, and preferably a chlorine atom and a fluorine atom may be mentioned. As the alkyl group having 1 to 4 carbons, there can be mentioned a methyl group, an ethyl group, a (n, i-) propyl group and a (n, i, t-) butyl group, and preferably a methyl group may be mentioned. As the alkoxy group having 1 to 4 carbons, there can be mentioned a methoxy group, an ethoxy group, a (n, i-) propyloxy group and a (n, i, s, t-) butyloxy group, and preferably a methoxy group may be mentioned.

A represents a single bond, a substituted or unsubstituted, linear or branched alkylene group having 1 to 6 carbons, a substituted or unsubstituted arylene group having 6 to 11 carbons, or a substituted or unsubstituted heteroarylene group having 4 to 10 carbons that may contain one or a plurality of oxygen, nitrogen and sulfur atoms on the ring. Preferably, there can be mentioned a substituted or unsubstituted, linear or branched alkylene group having 1 to 6 carbons, a substituted or unsubstituted arylene group having 6 to 11 carbons, or a substituted or unsubstituted heteroarylene group having 4 to 10 carbons that may contain one or a plurality of oxygen, nitrogen and sulfur atoms on the ring. As the substituted or unsubstituted, linear or branched alkylene group having 1 to 6 carbons, there can be mentioned a methylene group, an ethylene group, a (n, i-) propylene group and a (n, i, t-) butylene group, and preferably an ethylene group may be mentioned. As the substituted or unsubstituted arylene group having 6 to 11 carbons, there can be mention ed a phenylene group, an indenylene group and a naphthylene group etc., and preferably a phenylene group may be mentioned. As the substituted or unsubstituted heteroarylene group having 4 to 10 carbons that may contain one or a plurality of oxygen, nitrogen and sulfur atoms on the ring, there can be mentioned a pyridilene group, a furanylene group, a thiophenylene group, an imidazolene group, a thiazolene group, a pyrimidilene group, an oxazolene group, an isoxazolene group, a benzphenylene group, a benzimidazolene group, a quinolilene group, an indolene group, a benzothiazolene group and the like, and preferably a pyridilene group, a furanylene group, and a thiophenylene group may be mentioned.

Furthermore, as the substituent, as used herein, there can be mentioned a halogen atom, OH, $NO_2$, CN, a linear or branched alkyl group having 1 to 6 carbons, a linear or branched alkoxy group having 1 to 6 carbons in which the substituent may be joined to each other at adjacent sites via an acetal bond, a linear or branched alkylthio group having 1 to 6 carbons, a linear or branched alkylsulfonyl group having 1 to 6 carbons, a linear or branched acyl group having 1 to 6 carbons, a linear or branched acylamino group having 1 to 6 carbons, a trihalomethyl group, a trihalomethoxy group, a phenyl group, or a phenoxy group that may be substituted with one or more halogen atoms. They may be independently substituted at any one or more sites of the ring or the alkylene group. Specifically, there can be mentioned OH, a chloro group, a bromo group, a nitro group, a methoxy group, a cyano group, a methylenedioxy group, a trifluoromethyl group, a methyl group, an ethyl group, a (n, i-) propyl group, a (n, i, t-) butyl group, and the like.

As E, there can be mentioned $COOR^3$, $SO_3R^3$, $CONHR^3$, $SO_2NHR^3$, a tetrazole group, a 5-oxo-1,2,4-oxadiazole group or a 5-oxo-1,2,4-thiadiazole group, and preferably $COOR^3$ or a tetrazole group may be mentioned. As $R^3$ as used herein, there can be mentioned a hydrogen atom or a linear or branched alkyl group having 1 to 6 carbons, and preferably a hydrogen atom, a methyl group, an ethyl group, or a t-butyl group may be mentioned, and most preferably a hydrogen atom may be mentioned.

G represents a substituted or unsubstituted, linear or branched alkyl group having 1 to 6 carbons that may be interrupted with one or a plurality of O, S, $SO_2$, and $NR^3$, in which $R^3$ is as defined above and the substituent represents a halogen atom, OH, $NO_2$, CN, a linear or branched alkyl group having 1 to 6 carbons, a linear or branched alkoxy group having 1 to 6 carbons (the substituents may be joined to each other at adjacent sites via an acetal bond), a trihalomethyl group, a trihalomethoxy group, a phenyl group, or an oxo group. Specifically, there can be mentioned —$CH_2$—, —$CH_2CH_2$—, —$CH_2CO$—, —$CH_2CH_2O$—, $CH_2CONH$—, —CO—, —$SO_2$—, —$CH_2SO_2$—, —$CH_2S$—, —$CH_2CH_2S$— and the like, and preferably —$CH_2$—, —$CH_2CH_2$—, —$CH_2CO$— or —$CH_2CH_2O$— may be mentioned.

m represents an integer of 0 to 2, and preferably 0 or 2 may be mentioned.

When m is 0 and A is a substituted or unsubstituted, linear or branched alkylene group having 1 to 6 carbons, then J represents a substituted or unsubstituted, linear, cyclic or branched alkyl group having 3 to 6 carbons, a substituted or unsubstituted aryl group having 7 to 9 carbons, a substituted aryl group having 10 to 11 carbons, a substituted or unsubstituted heteroaryl group (excluding unsubstituted pyridyl groups) having 4 to 10 carbons that may contain one or a plurality of oxygen, nitrogen and sulfur atoms on the ring. Preferably, a substituted aryl group having 10 to 11 carbons and a substituted or unsubstituted heteroaryl group having 4 to 10 carbons that may contain one or a plurality of oxygen, nitrogen and sulfur atoms on the ring may be mentioned. As the substituted or unsubstituted, linear, cyclic or branched alkyl group having 1 to 6 carbons, there can be mentioned a (n, i-) propyl group, a (n, i, s, t-) butyl group, a (n, i, ne, t-) pentyl group and a cyclohexyl group. As the substituted or unsubstituted aryl group having 7 to 9 carbons, there can be mentioned an indenyl group, and as the substituted aryl group having 10 to 11 carbons, there can be mentioned a naphthyl group. As the substituted or unsubstituted heteroaryl group having 4 to 10 carbons that may contain one or a plurality of oxygen, nitrogen and sulfur atoms on the ring, there can be mentioned a pyridyl group, a furanyl group, a thiophenyl group, an imidazole group, a thiazole group, a pyrimidine group, an oxazole group, an isoxazole group, a benzofurane group, a benzimidazole group, a quinoline group, an isoquinoline group, a quinoxaline group, a benzoxadiazole group, a benzothiadiazole group, an indole group, a N-methylindole group, a benzothiazole group, a benzothiophenyl group, a benzisoxazole group and the like, and preferably a benzothiophenyl group or a N-methylindole group may be mentioned.

When m is 0 and A is a substituted or unsubstituted arylene group having 6 to 11 carbons or a substituted or unsubstituted heteroarylene group having 4 to 10 carbons that may contain one or a plurality of oxygen, nitrogen and sulfur atoms on the ring, then J represents a substituted or unsubstituted, linear, cyclic or branched alkyl group having 1 to 6 carbons, a substituted or unsubstituted aryl group having 6 to 11 carbons, or a substituted or unsubstituted heteroaryl group having 4 to 10 carbons that may contain one or a plurality of oxygen, nitrogen and sulfur atoms on the ring, and preferably a substituted or unsubstituted aryl group having 6 to 11 carbons and a substituted or unsubstituted heteroaryl group (excluding unsubstituted pyridyl groups) having 4 to 10 carbons that may contain one or a plurality of oxygen, nitrogen and sulfur atoms on the ring may be mentioned. As the substituted or unsubstituted aryl group having 6 to 11 carbons, there can be mentioned a phenyl group, an indenyl group, a naphthyl group and the like, and preferably a phenyl group or a naphthyl group may be mentioned. As the substituted or unsubstituted, linear, cyclic or branched alkyl group having 1 to 6 carbons and as the substituted or unsubstituted heteroaryl group having 4 to 10 carbons that may contain one or a plurality of oxygen, nitrogen and sulfur atoms on the ring, there can be mentioned those described above. As the substituent as used herein, there can be mentioned a halogen atom, OH, $NO_2$, CN, a linear or branched alkyl group having 1 to 6 carbons, a linear or branched alkoxy group having 1 to 6 carbons (the substituents may be joined to each other at adjacent sites via an acetal bond), a linear or branched alkylthio group having 1 to 6 carbons, a linear or branched alkylsulfonyl group having 1 to 6 carbons, a linear or branched acyl group having 1 to 6 carbons, a linear or branched acylamino group having 1 to 6 carbons, a substituted or unsubstituted anilide group, a 20 trihalomethyl group, a trihalomethoxy group, a phenyl group, or a phenoxy group that may be substituted with one or more halogen atoms. They may be independently substituted at any one or more sites of the ring or the alkyl group. Specifically, there can be mentioned OH, a chloro group, a bromo group, a nitro group, a methoxy group, a cyano group, a methylenedioxy group, a trifluoromethyl group, a trifluoromethoxy group, a methyl group, an ethyl group, a (n, i-) propyl group, a (n, i, s, t-) butyl group, an anilide group and the like.

X represents CH or a nitrogen atom, and preferably CH may be mentioned.

As the compound of formula (1), specifically those described in Tables 1 to 40 are preferred. Most preferred among them are compounds Nos. 37, 50, 63, 64, 65, 84, 115, 117, 119, 121, 123, 130, 143, 147, 168, 174, 256, 264, 272, 311, 319, 320, 321, 324, 349, 352, 354, 355, 358, 364, 380, 392, 395, 398, 401, 402, 444, 455, 459, 460, 506, 863, 866, and 869.

A1 to A21 and J1 to J85 described in Tables 1 to 40 are the groups shown below, in which E and G are as described above.

A1
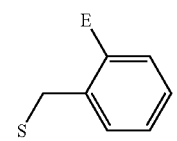

A2
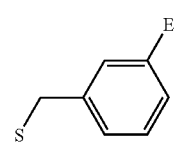

A3
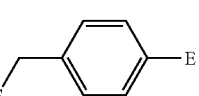

A4
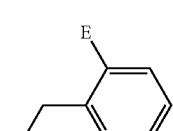

A5
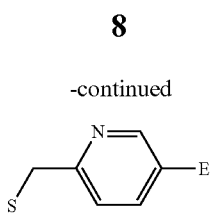

A6
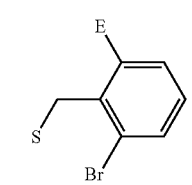

A7
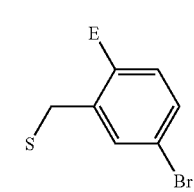

A8
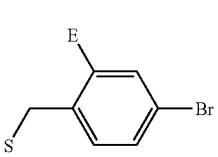

A9
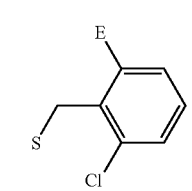

A10
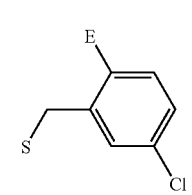

A11
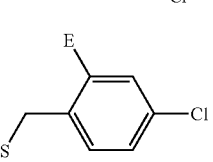

A12
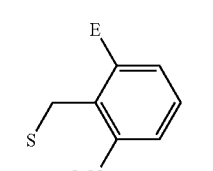

A13
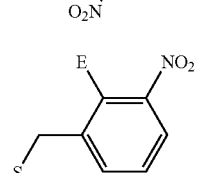

A14
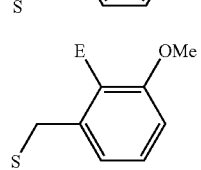

-continued
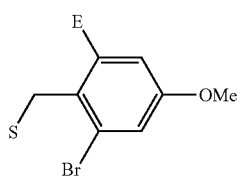 A15
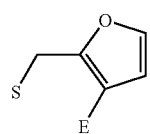 A16
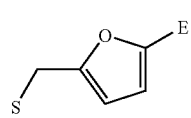 A17
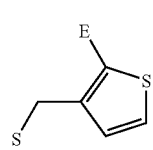 A18
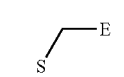 A19
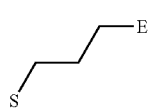 A20
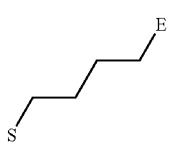 A21
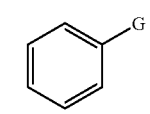 J1
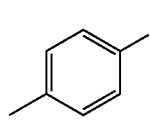 J2
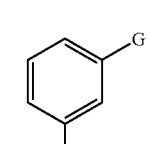 J3
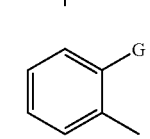 J4
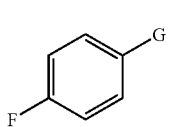 J5
-continued
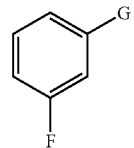 J6
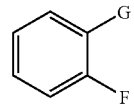 J7
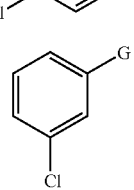 J8
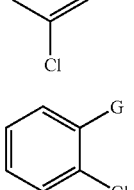 J9
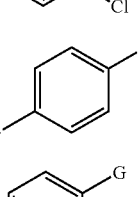 J10
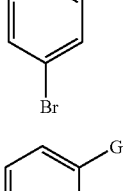 J11
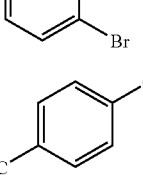 J12
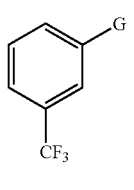 J13
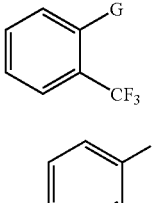 J14
 J15
 J16
 J17

-continued
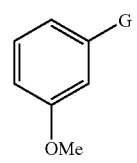 J18
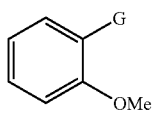 J19
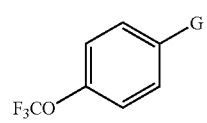 J20
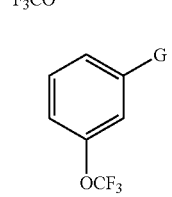 J21
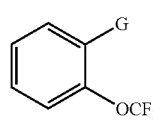 J22
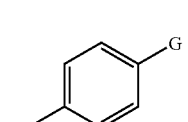 J23
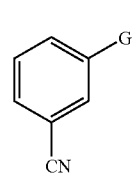 J24
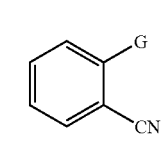 J25
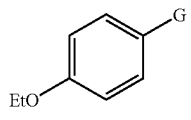 J26
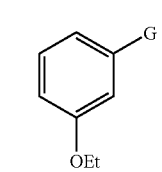 J27
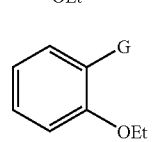 J28
-continued
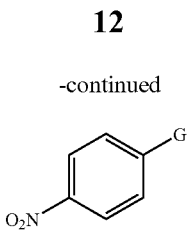 J29
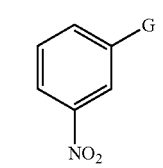 J30
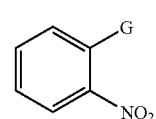 J31
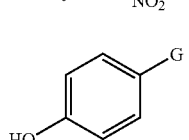 J32
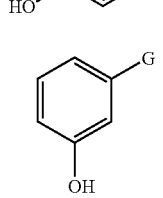 J33
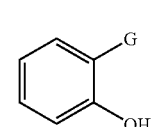 J34
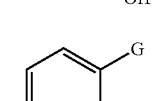 J35
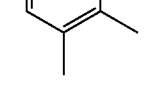 J36
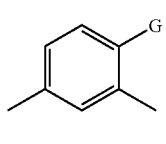 J37
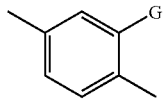 J38
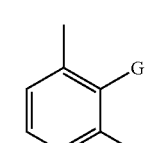 J39
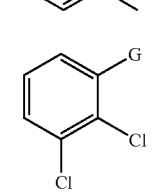

-continued
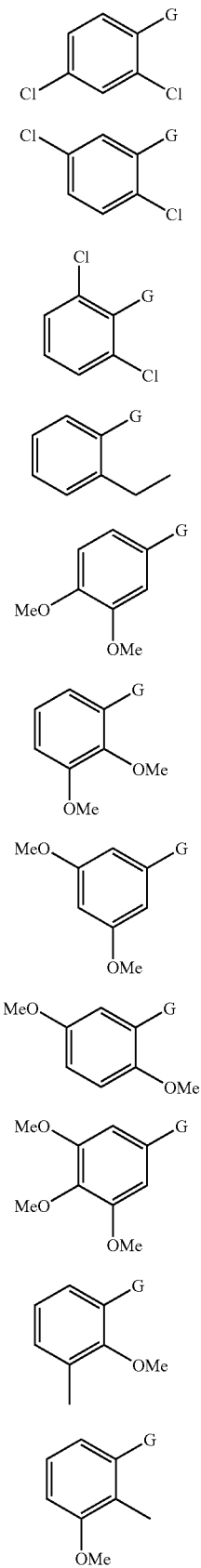
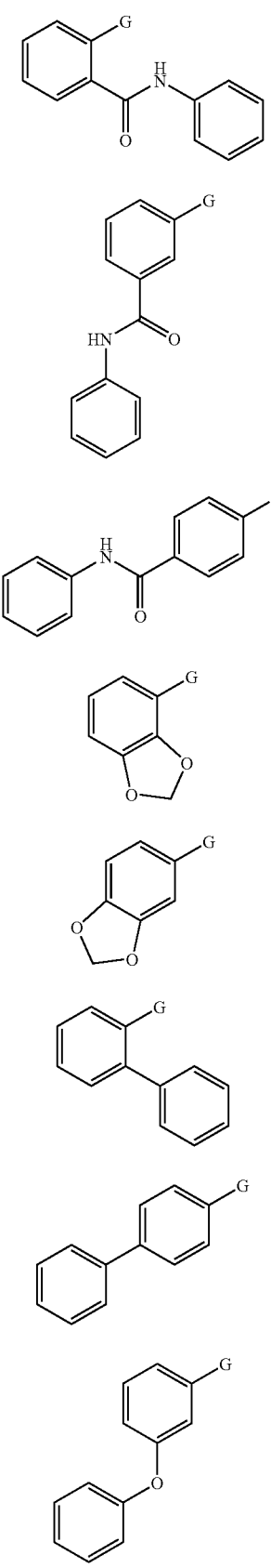

-continued
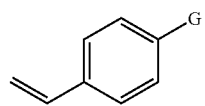 J59
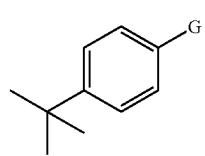 J60
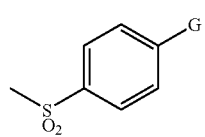 J61
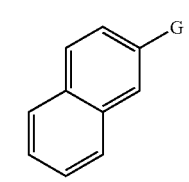 J62
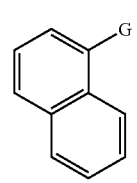 J63
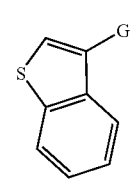 J64
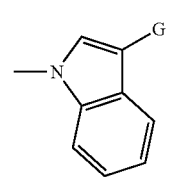 J65
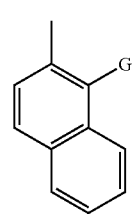 J66
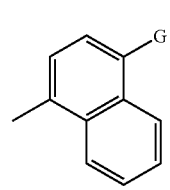 J67
-continued
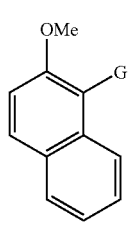 J68
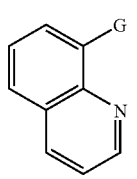 J69
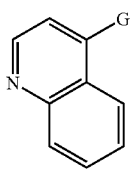 J70
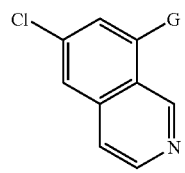 J71
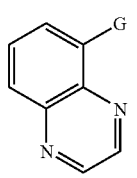 J72
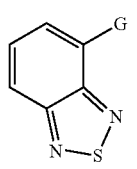 J73
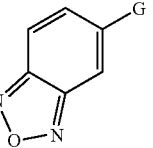 J74
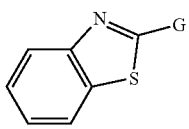 J75
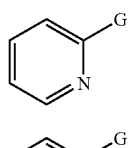 J76
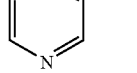 J77

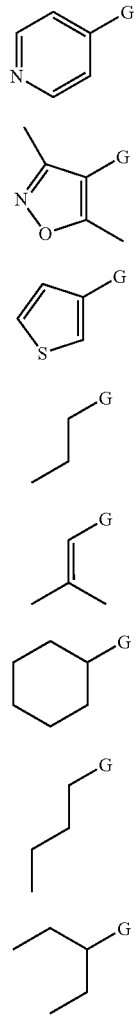

J78
J79
J80
J81
J82
J83
J84
J85

TABLE 1

| Compound No. | R¹ | R² | A | E | G | J | m | X |
|---|---|---|---|---|---|---|---|---|
| 1 | H | H | A1 | COOH | CH₂CH₂ | J1 | 0 | CH |
| 2 | H | H | A1 | COOH | CH₂ | J2 | 0 | CH |
| 3 | H | H | A1 | COOH | CH₂ | J3 | 0 | CH |
| 4 | H | H | A1 | COOH | CH₂ | J4 | 0 | CH |
| 5 | H | H | A1 | COOH | CH₂ | J5 | 0 | CH |
| 6 | H | H | A1 | COOH | CH₂ | J6 | 0 | CH |
| 7 | H | H | A1 | COOH | CH₂ | J7 | 0 | CH |
| 8 | H | H | A1 | COOH | CH₂ | J8 | 0 | CH |
| 9 | H | H | A1 | COOH | CH₂ | J9 | 0 | CH |
| 10 | H | H | A1 | COOH | CH₂ | J10 | 0 | CH |
| 11 | H | H | A1 | COOH | CH₂ | J11 | 0 | CH |
| 12 | H | H | A1 | COOH | CH₂ | J12 | 0 | CH |
| 13 | H | H | A1 | COOH | CH₂ | J13 | 0 | CH |
| 14 | H | H | A1 | COOH | CH₂ | J14 | 0 | CH |
| 15 | H | H | A1 | COOH | CH₂ | J15 | 0 | CH |
| 16 | H | H | A1 | COOH | CH₂ | J16 | 0 | CH |
| 17 | H | H | A1 | COOH | CH₂ | J17 | 0 | CH |
| 18 | H | H | A1 | COOH | CH₂ | J18 | 0 | CH |
| 19 | H | H | A1 | COOH | CH₂ | J19 | 0 | CH |
| 20 | H | H | A1 | COOH | CH₂ | J20 | 0 | CH |
| 21 | H | H | A1 | COOH | CH₂ | J21 | 0 | CH |
| 22 | H | H | A1 | COOH | CH₂ | J22 | 0 | CH |
| 23 | H | H | A1 | COOH | CH₂ | J23 | 0 | CH |
| 24 | H | H | A1 | COOH | CH₂ | J24 | 0 | CH |
| 25 | H | H | A1 | COOH | CH₂ | J25 | 0 | CH |

TABLE 2

| Compound No. | R¹ | R² | A | E | G | J | m | X |
|---|---|---|---|---|---|---|---|---|
| 26 | H | H | A1 | COOH | CH₂ | J26 | 0 | CH |
| 27 | H | H | A1 | COOH | CH₂ | J27 | 0 | CH |
| 28 | H | H | A1 | COOH | CH₂ | J28 | 0 | CH |
| 29 | H | H | A1 | COOH | CH₂ | J29 | 0 | CH |
| 30 | H | H | A1 | COOH | CH₂ | J30 | 0 | CH |
| 31 | H | H | A1 | COOH | CH₂ | J31 | 0 | CH |
| 32 | H | H | A1 | COOH | CH₂ | J32 | 0 | CH |
| 33 | H | H | A1 | COOH | CH₂ | J33 | 0 | CH |
| 34 | H | H | A1 | COOH | CH₂ | J34 | 0 | CH |
| 35 | H | H | A1 | COOH | CH₂ | J35 | 0 | CH |
| 36 | H | H | A1 | COOH | CH₂ | J36 | 0 | CH |
| 37 | H | H | A1 | COOH | CH₂ | J37 | 0 | CH |
| 38 | H | H | A1 | COOH | CH₂ | J38 | 0 | CH |
| 39 | H | H | A1 | COOH | CH₂ | J39 | 0 | CH |
| 40 | H | H | A1 | COOH | CH₂ | J40 | 0 | CH |
| 41 | H | H | A1 | COOH | CH₂ | J41 | 0 | CH |
| 42 | H | H | A1 | COOH | CH₂ | J42 | 0 | CH |
| 43 | H | H | A1 | COOH | CH₂ | J43 | 0 | CH |
| 44 | H | H | A1 | COOH | CH₂ | J44 | 0 | CH |
| 45 | H | H | A1 | COOH | CH₂ | J45 | 0 | CH |
| 46 | H | H | A1 | COOH | CH₂ | J46 | 0 | CH |
| 47 | H | H | A1 | COOH | CH₂ | J47 | 0 | CH |
| 48 | H | H | A1 | COOH | CH₂ | J48 | 0 | CH |
| 49 | H | H | A1 | COOH | CH₂ | J49 | 0 | CH |
| 50 | H | H | A1 | COOH | CH₂ | J50 | 0 | CH |

TABLE 3

| Compound No. | R¹ | R² | A | E | G | J | m | X |
|---|---|---|---|---|---|---|---|---|
| 51 | H | H | A1 | COOH | CH₂ | J51 | 0 | CH |
| 52 | H | H | A1 | COOH | CH₂ | J52 | 0 | CH |
| 53 | H | H | A1 | COOH | CH₂ | J53 | 0 | CH |
| 54 | H | H | A1 | COOH | CH₂ | J54 | 0 | CH |
| 55 | H | H | A1 | COOH | CH₂ | J55 | 0 | CH |
| 56 | H | H | A1 | COOH | CH₂ | J56 | 0 | CH |
| 57 | H | H | A1 | COOH | CH₂ | J57 | 0 | CH |
| 58 | H | H | A1 | COOH | CH₂ | J58 | 0 | CH |
| 59 | H | H | A1 | COOH | CH₂ | J59 | 0 | CH |
| 60 | H | H | A1 | COOH | CH₂ | J60 | 0 | CH |
| 61 | H | H | A1 | COOH | CH₂ | J61 | 0 | CH |
| 62 | H | H | A1 | COOH | CH₂ | J62 | 0 | CH |
| 63 | H | H | A1 | COOH | CH₂ | J63 | 0 | CH |
| 64 | H | H | A1 | COOH | CH₂ | J64 | 0 | CH |
| 65 | H | H | A1 | COOH | CH₂ | J65 | 0 | CH |
| 66 | H | H | A1 | COOH | CH₂ | J66 | 0 | CH |
| 67 | H | H | A1 | COOH | CH₂ | J67 | 0 | CH |
| 68 | H | H | A1 | COOH | CH₂ | J68 | 0 | CH |
| 69 | H | H | A1 | COOH | CH₂ | J69 | 0 | CH |
| 70 | H | H | A1 | COOH | CH₂ | J70 | 0 | CH |
| 71 | H | H | A1 | COOH | CH₂ | J71 | 0 | CH |
| 72 | H | H | A1 | COOH | CH₂ | J72 | 0 | CH |
| 73 | H | H | A1 | COOH | CH₂ | J73 | 0 | CH |
| 74 | H | H | A1 | COOH | CH₂ | J74 | 0 | CH |
| 75 | H | H | A1 | COOH | CH₂ | J75 | 0 | CH |

TABLE 4

| Compound No. | R¹ | R² | A | E | G | J | m | X |
|---|---|---|---|---|---|---|---|---|
| 76 | H | H | A1 | COOH | $CH_2$ | J76 | 0 | CH |
| 77 | H | H | A1 | COOH | $CH_2$ | J77 | 0 | CH |
| 78 | H | H | A1 | COOH | $CH_2$ | J78 | 0 | CH |
| 79 | H | H | A1 | COOH | $CH_2$ | J79 | 0 | CH |
| 80 | H | H | A1 | COOH | $CH_2$ | J80 | 0 | CH |
| 81 | Me | Me | A1 | COOH | $CH_2$ | J1 | 0 | CH |
| 82 | Me | Me | A1 | COOH | $CH_2$ | J2 | 0 | CH |
| 83 | Me | Me | A1 | COOH | $CH_2$ | J3 | 0 | CH |
| 84 | Me | Me | A1 | COOH | $CH_2$ | J4 | 0 | CH |
| 85 | Me | Me | A1 | COOH | $CH_2$ | J5 | 0 | CH |
| 86 | Me | Me | A1 | COOH | $CH_2$ | J6 | 0 | CH |
| 87 | Me | Me | A1 | COOH | $CH_2$ | J7 | 0 | CH |
| 88 | Me | Me | A1 | COOH | $CH_2$ | J8 | 0 | CH |
| 89 | Me | Me | A1 | COOH | $CH_2$ | J9 | 0 | CH |
| 90 | Me | Me | A1 | COOH | $CH_2$ | J10 | 0 | CH |
| 91 | Me | Me | A1 | COOH | $CH_2$ | J11 | 0 | CH |
| 92 | Me | Me | A1 | COOH | $CH_2$ | J12 | 0 | CH |
| 93 | Me | Me | A1 | COOH | $CH_2$ | J13 | 0 | CH |
| 94 | Me | Me | A1 | COOH | $CH_2$ | J14 | 0 | CH |
| 95 | Me | Me | A1 | COOH | $CH_2$ | J15 | 0 | CH |
| 96 | Me | Me | A1 | COOH | $CH_2$ | J16 | 0 | CH |
| 97 | Me | Me | A1 | COOH | $CH_2$ | J17 | 0 | CH |
| 98 | Me | Me | A1 | COOH | $CH_2$ | J18 | 0 | CH |
| 99 | Me | Me | A1 | COOH | $CH_2$ | J19 | 0 | CH |
| 100 | Me | Me | A1 | COOH | $CH_2$ | J20 | 0 | CH |

TABLE 5

| Compound No. | R¹ | R² | A | E | G | J | m | X |
|---|---|---|---|---|---|---|---|---|
| 101 | Me | Me | A1 | COOH | $CH_2$ | J21 | 0 | CH |
| 102 | Me | Me | A1 | COOH | $CH_2$ | J22 | 0 | CH |
| 103 | Me | Me | A1 | COOH | $CH_2$ | J23 | 0 | CH |
| 104 | Me | Me | A1 | COOH | $CH_2$ | J24 | 0 | CH |
| 105 | Me | Me | A1 | COOH | $CH_2$ | J25 | 0 | CH |
| 106 | Me | Me | A1 | COOH | $CH_2$ | J26 | 0 | CH |
| 107 | Me | Me | A1 | COOH | $CH_2$ | J27 | 0 | CH |
| 108 | Me | Me | A1 | COOH | $CH_2$ | J28 | 0 | CH |
| 109 | Me | Me | A1 | COOH | $CH_2$ | J29 | 0 | CH |
| 110 | Me | Me | A1 | COOH | $CH_2$ | J30 | 0 | CH |
| 111 | Me | Me | A1 | COOH | $CH_2$ | J31 | 0 | CH |
| 112 | Me | Me | A1 | COOH | $CH_2$ | J32 | 0 | CH |
| 113 | Me | Me | A1 | COOH | $CH_2$ | J33 | 0 | CH |
| 114 | Me | Me | A1 | COOH | $CH_2$ | J34 | 0 | CH |
| 115 | Me | Me | A1 | COOH | $CH_2$ | J35 | 0 | CH |
| 116 | Me | Me | A1 | COOH | $CH_2$ | J36 | 0 | CH |
| 117 | Me | Me | A1 | COOH | $CH_2$ | J37 | 0 | CH |
| 118 | Me | Me | A1 | COOH | $CH_2$ | J38 | 0 | CH |
| 119 | Me | Me | A1 | COOH | $CH_2$ | J39 | 0 | CH |
| 120 | Me | Me | A1 | COOH | $CH_2$ | J40 | 0 | CH |
| 121 | Me | Me | A1 | COOH | $CH_2$ | J41 | 0 | CH |
| 122 | Me | Me | A1 | COOH | $CH_2$ | J42 | 0 | CH |
| 123 | Me | Me | A1 | COOH | $CH_2$ | J43 | 0 | CH |
| 124 | Me | Me | A1 | COOH | $CH_2$ | J44 | 0 | CH |
| 125 | Me | Me | A1 | COOH | $CH_2$ | J45 | 0 | CH |

TABLE 6

| Compound No. | R¹ | R² | A | E | G | J | m | X |
|---|---|---|---|---|---|---|---|---|
| 126 | Me | Me | A1 | COOH | $CH_2$ | J46 | 0 | CH |
| 127 | Me | Me | A1 | COOH | $CH_2$ | J47 | 0 | CH |
| 128 | Me | Me | A1 | COOH | $CH_2$ | J48 | 0 | CH |
| 129 | Me | Me | A1 | COOH | $CH_2$ | J49 | 0 | CH |
| 130 | Me | Me | A1 | COOH | $CH_2$ | J50 | 0 | CH |
| 131 | Me | Me | A1 | COOH | $CH_2$ | J51 | 0 | CH |
| 132 | Me | Me | A1 | COOH | $CH_2$ | J52 | 0 | CH |
| 133 | Me | Me | A1 | COOH | $CH_2$ | J53 | 0 | CH |
| 134 | Me | Me | A1 | COOH | $CH_2$ | J54 | 0 | CH |
| 135 | Me | Me | A1 | COOH | $CH_2$ | J55 | 0 | CH |
| 136 | Me | Me | A1 | COOH | $CH_2$ | J56 | 0 | CH |
| 137 | Me | Me | A1 | COOH | $CH_2$ | J57 | 0 | CH |
| 138 | Me | Me | A1 | COOH | $CH_2$ | J58 | 0 | CH |
| 139 | Me | Me | A1 | COOH | $CH_2$ | J59 | 0 | CH |
| 140 | Me | Me | A1 | COOH | $CH_2$ | J60 | 0 | CH |
| 141 | Me | Me | A1 | COOH | $CH_2$ | J61 | 0 | CH |
| 142 | Me | Me | A1 | COOH | $CH_2$ | J62 | 0 | CH |
| 143 | Me | Me | A1 | COOH | $CH_2$ | J63 | 0 | CH |
| 144 | Me | Me | A1 | COOH | $CH_2$ | J64 | 0 | CH |
| 145 | Me | Me | A1 | COOH | $CH_2$ | J65 | 0 | CH |
| 146 | Me | Me | A1 | COOH | $CH_2$ | J66 | 0 | CH |
| 147 | Me | Me | A1 | COOH | $CH_2$ | J67 | 0 | CH |
| 148 | Me | Me | A1 | COOH | $CH_2$ | J68 | 0 | CH |
| 149 | Me | Me | A1 | COOH | $CH_2$ | J69 | 0 | CH |
| 150 | Me | Me | A1 | COOH | $CH_2$ | J70 | 0 | CH |

TABLE 7

| Compound No. | R¹ | R² | A | E | G | J | m | X |
|---|---|---|---|---|---|---|---|---|
| 151 | Me | Me | A1 | COOH | $CH_2$ | J71 | 0 | CH |
| 152 | Me | Me | A1 | COOH | $CH_2$ | J72 | 0 | CH |
| 153 | Me | Me | A1 | COOH | $CH_2$ | J73 | 0 | CH |
| 154 | Me | Me | A1 | COOH | $CH_2$ | J74 | 0 | CH |
| 155 | Me | Me | A1 | COOH | $CH_2$ | J75 | 0 | CH |
| 156 | Me | Me | A1 | COOH | $CH_2$ | J76 | 0 | CH |
| 157 | Me | Me | A1 | COOH | $CH_2$ | J77 | 0 | CH |
| 158 | Me | Me | A1 | COOH | $CH_2$ | J78 | 0 | CH |
| 159 | Me | Me | A1 | COOH | $CH_2$ | J79 | 0 | CH |
| 160 | Me | Me | A1 | COOH | $CH_2$ | J80 | 0 | CH |
| 161 | Cl | Cl | A1 | COOH | $CH_2CH_2$ | J1 | 0 | CH |
| 162 | Cl | Cl | A1 | COOH | $CH_2$ | J4 | 0 | CH |
| 163 | Cl | Cl | A1 | COOH | $CH_2$ | J10 | 0 | CH |
| 164 | Cl | Cl | A1 | COOH | $CH_2$ | J18 | 0 | CH |
| 165 | Cl | Cl | A1 | COOH | $CH_2$ | J21 | 0 | CH |
| 166 | Cl | Cl | A1 | COOH | $CH_2$ | J28 | 0 | CH |
| 167 | Cl | Cl | A1 | COOH | $CH_2$ | J35 | 0 | CH |
| 168 | Cl | Cl | A1 | COOH | $CH_2$ | J37 | 0 | CH |
| 169 | Cl | Cl | A1 | COOH | $CH_2$ | J39 | 0 | CH |
| 170 | Cl | Cl | A1 | COOH | $CH_2$ | J43 | 0 | CH |
| 171 | Cl | Cl | A1 | COOH | $CH_2$ | J46 | 0 | CH |
| 172 | Cl | Cl | A1 | COOH | $CH_2$ | J50 | 0 | CH |
| 173 | Cl | Cl | A1 | COOH | $CH_2$ | J54 | 0 | CH |
| 174 | Cl | Cl | A1 | COOH | $CH_2$ | J63 | 0 | CH |
| 175 | Cl | Cl | A1 | COOH | $CH_2$ | J64 | 0 | CH |

TABLE 8

| Compound No. | R¹ | R² | A | E | G | J | m | X |
|---|---|---|---|---|---|---|---|---|
| 176 | Cl | Cl | A1 | COOH | $CH_2$ | J65 | 0 | CH |
| 177 | Cl | Cl | A1 | COOH | $CH_2$ | J66 | 0 | CH |
| 178 | Cl | Cl | A1 | COOH | $CH_2$ | J67 | 0 | CH |
| 179 | Cl | Cl | A1 | COOH | $CH_2$ | J71 | 0 | CH |
| 180 | —$CH_2CH_2CH_2$— | | A1 | COOH | $CH_2CH_2$ | J1 | 0 | CH |
| 181 | —$CH_2CH_2CH_2$— | | A1 | COOH | $CH_2$ | J4 | 0 | CH |
| 182 | —$CH_2CH_2CH_2$— | | A1 | COOH | $CH_2$ | J10 | 0 | CH |
| 183 | —$CH_2CH_2CH_2$— | | A1 | COOH | $CH_2$ | J18 | 0 | CH |
| 184 | —$CH_2CH_2CH_2$— | | A1 | COOH | $CH_2$ | J21 | 0 | CH |
| 185 | —$CH_2CH_2CH_2$— | | A1 | COOH | $CH_2$ | J28 | 0 | CH |
| 186 | —$CH_2CH_2CH_2$— | | A1 | COOH | $CH_2$ | J35 | 0 | CH |
| 187 | —$CH_2CH_2CH_2$— | | A1 | COOH | $CH_2$ | J37 | 0 | CH |
| 188 | —$CH_2CH_2CH_2$— | | A1 | COOH | $CH_2$ | J39 | 0 | CH |
| 189 | —$CH_2CH_2CH_2$— | | A1 | COOH | $CH_2$ | J43 | 0 | CH |
| 190 | —$CH_2CH_2CH_2$— | | A1 | COOH | $CH_2$ | J46 | 0 | CH |
| 191 | —$CH_2CH_2CH_2$— | | A1 | COOH | $CH_2$ | J50 | 0 | CH |
| 192 | —$CH_2CH_2CH_2$— | | A1 | COOH | $CH_2$ | J54 | 0 | CH |
| 193 | —$CH_2CH_2CH_2$— | | A1 | COOH | $CH_2$ | J63 | 0 | CH |

TABLE 8-continued

| Compound No. | R¹ | R² | A | E | G | J | m | X |
|---|---|---|---|---|---|---|---|---|
| 194 | —CH₂CH₂CH₂— | | A1 | COOH | CH₂ | J64 | 0 | CH |
| 195 | —CH₂CH₂CH₂— | | A1 | COOH | CH₂ | J65 | 0 | CH |
| 196 | —CH₂CH₂CH₂— | | A1 | COOH | CH₂ | J66 | 0 | CH |
| 197 | —CH₂CH₂CH₂— | | A1 | COOH | CH₂ | J67 | 0 | CH |
| 198 | —CH₂CH₂CH₂— | | A1 | COOH | CH₂ | J71 | 0 | CH |
| 199 | —OCH₂O— | | A1 | COOH | CH₂CH₂ | J1 | 0 | CH |
| 200 | —OCH₂O— | | A1 | COOH | CH₂ | J4 | 0 | CH |

TABLE 9

| Compound No. | R¹ | R² | A | E | G | J | m | X |
|---|---|---|---|---|---|---|---|---|
| 201 | —OCH₂O— | | A1 | COOH | CH₂ | J10 | 0 | CH |
| 202 | —OCH₂O— | | A1 | COOH | CH₂ | J18 | 0 | CH |
| 203 | —OCH₂O— | | A1 | COOH | CH₂ | J21 | 0 | CH |
| 204 | —OCH₂O— | | A1 | COOH | CH₂ | J28 | 0 | CH |
| 205 | —OCH₂O— | | A1 | COOH | CH₂ | J35 | 0 | CH |
| 206 | —OCH₂O— | | A1 | COOH | CH₂ | J37 | 0 | CH |
| 207 | —OCH₂O— | | A1 | COOH | CH₂ | J39 | 0 | CH |
| 208 | —OCH₂O— | | A1 | COOH | CH₂ | J43 | 0 | CH |
| 209 | —OCH₂O— | | A1 | COOH | CH₂ | J46 | 0 | CH |
| 210 | —OCH₂O— | | A1 | COOH | CH₂ | J50 | 0 | CH |
| 211 | —OCH₂O— | | A1 | COOH | CH₂ | J54 | 0 | CH |
| 212 | —OCH₂O— | | A1 | COOH | CH₂ | J63 | 0 | CH |
| 213 | —OCH₂O— | | A1 | COOH | CH₂ | J64 | 0 | CH |
| 214 | —OCH₂O— | | A1 | COOH | CH₂ | J65 | 0 | CH |
| 215 | —OCH₂O— | | A1 | COOH | CH₂ | J66 | 0 | CH |
| 216 | —OCH₂O— | | A1 | COOH | CH₂ | J67 | 0 | CH |
| 217 | —OCH₂O— | | A1 | COOH | CH₂ | J71 | 0 | CH |
| 218 | —OCH₂CH₂O— | | A1 | COOH | CH₂CH₂ | J1 | 0 | CH |
| 219 | —OCH₂CH₂O— | | A1 | COOH | CH₂ | J4 | 0 | CH |
| 220 | —OCH₂CH₂O— | | A1 | COOH | CH₂ | J10 | 0 | CH |
| 221 | —OCH₂CH₂O— | | A1 | COOH | CH₂ | J18 | 0 | CH |
| 222 | —OCH₂CH₂O— | | A1 | COOH | CH₂ | J35 | 0 | CH |
| 223 | —OCH₂CH₂O— | | A1 | COOH | CH₂ | J37 | 0 | CH |
| 224 | —OCH₂CH₂O— | | A1 | COOH | CH₂ | J39 | 0 | CH |
| 225 | —OCH₂CH₂O— | | A1 | COOH | CH₂ | J50 | 0 | CH |

TABLE 10

| Compound No. | R¹ | R² | A | E | G | J | m | X |
|---|---|---|---|---|---|---|---|---|
| 226 | —OCH₂CH₂O— | | A1 | COOH | CH₂ | J63 | 0 | CH |
| 227 | —OCH₂CH₂O— | | A1 | COOH | CH₂ | J64 | 0 | CH |
| 228 | —OCH₂CH₂O— | | A1 | COOH | CH₂ | J65 | 0 | CH |
| 229 | —OCH₂CH₂O— | | A1 | COOH | CH₂ | J67 | 0 | CH |
| 230 | —OCH₂CH₂O— | | A1 | COOH | CH₂ | J71 | 0 | CH |
| 231 | OMe | OMe | A1 | COOH | CH₂CH₂ | J1 | 0 | CH |
| 232 | OMe | OMe | A1 | COOH | CH₂ | J4 | 0 | CH |
| 233 | OMe | OMe | A1 | COOH | CH₂ | J10 | 0 | CH |
| 234 | OMe | OMe | A1 | COOH | CH₂ | J18 | 0 | CH |
| 235 | OMe | OMe | A1 | COOH | CH₂ | J35 | 0 | CH |
| 236 | OMe | OMe | A1 | COOH | CH₂ | J37 | 0 | CH |
| 237 | OMe | OMe | A1 | COOH | CH₂ | J39 | 0 | CH |
| 238 | OMe | OMe | A1 | COOH | CH₂ | J50 | 0 | CH |
| 239 | OMe | OMe | A1 | COOH | CH₂ | J63 | 0 | CH |
| 240 | OMe | OMe | A1 | COOH | CH₂ | J64 | 0 | CH |
| 241 | OMe | OMe | A1 | COOH | CH₂ | J65 | 0 | CH |
| 242 | OMe | OMe | A1 | COOH | CH₂ | J67 | 0 | CH |
| 243 | OMe | OMe | A1 | COOH | CH₂ | J71 | 0 | CH |
| 244 | F | F | A1 | COOH | CH₂ | J35 | 0 | CH |
| 245 | F | F | A1 | COOH | CH₂ | J37 | 0 | CH |
| 246 | F | F | A1 | COOH | CH₂ | J39 | 0 | CH |
| 247 | F | F | A1 | COOH | CH₂ | J50 | 0 | CH |
| 248 | F | F | A1 | COOH | CH₂ | J63 | 0 | CH |
| 249 | F | F | A1 | COOH | CH₂ | J64 | 0 | CH |
| 250 | F | F | A1 | COOH | CH₂ | J65 | 0 | CH |

TABLE 11

| Compound No. | R¹ | R² | A | E | G | J | m | X |
|---|---|---|---|---|---|---|---|---|
| 251 | F | F | A1 | COOH | CH₂ | J67 | 0 | CH |
| 252 | H | H | A1 | COOH | CH₂ | J35 | 0 | N |
| 253 | H | H | A1 | COOH | CH₂ | J37 | 0 | N |
| 254 | H | H | A1 | COOH | CH₂ | J39 | 0 | N |
| 255 | H | H | A1 | COOH | CH₂ | J50 | 0 | N |
| 256 | H | H | A1 | COOH | CH₂ | J63 | 0 | N |
| 257 | H | H | A1 | COOH | CH₂ | J64 | 0 | N |
| 258 | H | H | A1 | COOH | CH₂ | J65 | 0 | N |
| 259 | H | H | A1 | COOH | CH₂ | J67 | 0 | N |
| 260 | Me | H | A1 | COOH | CH₂ | J35 | 0 | CH |
| 261 | Me | H | A1 | COOH | CH₂ | J37 | 0 | CH |
| 262 | Me | H | A1 | COOH | CH₂ | J39 | 0 | CH |
| 263 | Me | H | A1 | COOH | CH₂ | J50 | 0 | CH |
| 264 | Me | H | A1 | COOH | CH₂ | J63 | 0 | CH |
| 265 | Me | H | A1 | COOH | CH₂ | J64 | 0 | CH |
| 266 | Me | H | A1 | COOH | CH₂ | J65 | 0 | CH |
| 267 | Me | H | A1 | COOH | CH₂ | J67 | 0 | CH |
| 268 | OMe | H | A1 | COOH | CH₂ | J35 | 0 | CH |
| 269 | OMe | H | A1 | COOH | CH₂ | J37 | 0 | CH |
| 270 | OMe | H | A1 | COOH | CH₂ | J39 | 0 | CH |
| 271 | OMe | H | A1 | COOH | CH₂ | J50 | 0 | CH |
| 272 | OMe | H | A1 | COOH | CH₂ | J63 | 0 | CH |
| 273 | OMe | H | A1 | COOH | CH₂ | J64 | 0 | CH |
| 274 | OMe | H | A1 | COOH | CH₂ | J65 | 0 | CH |
| 275 | OMe | H | A1 | COOH | CH₂ | J67 | 0 | CH |

TABLE 12

| Compound No. | R¹ | R² | A | E | G | J | m | X |
|---|---|---|---|---|---|---|---|---|
| 276 | OEt | H | A1 | COOH | CH₂ | J63 | 0 | CH |
| 277 | OEt | H | A1 | COOH | CH₂ | J64 | 0 | CH |
| 278 | OEt | H | A1 | COOH | CH₂ | J65 | 0 | CH |
| 279 | CF3 | H | A1 | COOH | CH₂ | J63 | 0 | CH |
| 280 | CF3 | H | A1 | COOH | CH₂ | J64 | 0 | CH |
| 281 | CF3 | H | A1 | COOH | CH₂ | J65 | 0 | CH |
| 282 | CN | H | A1 | COOH | CH₂ | J63 | 0 | CH |
| 283 | CN | H | A1 | COOH | CH₂ | J64 | 0 | CH |
| 284 | CN | H | A1 | COOH | CH₂ | J65 | 0 | CH |
| 285 | Cl | H | A1 | COOH | CH₂ | J63 | 0 | N |
| 286 | Cl | H | A1 | COOH | CH₂ | J64 | 0 | N |
| 287 | Cl | H | A1 | COOH | CH₂ | J65 | 0 | N |
| 288 | Me | Me | A2 | COOH | CH₂ | J35 | 0 | CH |
| 289 | Me | Me | A2 | COOH | CH₂ | J37 | 0 | CH |
| 290 | Me | Me | A2 | COOH | CH₂ | J39 | 0 | CH |
| 291 | Me | Me | A2 | COOH | CH₂ | J63 | 0 | CH |
| 292 | Me | Me | A2 | COOH | CH₂ | J64 | 0 | CH |
| 293 | Me | Me | A2 | COOH | CH₂ | J65 | 0 | CH |
| 294 | Me | Me | A2 | COOH | CH₂CH₂ | J1 | 0 | CH |
| 295 | Me | Me | A3 | COOH | CH₂ | J1 | 0 | CH |
| 296 | Me | Me | A3 | COOH | CH₂ | J35 | 0 | CH |
| 297 | Me | Me | A3 | COOH | CH₂ | J37 | 0 | CH |
| 298 | Me | Me | A3 | COOH | CH₂ | J39 | 0 | CH |
| 299 | Me | Me | A3 | COOH | CH₂ | J50 | 0 | CH |
| 300 | Me | Me | A3 | COOH | CH₂ | J63 | 0 | CH |

TABLE 13

| Compound No. | R¹ | R² | A | E | G | J | m | X |
|---|---|---|---|---|---|---|---|---|
| 301 | Me | Me | A3 | COOH | CH₂ | J64 | 0 | CH |
| 302 | Me | Me | A3 | COOH | CH₂ | J65 | 0 | CH |
| 303 | Me | Me | A3 | COOH | CH₂ | J67 | 0 | CH |
| 304 | Me | Me | A3 | COOH | CH₂CH₂ | J1 | 0 | CH |
| 305 | Me | Me | A3 | COOH | CH₂CH₂ | J63 | 0 | CH |
| 306 | Me | Me | A4 | COOH | CH₂ | J1 | 0 | CH |
| 307 | Me | Me | A4 | COOH | CH₂ | J35 | 0 | CH |
| 308 | Me | Me | A4 | COOH | CH₂ | J37 | 0 | CH |
| 309 | Me | Me | A4 | COOH | CH₂ | J39 | 0 | CH |
| 310 | Me | Me | A4 | COOH | CH₂ | J50 | 0 | CH |

TABLE 13-continued

| Compound No. | R¹ | R² | A | E | G | J | m | X |
|---|---|---|---|---|---|---|---|---|
| 311 | Me | Me | A4 | COOH | $CH_2$ | J63 | 0 | CH |
| 312 | Me | Me | A4 | COOH | $CH_2$ | J64 | 0 | CH |
| 313 | Me | Me | A4 | COOH | $CH_2$ | J65 | 0 | CH |
| 314 | Me | Me | A4 | COOH | $CH_2$ | J67 | 0 | CH |
| 315 | Me | Me | A4 | COOH | $CH_2CH_2$ | J1 | 0 | CH |
| 316 | Me | Me | A4 | COOH | $CH_2CH_2$ | J63 | 0 | CH |
| 317 | H | H | A4 | COOH | $CH_2$ | J37 | 0 | CH |
| 318 | H | H | A4 | COOH | $CH_2$ | J39 | 0 | CH |
| 319 | H | H | A4 | COOH | $CH_2$ | J63 | 0 | CH |
| 320 | H | H | A4 | COOH | $CH_2$ | J64 | 0 | CH |
| 321 | H | H | A4 | COOH | $CH_2$ | J65 | 0 | CH |
| 322 | Cl | Cl | A4 | COOH | $CH_2$ | J37 | 0 | CH |
| 323 | Cl | Cl | A4 | COOH | $CH_2$ | J39 | 0 | CH |
| 324 | Cl | Cl | A4 | COOH | $CH_2$ | J63 | 0 | CH |
| 325 | Cl | Cl | A4 | COOH | $CH_2$ | J64 | 0 | CH |

TABLE 14

| Compound No. | R¹ | R² | A | E | G | J | m | X |
|---|---|---|---|---|---|---|---|---|
| 326 | Cl | Cl | A4 | COOH | $CH_2$ | J65 | 0 | CH |
| 327 | H | H | A4 | COOH | $CH_2$ | J37 | 0 | N |
| 328 | H | H | A4 | COOH | $CH_2$ | J39 | 0 | N |
| 329 | H | H | A4 | COOH | $CH_2$ | J63 | 0 | N |
| 330 | H | H | A4 | COOH | $CH_2$ | J64 | 0 | N |
| 331 | H | H | A4 | COOH | $CH_2$ | J65 | 0 | N |
| 332 | Me | Me | A5 | COOH | $CH_2$ | J1 | 0 | CH |
| 333 | Me | Me | A5 | COOH | $CH_2CH_2$ | J1 | 0 | CH |
| 334 | Me | Me | A6 | COOH | $CH_2$ | J1 | 0 | CH |
| 335 | Me | Me | A6 | COOH | $CH_2CH_2$ | J1 | 0 | CH |
| 336 | Me | Me | A7 | COOH | $CH_2$ | J1 | 0 | CH |
| 337 | Me | Me | A7 | COOH | $CH_2CH_2$ | J1 | 0 | CH |
| 338 | Me | Me | A8 | COOH | $CH_2$ | J1 | 0 | CH |
| 339 | Me | Me | A8 | COOH | $CH_2CH_2$ | J1 | 0 | CH |
| 340 | Me | Me | A9 | COOH | $CH_2$ | J1 | 0 | CH |
| 341 | Me | Me | A9 | COOH | $CH_2CH_2$ | J1 | 0 | CH |
| 342 | Me | Me | A10 | COOH | $CH_2$ | J1 | 0 | CH |
| 343 | Me | Me | A10 | COOH | $CH_2CH_2$ | J1 | 0 | CH |
| 344 | Me | Me | A11 | COOH | $CH_2$ | J37 | 0 | CH |
| 345 | Me | Me | A11 | COOH | $CH_2$ | J39 | 0 | CH |
| 346 | Me | Me | A11 | COOH | $CH_2$ | J50 | 0 | CH |
| 347 | Me | Me | A11 | COOH | $CH_2$ | J63 | 0 | CH |
| 348 | Me | Me | A11 | COOH | $CH_2$ | J64 | 0 | CH |
| 349 | H | H | A11 | COOH | $CH_2$ | J37 | 0 | CH |
| 350 | H | H | A11 | COOH | $CH_2$ | J39 | 0 | CH |

TABLE 15

| Compound No. | R¹ | R² | A | E | G | J | m | X |
|---|---|---|---|---|---|---|---|---|
| 351 | H | H | A11 | COOH | $CH_2$ | J50 | 0 | CH |
| 352 | H | H | A11 | COOH | $CH_2$ | J63 | 0 | CH |
| 353 | H | H | A11 | COOH | $CH_2$ | J64 | 0 | CH |
| 354 | H | H | A11 | COOH | $CH_2$ | J65 | 0 | CH |
| 355 | Cl | Cl | A11 | COOH | $CH_2$ | J37 | 0 | CH |
| 356 | Cl | Cl | A11 | COOH | $CH_2$ | J39 | 0 | CH |
| 357 | Cl | Cl | A11 | COOH | $CH_2$ | J50 | 0 | CH |
| 358 | Cl | Cl | A11 | COOH | $CH_2$ | J63 | 0 | CH |
| 359 | Cl | Cl | A11 | COOH | $CH_2$ | J64 | 0 | CH |
| 360 | Cl | Cl | A11 | COOH | $CH_2$ | J65 | 0 | CH |
| 361 | H | H | A11 | COOH | $CH_2$ | J37 | 0 | N |
| 362 | H | H | A11 | COOH | $CH_2$ | J39 | 0 | N |
| 363 | H | H | A11 | COOH | $CH_2$ | J50 | 0 | N |
| 364 | H | H | A11 | COOH | $CH_2$ | J63 | 0 | N |
| 365 | H | H | A11 | COOH | $CH_2$ | J64 | 0 | N |
| 366 | H | H | A11 | COOH | $CH_2$ | J65 | 0 | N |
| 367 | Me | Me | A12 | COOH | $CH_2$ | J1 | 0 | CH |
| 368 | Me | Me | A12 | COOH | $CH_2CH_2$ | J1 | 0 | CH |
| 369 | Me | Me | A13 | COOH | $CH_2$ | J1 | 0 | CH |
| 370 | Me | Me | A13 | COOH | $CH_2CH_2$ | J1 | 0 | CH |
| 371 | Me | Me | A14 | COOH | $CH_2$ | J1 | 0 | CH |
| 372 | Me | Me | A14 | COOH | $CH_2CH_2$ | J1 | 0 | CH |

TABLE 15-continued

| Compound No. | R¹ | R² | A | E | G | J | m | X |
|---|---|---|---|---|---|---|---|---|
| 373 | Me | Me | A15 | COOH | $CH_2$ | J1 | 0 | CH |
| 374 | Me | Me | A15 | COOH | $CH_2CH_2$ | J1 | 0 | CH |
| 375 | Me | Me | A16 | COOH | $CH_2$ | J1 | 0 | CH |

TABLE 16

| Compound No. | R¹ | R² | A | E | G | J | m | X |
|---|---|---|---|---|---|---|---|---|
| 376 | Me | Me | A16 | COOH | $CH_2CH_2$ | J1 | 0 | CH |
| 377 | Me | Me | A16 | COOH | $CH_2$ | J37 | 0 | CH |
| 378 | Me | Me | A16 | COOH | $CH_2$ | J39 | 0 | CH |
| 379 | Me | Me | A16 | COOH | $CH_2$ | J50 | 0 | CH |
| 380 | Me | Me | A16 | COOH | $CH_2$ | J63 | 0 | CH |
| 381 | Me | Me | A16 | COOH | $CH_2$ | J64 | 0 | CH |
| 382 | Me | Me | A16 | COOH | $CH_2$ | J65 | 0 | CH |
| 383 | H | H | A16 | COOH | $CH_2$ | J37 | 0 | CH |
| 384 | H | H | A16 | COOH | $CH_2$ | J39 | 0 | CH |
| 385 | H | H | A16 | COOH | $CH_2$ | J50 | 0 | CH |
| 386 | H | H | A16 | COOH | $CH_2$ | J63 | 0 | CH |
| 387 | H | H | A16 | COOH | $CH_2$ | J64 | 0 | CH |
| 388 | H | H | A16 | COOH | $CH_2$ | J65 | 0 | CH |
| 389 | Me | Me | A17 | COOH | $CH_2$ | J1 | 0 | CH |
| 390 | Me | Me | A17 | COOH | $CH_2CH_2$ | J1 | 0 | CH |
| 391 | Me | Me | A18 | COOH | $CH_2CH_2$ | J1 | 0 | CH |
| 392 | Me | Me | A18 | COOH | $CH_2$ | J37 | 0 | CH |
| 393 | Me | Me | A18 | COOH | $CH_2$ | J39 | 0 | CH |
| 394 | Me | Me | A18 | COOH | $CH_2$ | J50 | 0 | CH |
| 395 | Me | Me | A18 | COOH | $CH_2$ | J63 | 0 | CH |
| 396 | Me | Me | A18 | COOH | $CH_2$ | J64 | 0 | CH |
| 397 | Me | Me | A18 | COOH | $CH_2$ | J65 | 0 | CH |
| 398 | H | H | A18 | COOH | $CH_2$ | J37 | 0 | CH |
| 399 | H | H | A18 | COOH | $CH_2$ | J39 | 0 | CH |
| 400 | H | H | A18 | COOH | $CH_2$ | J50 | 0 | CH |

TABLE 17

| Compound No. | R¹ | R² | A | E | G | J | m | X |
|---|---|---|---|---|---|---|---|---|
| 401 | H | H | A18 | COOH | $CH_2$ | J63 | 0 | CH |
| 402 | H | H | A18 | COOH | $CH_2$ | J64 | 0 | CH |
| 403 | H | H | A18 | COOH | $CH_2$ | J65 | 0 | CH |
| 404 | Cl | Cl | A18 | COOH | $CH_2$ | J37 | 0 | CH |
| 405 | Cl | Cl | A18 | COOH | $CH_2$ | J63 | 0 | CH |
| 406 | Cl | Cl | A18 | COOH | $CH_2$ | J64 | 0 | CH |
| 407 | Cl | Cl | A18 | COOH | $CH_2$ | J65 | 0 | CH |
| 408 | H | H | A18 | COOH | $CH_2$ | J37 | 0 | N |
| 409 | H | H | A18 | COOH | $CH_2$ | J39 | 0 | N |
| 410 | H | H | A18 | COOH | $CH_2$ | J63 | 0 | N |
| 411 | H | H | A18 | COOH | $CH_2$ | J64 | 0 | N |
| 412 | H | H | A18 | COOH | $CH_2$ | J65 | 0 | N |
| 413 | Me | H | A18 | COOH | $CH_2$ | J37 | 0 | CH |
| 414 | Me | H | A18 | COOH | $CH_2$ | J39 | 0 | CH |
| 415 | Me | H | A18 | COOH | $CH_2$ | J63 | 0 | CH |
| 416 | Me | H | A18 | COOH | $CH_2$ | J64 | 0 | CH |
| 417 | Me | H | A18 | COOH | $CH_2$ | J65 | 0 | CH |
| 418 | OMe | H | A18 | COOH | $CH_2$ | J37 | 0 | CH |
| 419 | OMe | H | A18 | COOH | $CH_2$ | J39 | 0 | CH |
| 420 | OMe | H | A18 | COOH | $CH_2$ | J63 | 0 | CH |
| 421 | OMe | H | A18 | COOH | $CH_2$ | J64 | 0 | CH |
| 422 | OMe | H | A18 | COOH | $CH_2$ | J65 | 0 | CH |
| 423 | OEt | H | A18 | COOH | $CH_2$ | J63 | 0 | CH |
| 424 | OEt | H | A18 | COOH | $CH_2$ | J64 | 0 | CH |
| 425 | OEt | H | A18 | COOH | $CH_2$ | J65 | 0 | CH |

TABLE 18

| Compound No. | R¹ | R² | A | E | G | J | m | X |
|---|---|---|---|---|---|---|---|---|
| 426 | CF3 | H | A18 | COOH | $CH_2$ | J63 | 0 | CH |
| 427 | CF3 | H | A18 | COOH | $CH_2$ | J64 | 0 | CH |

TABLE 18-continued

| Compound No. | R¹ | R² | A | E | G | J | m | X |
|---|---|---|---|---|---|---|---|---|
| 428 | CF3 | H | A18 | COOH | CH₂ | J65 | 0 | CH |
| 429 | CN | H | A18 | COOH | CH₂ | J63 | 0 | CH |
| 430 | CN | H | A18 | COOH | CH₂ | J64 | 0 | CH |
| 431 | CN | H | A18 | COOH | CH₂ | J65 | 0 | CH |
| 432 | F | H | A18 | COOH | CH₂ | J63 | 0 | CH |
| 433 | F | H | A18 | COOH | CH₂ | J64 | 0 | CH |
| 434 | F | H | A18 | COOH | CH₂ | J65 | 0 | CH |
| 435 | Cl | H | A18 | COOH | CH₂ | J63 | 0 | N |
| 436 | Cl | H | A18 | COOH | CH₂ | J64 | 0 | N |
| 437 | Cl | H | A18 | COOH | CH₂ | J65 | 0 | N |
| 438 | H | H | A18 | COOH | CH₂ | J37 | 0 | N |
| 439 | Me | Me | A19 | COOH | CH₂ | J1 | 0 | CH |
| 440 | Me | Me | A19 | COOH | CH₂CH₂ | J1 | 0 | CH |
| 441 | Me | Me | A19 | COOH | CH₂ | J37 | 0 | CH |
| 442 | Me | Me | A19 | COOH | CH₂ | J39 | 0 | CH |
| 443 | Me | Me | A19 | COOH | CH₂ | J50 | 0 | CH |
| 444 | Me | Me | A19 | COOH | CH₂ | J63 | 0 | CH |
| 445 | Me | Me | A19 | COOH | CH₂ | J64 | 0 | CH |
| 446 | Me | Me | A19 | COOH | CH₂ | J65 | 0 | CH |
| 447 | H | H | A19 | COOH | CH₂ | J1 | 0 | CH |
| 448 | H | H | A19 | COOH | CH₂CH₂ | J1 | 0 | CH |
| 449 | H | H | A19 | COOH | CH₂ | J37 | 0 | CH |
| 450 | H | H | A19 | COOH | CH₂ | J39 | 0 | CH |

TABLE 19

| Compound No. | R¹ | R² | A | E | G | J | m | X |
|---|---|---|---|---|---|---|---|---|
| 451 | H | H | A19 | COOH | CH₂ | J50 | 0 | CH |
| 452 | H | H | A19 | COOH | CH₂ | J63 | 0 | CH |
| 453 | H | H | A19 | COOH | CH₂ | J64 | 0 | CH |
| 454 | H | H | A19 | COOH | CH₂ | J65 | 0 | CH |
| 455 | Me | Me | A20 | COOH | CH₂ | J64 | 0 | CH |
| 456 | Me | Me | A20 | COOH | CH₂ | J65 | 0 | CH |
| 457 | Me | Me | A20 | COOH | CH₂ | J67 | 0 | CH |
| 458 | Me | Me | A20 | COOH | CH₂ | J71 | 0 | CH |
| 459 | H | H | A20 | COOH | CH₂ | J64 | 0 | CH |
| 460 | H | H | A20 | COOH | CH₂ | J65 | 0 | CH |
| 461 | H | H | A20 | COOH | CH₂ | J67 | 0 | CH |
| 462 | H | H | A20 | COOH | CH₂ | J71 | 0 | CH |
| 463 | Cl | Cl | A20 | COOH | CH₂ | J64 | 0 | CH |
| 464 | Cl | Cl | A20 | COOH | CH₂ | J65 | 0 | CH |
| 465 | Cl | Cl | A20 | COOH | CH₂ | J67 | 0 | CH |
| 466 | Cl | Cl | A20 | COOH | CH₂ | J71 | 0 | CH |
| 467 | H | H | A20 | COOH | CH₂ | J64 | 0 | N |
| 468 | H | H | A20 | COOH | CH₂ | J65 | 0 | N |
| 469 | H | H | A20 | COOH | CH₂ | J67 | 0 | N |
| 470 | H | H | A20 | COOH | CH₂ | J71 | 0 | N |
| 471 | Me | H | A20 | COOH | CH₂ | J64 | 0 | CH |
| 472 | Me | H | A20 | COOH | CH₂ | J65 | 0 | CH |
| 473 | Me | H | A20 | COOH | CH₂ | J67 | 0 | CH |
| 474 | Me | H | A20 | COOH | CH₂ | J71 | 0 | CH |
| 475 | OMe | H | A20 | COOH | CH₂ | J64 | 0 | CH |

TABLE 20

| Compound No. | R¹ | R² | A | E | G | J | m | X |
|---|---|---|---|---|---|---|---|---|
| 476 | OMe | H | A20 | COOH | CH₂ | J65 | 0 | CH |
| 477 | OMe | H | A20 | COOH | CH₂ | J67 | 0 | CH |
| 478 | OMe | H | A20 | COOH | CH₂ | J71 | 0 | CH |
| 479 | OEt | H | A20 | COOH | CH₂ | J64 | 0 | CH |
| 480 | OEt | H | A20 | COOH | CH₂ | J65 | 0 | CH |
| 481 | OEt | H | A20 | COOH | CH₂ | J67 | 0 | CH |
| 482 | OEt | H | A20 | COOH | CH₂ | J71 | 0 | CH |
| 483 | F | H | A20 | COOH | CH₂ | J64 | 0 | CH |
| 484 | F | H | A20 | COOH | CH₂ | J65 | 0 | CH |
| 485 | F | H | A20 | COOH | CH₂ | J67 | 0 | CH |
| 486 | F | H | A20 | COOH | CH₂ | J71 | 0 | CH |
| 487 | CF3 | H | A20 | COOH | CH₂ | J64 | 0 | CH |
| 488 | CF3 | H | A20 | COOH | CH₂ | J65 | 0 | CH |
| 489 | CF3 | H | A20 | COOH | CH₂ | J67 | 0 | CH |

TABLE 20-continued

| Compound No. | R¹ | R² | A | E | G | J | m | X |
|---|---|---|---|---|---|---|---|---|
| 490 | CF3 | H | A20 | COOH | CH₂ | J71 | 0 | CH |
| 491 | CN | H | A20 | COOH | CH₂ | J64 | 0 | CH |
| 492 | CN | H | A20 | COOH | CH₂ | J65 | 0 | CH |
| 493 | CN | H | A20 | COOH | CH₂ | J67 | 0 | CH |
| 494 | CN | H | A20 | COOH | CH₂ | J71 | 0 | CH |
| 495 | Cl | H | A20 | COOH | CH₂ | J64 | 0 | N |
| 496 | Cl | H | A20 | COOH | CH₂ | J65 | 0 | N |
| 497 | Cl | H | A20 | COOH | CH₂ | J67 | 0 | N |
| 498 | Cl | H | A20 | COOH | CH₂ | J71 | 0 | N |
| 499 | H | H | A21 | COOH | CH₂ | J63 | 0 | CH |
| 500 | H | H | A21 | COOH | CH₂ | J65 | 0 | CH |

TABLE 21

| Compound No. | R¹ | R² | A | E | G | J | m | X |
|---|---|---|---|---|---|---|---|---|
| 501 | Me | Me | A1 | COOH | CH₂CH₂ | J1 | 0 | CH |
| 502 | Me | Me | A1 | COOH | CH₂CH₂ | J37 | 0 | CH |
| 503 | Me | Me | A1 | COOH | CH₂CH₂ | J39 | 0 | CH |
| 504 | Me | Me | A1 | COOH | CH₂CH₂ | J50 | 0 | CH |
| 505 | Me | Me | A1 | COOH | CH₂CH₂ | J62 | 0 | CH |
| 506 | Me | Me | A1 | COOH | CH₂CH₂ | J63 | 0 | CH |
| 507 | Me | Me | A1 | COOH | CH₂CH₂ | J64 | 0 | CH |
| 508 | Me | Me | A1 | COOH | CH₂CH₂ | J65 | 0 | CH |
| 509 | H | H | A1 | COOH | CH₂CH₂ | J1 | 0 | CH |
| 510 | H | H | A1 | COOH | CH₂CH₂ | J37 | 0 | CH |
| 511 | H | H | A1 | COOH | CH₂CH₂ | J39 | 0 | CH |
| 512 | H | H | A1 | COOH | CH₂CH₂ | J50 | 0 | CH |
| 513 | H | H | A1 | COOH | CH₂CH₂ | J62 | 0 | CH |
| 514 | H | H | A1 | COOH | CH₂CH₂ | J63 | 0 | CH |
| 515 | H | H | A1 | COOH | CH₂CH₂ | J64 | 0 | CH |
| 516 | H | H | A1 | COOH | CH₂CH₂ | J65 | 0 | CH |
| 517 | Me | Me | A4 | COOH | CH₂CH₂ | J37 | 0 | CH |
| 518 | Me | Me | A4 | COOH | CH₂CH₂ | J39 | 0 | CH |
| 519 | Me | Me | A4 | COOH | CH₂CH₂ | J67 | 0 | CH |
| 520 | Me | Me | A4 | COOH | CH₂CH₂ | J64 | 0 | CH |
| 521 | Me | Me | A4 | COOH | CH₂CH₂ | J65 | 0 | CH |
| 522 | H | H | A4 | COOH | CH₂CH₂ | J37 | 0 | CH |
| 523 | H | H | A4 | COOH | CH₂CH₂ | J39 | 0 | CH |
| 524 | H | H | A4 | COOH | CH₂CH₂ | J63 | 0 | CH |
| 525 | H | H | A4 | COOH | CH₂CH₂ | J64 | 0 | CH |

TABLE 22

| Compound No. | R¹ | R² | A | E | G | J | m | X |
|---|---|---|---|---|---|---|---|---|
| 526 | H | H | A4 | COOH | CH₂CH₂ | J65 | 0 | CH |
| 527 | H | H | A11 | COOH | CH₂CH₂ | J37 | 0 | CH |
| 528 | H | H | A11 | COOH | CH₂CH₂ | J39 | 0 | CH |
| 529 | H | H | A11 | COOH | CH₂CH₂ | J63 | 0 | CH |
| 530 | H | H | A11 | COOH | CH₂CH₂ | J64 | 0 | CH |
| 531 | H | H | A11 | COOH | CH₂CH₂ | J65 | 0 | CH |
| 532 | H | H | A18 | COOH | CH₂CH₂ | J37 | 0 | CH |
| 533 | H | H | A18 | COOH | CH₂CH₂ | J39 | 0 | CH |
| 534 | H | H | A18 | COOH | CH₂CH₂ | J63 | 0 | CH |
| 535 | H | H | A18 | COOH | CH₂CH₂ | J64 | 0 | CH |
| 536 | H | H | A18 | COOH | CH₂CH₂ | J65 | 0 | CH |
| 537 | Me | Me | A20 | COOH | CH₂CH₂ | J37 | 0 | CH |
| 538 | Me | Me | A20 | COOH | CH₂CH₂ | J39 | 0 | CH |
| 539 | Me | Me | A20 | COOH | CH₂CH₂ | J63 | 0 | CH |
| 540 | Me | Me | A20 | COOH | CH₂CH₂ | J64 | 0 | CH |
| 541 | Me | Me | A20 | COOH | CH₂CH₂ | J65 | 0 | CH |
| 542 | H | H | A20 | COOH | CH₂CH₂ | J37 | 0 | CH |
| 543 | H | H | A20 | COOH | CH₂CH₂ | J39 | 0 | CH |
| 544 | H | H | A20 | COOH | CH₂CH₂ | J63 | 0 | CH |
| 545 | H | H | A20 | COOH | CH₂CH₂ | J64 | 0 | CH |
| 546 | H | H | A20 | COOH | CH₂CH₂ | J65 | 0 | CH |
| 547 | Me | Me | A1 | COOH | CO | J1 | 0 | CH |
| 548 | Me | Me | A1 | COOH | CO | J63 | 0 | CH |

TABLE 22-continued

| Compound No. | R¹ | R² | A | E | G | J | m | X |
|---|---|---|---|---|---|---|---|---|
| 549 | H | H | A1 | COOH | CO | J1 | 0 | CH |
| 550 | H | H | A1 | COOH | CO | J63 | 0 | CH |

TABLE 23

| Compound No. | R¹ | R² | A | E | G | J | m | X |
|---|---|---|---|---|---|---|---|---|
| 551 | Me | Me | A4 | COOH | CO | J1 | 0 | CH |
| 552 | Me | Me | A4 | COOH | CO | J63 | 0 | CH |
| 553 | H | H | A4 | COOH | CO | J1 | 0 | CH |
| 554 | H | H | A4 | COOH | CO | J63 | 0 | CH |
| 555 | H | H | A11 | COOH | CO | J1 | 0 | CH |
| 556 | H | H | A11 | COOH | CO | J63 | 0 | CH |
| 557 | H | H | A18 | COOH | CO | J1 | 0 | CH |
| 558 | H | H | A18 | COOH | CO | J63 | 0 | CH |
| 559 | H | H | A20 | COOH | CO | J1 | 0 | CH |
| 560 | H | H | A20 | COOH | CO | J63 | 0 | CH |
| 561 | Me | Me | A1 | COOH | SO$_2$ | J1 | 0 | CH |
| 562 | Me | Me | A1 | COOH | SO$_2$ | J63 | 0 | CH |
| 563 | H | H | A1 | COOH | SO$_2$ | J1 | 0 | CH |
| 564 | H | H | A1 | COOH | SO$_2$ | J63 | 0 | CH |
| 565 | H | H | A4 | COOH | SO$_2$ | J1 | 0 | CH |
| 566 | H | H | A4 | COOH | SO$_2$ | J63 | 0 | CH |
| 567 | H | H | A11 | COOH | SO$_2$ | J1 | 0 | CH |
| 568 | H | H | A11 | COOH | SO$_2$ | J63 | 0 | CH |
| 569 | H | H | A18 | COOH | SO$_2$ | J1 | 0 | CH |
| 570 | H | H | A18 | COOH | SO$_2$ | J63 | 0 | CH |
| 571 | H | H | A20 | COOH | SO$_2$ | J1 | 0 | CH |
| 572 | H | H | A20 | COOH | SO$_2$ | J63 | 0 | CH |
| 573 | H | H | A1 | COOH | CH$_2$CO | J1 | 0 | CH |
| 574 | H | H | A1 | COOH | CH$_2$CO | J2 | 0 | CH |
| 575 | H | H | A1 | COOH | CH$_2$CO | J3 | 0 | CH |

TABLE 24

| Compound No. | R¹ | R² | A | E | G | J | m | X |
|---|---|---|---|---|---|---|---|---|
| 576 | H | H | A1 | COOH | CH$_2$CO | J4 | 0 | CH |
| 577 | H | H | A1 | COOH | CH$_2$CO | J5 | 0 | CH |
| 578 | H | H | A1 | COOH | CH$_2$CO | J6 | 0 | CH |
| 579 | H | H | A1 | COOH | CH$_2$CO | J7 | 0 | CH |
| 580 | H | H | A1 | COOH | CH$_2$CO | J8 | 0 | CH |
| 581 | H | H | A1 | COOH | CH$_2$CO | J9 | 0 | CH |
| 582 | H | H | A1 | COOH | CH$_2$CO | J10 | 0 | CH |
| 583 | H | H | A1 | COOH | CH$_2$CO | J11 | 0 | CH |
| 584 | H | H | A1 | COOH | CH$_2$CO | J12 | 0 | CH |
| 585 | H | H | A1 | COOH | CH$_2$CO | J13 | 0 | CH |
| 586 | H | H | A1 | COOH | CH$_2$CO | J17 | 0 | CH |
| 587 | H | H | A1 | COOH | CH$_2$CO | J18 | 0 | CH |
| 588 | H | H | A1 | COOH | CH$_2$CO | J19 | 0 | CH |
| 589 | H | H | A1 | COOH | CH$_2$CO | J23 | 0 | CH |
| 590 | H | H | A1 | COOH | CH$_2$CO | J24 | 0 | CH |
| 591 | H | H | A1 | COOH | CH$_2$CO | J25 | 0 | CH |
| 592 | H | H | A1 | COOH | CH$_2$CO | J36 | 0 | CH |
| 593 | H | H | A1 | COOH | CH$_2$CO | J47 | 0 | CH |
| 594 | H | H | A1 | COOH | CH$_2$CO | J57 | 0 | CH |
| 595 | H | H | A1 | COOH | CH$_2$CO | J62 | 0 | CH |
| 596 | Me | Me | A1 | COOH | CH$_2$CO | J1 | 0 | CH |
| 597 | Me | Me | A1 | COOH | CH$_2$CO | J2 | 0 | CH |
| 598 | Me | Me | A1 | COOH | CH$_2$CO | J3 | 0 | CH |
| 599 | Me | Me | A1 | COOH | CH$_2$CO | J4 | 0 | CH |
| 600 | Me | Me | A1 | COOH | CH$_2$CO | J5 | 0 | CH |

TABLE 25

| Compound No. | R¹ | R² | A | E | G | J | m | X |
|---|---|---|---|---|---|---|---|---|
| 601 | Me | Me | A1 | COOH | CH$_2$CO | J6 | 0 | CH |
| 602 | Me | Me | A1 | COOH | CH$_2$CO | J7 | 0 | CH |
| 603 | Me | Me | A1 | COOH | CH$_2$CO | J8 | 0 | CH |
| 604 | Me | Me | A1 | COOH | CH$_2$CO | J9 | 0 | CH |
| 605 | Me | Me | A1 | COOH | CH$_2$CO | J10 | 0 | CH |
| 606 | Me | Me | A1 | COOH | CH$_2$CO | J11 | 0 | CH |
| 607 | Me | Me | A1 | COOH | CH$_2$CO | J12 | 0 | CH |
| 608 | Me | Me | A1 | COOH | CH$_2$CO | J13 | 0 | CH |
| 609 | Me | Me | A1 | COOH | CH$_2$CO | J17 | 0 | CH |
| 610 | Me | Me | A1 | COOH | CH$_2$CO | J18 | 0 | CH |
| 611 | Me | Me | A1 | COOH | CH$_2$CO | J19 | 0 | CH |
| 612 | Me | Me | A1 | COOH | CH$_2$CO | J23 | 0 | CH |
| 613 | Me | Me | A1 | COOH | CH$_2$CO | J24 | 0 | CH |
| 614 | Me | Me | A1 | COOH | CH$_2$CO | J25 | 0 | CH |
| 615 | Me | Me | A1 | COOH | CH$_2$CO | J36 | 0 | CH |
| 616 | Me | Me | A1 | COOH | CH$_2$CO | J47 | 0 | CH |
| 617 | Me | Me | A1 | COOH | CH$_2$CO | J57 | 0 | CH |
| 618 | Me | Me | A1 | COOH | CH$_2$CO | J62 | 0 | CH |
| 619 | H | H | A1 | COOH | CH$_2$CONH | J1 | 0 | CH |
| 620 | H | H | A1 | COOH | CH$_2$CONH | J2 | 0 | CH |
| 621 | H | H | A1 | COOH | CH$_2$CONH | J3 | 0 | CH |
| 622 | H | H | A1 | COOH | CH$_2$CONH | J4 | 0 | CH |
| 623 | H | H | A1 | COOH | CH$_2$CONH | J5 | 0 | CH |
| 624 | H | H | A1 | COOH | CH$_2$CONH | J6 | 0 | CH |
| 625 | H | H | A1 | COOH | CH$_2$CONH | J7 | 0 | CH |

TABLE 26

| Compound No. | R¹ | R² | A | E | G | J | m | X |
|---|---|---|---|---|---|---|---|---|
| 626 | H | H | A1 | COOH | CH$_2$CONH | J8 | 0 | CH |
| 627 | H | H | A1 | COOH | CH$_2$CONH | J9 | 0 | CH |
| 628 | H | H | A1 | COOH | CH$_2$CONH | J10 | 0 | CH |
| 629 | H | H | A1 | COOH | CH$_2$CONH | J11 | 0 | CH |
| 630 | H | H | A1 | COOH | CH$_2$CONH | J12 | 0 | CH |
| 631 | H | H | A1 | COOH | CH$_2$CONH | J13 | 0 | CH |
| 632 | H | H | A1 | COOH | CH$_2$CONH | J14 | 0 | CH |
| 633 | H | H | A1 | COOH | CH$_2$CONH | J15 | 0 | CH |
| 634 | H | H | A1 | COOH | CH$_2$CONH | J16 | 0 | CH |
| 635 | H | H | A1 | COOH | CH$_2$CONH | J17 | 0 | CH |
| 636 | H | H | A1 | COOH | CH$_2$CONH | J18 | 0 | CH |
| 637 | H | H | A1 | COOH | CH$_2$CONH | J19 | 0 | CH |
| 638 | H | H | A1 | COOH | CH$_2$CONH | J20 | 0 | CH |
| 639 | H | H | A1 | COOH | CH$_2$CONH | J21 | 0 | CH |
| 640 | H | H | A1 | COOH | CH$_2$CONH | J22 | 0 | CH |
| 641 | H | H | A1 | COOH | CH$_2$CONH | J23 | 0 | CH |
| 642 | H | H | A1 | COOH | CH$_2$CONH | J24 | 0 | CH |
| 643 | H | H | A1 | COOH | CH$_2$CONH | J25 | 0 | CH |
| 644 | H | H | A1 | COOH | CH$_2$CONH | J26 | 0 | CH |
| 645 | H | H | A1 | COOH | CH$_2$CONH | J27 | 0 | CH |
| 646 | H | H | A1 | COOH | CH$_2$CONH | J28 | 0 | CH |
| 647 | H | H | A1 | COOH | CH$_2$CONH | J29 | 0 | CH |
| 648 | H | H | A1 | COOH | CH$_2$CONH | J30 | 0 | CH |
| 649 | H | H | A1 | COOH | CH$_2$CONH | J31 | 0 | CH |
| 650 | H | H | A1 | COOH | CH$_2$CONH | J32 | 0 | CH |

TABLE 27

| Compound No. | R¹ | R² | A | E | G | J | m | X |
|---|---|---|---|---|---|---|---|---|
| 651 | H | H | A1 | COOH | CH$_2$CONH | J33 | 0 | CH |
| 652 | H | H | A1 | COOH | CH$_2$CONH | J34 | 0 | CH |
| 653 | H | H | A1 | COOH | CH$_2$CONH | J35 | 0 | CH |
| 654 | H | H | A1 | COOH | CH$_2$CONH | J37 | 0 | CH |
| 655 | H | H | A1 | COOH | CH$_2$CONH | J39 | 0 | CH |
| 656 | H | H | A1 | COOH | CH$_2$CONH | J62 | 0 | CH |
| 657 | H | H | A1 | COOH | CH$_2$CONH | J63 | 0 | CH |
| 658 | Me | Me | A1 | COOH | CH$_2$CONH | J1 | 0 | CH |
| 659 | Me | Me | A1 | COOH | CH$_2$CONH | J2 | 0 | CH |

TABLE 27-continued

| Compound No. | R¹ | R² | A | E | G | J | m | X |
|---|---|---|---|---|---|---|---|---|
| 660 | Me | Me | A1 | COOH | $CH_2CONH$ | J3 | 0 | CH |
| 661 | Me | Me | A1 | COOH | $CH_2CONH$ | J4 | 0 | CH |
| 662 | Me | Me | A1 | COOH | $CH_2CONH$ | J5 | 0 | CH |
| 663 | Me | Me | A1 | COOH | $CH_2CONH$ | J6 | 0 | CH |
| 664 | Me | Me | A1 | COOH | $CH_2CONH$ | J7 | 0 | CH |
| 665 | Me | Me | A1 | COOH | $CH_2CONH$ | J8 | 0 | CH |
| 666 | Me | Me | A1 | COOH | $CH_2CONH$ | J9 | 0 | CH |
| 667 | Me | Me | A1 | COOH | $CH_2CONH$ | J10 | 0 | CH |
| 668 | Me | Me | A1 | COOH | $CH_2CONH$ | J11 | 0 | CH |
| 669 | Me | Me | A1 | COOH | $CH_2CONH$ | J12 | 0 | CH |
| 670 | Me | Me | A1 | COOH | $CH_2CONH$ | J13 | 0 | CH |
| 671 | Me | Me | A1 | COOH | $CH_2CONH$ | J14 | 0 | CH |
| 672 | Me | Me | A1 | COOH | $CH_2CONH$ | J15 | 0 | CH |
| 673 | Me | Me | A1 | COOH | $CH_2CONH$ | J16 | 0 | CH |
| 674 | Me | Me | A1 | COOH | $CH_2CONH$ | J17 | 0 | CH |
| 675 | Me | Me | A1 | COOH | $CH_2CONH$ | J18 | 0 | CH |

TABLE 28

| Compound No. | R¹ | R² | A | E | G | J | m | X |
|---|---|---|---|---|---|---|---|---|
| 676 | Me | Me | A1 | COOH | $CH_2CONH$ | J19 | 0 | CH |
| 677 | Me | Me | A1 | COOH | $CH_2CONH$ | J20 | 0 | CH |
| 678 | Me | Me | A1 | COOH | $CH_2CONH$ | J21 | 0 | CH |
| 679 | Me | Me | A1 | COOH | $CH_2CONH$ | J22 | 0 | CH |
| 680 | Me | Me | A1 | COOH | $CH_2CONH$ | J23 | 0 | CH |
| 681 | Me | Me | A1 | COOH | $CH_2CONH$ | J24 | 0 | CH |
| 682 | Me | Me | A1 | COOH | $CH_2CONH$ | J25 | 0 | CH |
| 683 | Me | Me | A1 | COOH | $CH_2CONH$ | J26 | 0 | CH |
| 684 | Me | Me | A1 | COOH | $CH_2CONH$ | J27 | 0 | CH |
| 685 | Me | Me | A1 | COOH | $CH_2CONH$ | J28 | 0 | CH |
| 686 | Me | Me | A1 | COOH | $CH_2CONH$ | J29 | 0 | CH |
| 687 | Me | Me | A1 | COOH | $CH_2CONH$ | J30 | 0 | CH |
| 688 | Me | Me | A1 | COOH | $CH_2CONH$ | J31 | 0 | CH |
| 689 | Me | Me | A1 | COOH | $CH_2CONH$ | J32 | 0 | CH |
| 690 | Me | Me | A1 | COOH | $CH_2CONH$ | J33 | 0 | CH |
| 691 | Me | Me | A1 | COOH | $CH_2CONH$ | J34 | 0 | CH |
| 692 | Me | Me | A1 | COOH | $CH_2CONH$ | J35 | 0 | CH |
| 693 | Me | Me | A1 | COOH | $CH_2CONH$ | J37 | 0 | CH |
| 694 | Me | Me | A1 | COOH | $CH_2CONH$ | J39 | 0 | CH |
| 695 | Me | Me | A1 | COOH | $CH_2CONH$ | J62 | 0 | CH |
| 696 | Me | Me | A1 | COOH | $CH_2CONH$ | J63 | 0 | CH |
| 697 | H | H | A1 | COOH | $CH_2CH_2O$ | J1 | 0 | CH |
| 698 | H | H | A1 | COOH | $CH_2CH_2O$ | J2 | 0 | CH |
| 699 | H | H | A1 | COOH | $CH_2CH_2O$ | J3 | 0 | CH |
| 700 | H | H | A1 | COOH | $CH_2CH_2O$ | J4 | 0 | CH |

TABLE 29

| Compound No. | R¹ | R² | A | E | G | J | m | X |
|---|---|---|---|---|---|---|---|---|
| 701 | H | H | A1 | COOH | $CH_2CH_2O$ | J5 | 0 | CH |
| 702 | H | H | A1 | COOH | $CH_2CH_2O$ | J6 | 0 | CH |
| 703 | H | H | A1 | COOH | $CH_2CH_2O$ | J7 | 0 | CH |
| 704 | H | H | A1 | COOH | $CH_2CH_2O$ | J8 | 0 | CH |
| 705 | H | H | A1 | COOH | $CH_2CH_2O$ | J9 | 0 | CH |
| 706 | H | H | A1 | COOH | $CH_2CH_2O$ | J10 | 0 | CH |
| 707 | H | H | A1 | COOH | $CH_2CH_2O$ | J11 | 0 | CH |
| 708 | H | H | A1 | COOH | $CH_2CH_2O$ | J12 | 0 | CH |
| 709 | H | H | A1 | COOH | $CH_2CH_2O$ | J13 | 0 | CH |
| 710 | H | H | A1 | COOH | $CH_2CH_2O$ | J14 | 0 | CH |
| 711 | H | H | A1 | COOH | $CH_2CH_2O$ | J15 | 0 | CH |
| 712 | H | H | A1 | COOH | $CH_2CH_2O$ | J16 | 0 | CH |
| 713 | H | H | A1 | COOH | $CH_2CH_2O$ | J17 | 0 | CH |
| 714 | H | H | A1 | COOH | $CH_2CH_2O$ | J18 | 0 | CH |
| 715 | H | H | A1 | COOH | $CH_2CH_2O$ | J19 | 0 | CH |
| 716 | H | H | A1 | COOH | $CH_2CH_2O$ | J20 | 0 | CH |
| 717 | H | H | A1 | COOH | $CH_2CH_2O$ | J21 | 0 | CH |
| 718 | H | H | A1 | COOH | $CH_2CH_2O$ | J22 | 0 | CH |
| 719 | H | H | A1 | COOH | $CH_2CH_2O$ | J23 | 0 | CH |
| 720 | H | H | A1 | COOH | $CH_2CH_2O$ | J24 | 0 | CH |
| 721 | H | H | A1 | COOH | $CH_2CH_2O$ | J25 | 0 | CH |
| 722 | H | H | A1 | COOH | $CH_2CH_2O$ | J26 | 0 | CH |
| 723 | H | H | A1 | COOH | $CH_2CH_2O$ | J27 | 0 | CH |
| 724 | H | H | A1 | COOH | $CH_2CH_2O$ | J28 | 0 | CH |
| 725 | H | H | A1 | COOH | $CH_2CH_2O$ | J29 | 0 | CH |

TABLE 30

| Compound No. | R¹ | R² | A | E | G | J | m | X |
|---|---|---|---|---|---|---|---|---|
| 726 | H | H | A1 | COOH | $CH_2CH_2O$ | J30 | 0 | CH |
| 727 | H | H | A1 | COOH | $CH_2CH_2O$ | J31 | 0 | CH |
| 728 | H | H | A1 | COOH | $CH_2CH_2O$ | J32 | 0 | CH |
| 729 | H | H | A1 | COOH | $CH_2CH_2O$ | J33 | 0 | CH |
| 730 | H | H | A1 | COOH | $CH_2CH_2O$ | J34 | 0 | CH |
| 731 | H | H | A1 | COOH | $CH_2CH_2O$ | J35 | 0 | CH |
| 732 | H | H | A1 | COOH | $CH_2CH_2O$ | J37 | 0 | CH |
| 733 | H | H | A1 | COOH | $CH_2CH_2O$ | J39 | 0 | CH |
| 734 | H | H | A1 | COOH | $CH_2CH_2O$ | J62 | 0 | CH |
| 735 | H | H | A1 | COOH | $CH_2CH_2O$ | J63 | 0 | CH |
| 736 | Me | Me | A1 | COOH | $CH_2CH_2O$ | J1 | 0 | CH |
| 737 | Me | Me | A1 | COOH | $CH_2CH_2O$ | J2 | 0 | CH |
| 738 | Me | Me | A1 | COOH | $CH_2CH_2O$ | J3 | 0 | CH |
| 739 | Me | Me | A1 | COOH | $CH_2CH_2O$ | J4 | 0 | CH |
| 740 | Me | Me | A1 | COOH | $CH_2CH_2O$ | J5 | 0 | CH |
| 741 | Me | Me | A1 | COOH | $CH_2CH_2O$ | J6 | 0 | CH |
| 742 | Me | Me | A1 | COOH | $CH_2CH_2O$ | J7 | 0 | CH |
| 743 | Me | Me | A1 | COOH | $CH_2CH_2O$ | J8 | 0 | CH |
| 744 | Me | Me | A1 | COOH | $CH_2CH_2O$ | J9 | 0 | CH |
| 745 | Me | Me | A1 | COOH | $CH_2CH_2O$ | J10 | 0 | CH |
| 746 | Me | Me | A1 | COOH | $CH_2CH_2O$ | J11 | 0 | CH |
| 747 | Me | Me | A1 | COOH | $CH_2CH_2O$ | J12 | 0 | CH |
| 748 | Me | Me | A1 | COOH | $CH_2CH_2O$ | J13 | 0 | CH |
| 749 | Me | Me | A1 | COOH | $CH_2CH_2O$ | J14 | 0 | CH |
| 750 | Me | Me | A1 | COOH | $CH_2CH_2O$ | J15 | 0 | CH |

TABLE 31

| Compound No. | R¹ | R² | A | E | G | J | m | X |
|---|---|---|---|---|---|---|---|---|
| 751 | Me | Me | A1 | COOH | $CH_2CH_2O$ | J15 | 0 | CH |
| 752 | Me | Me | A1 | COOH | $CH_2CH_2O$ | J16 | 0 | CH |
| 753 | Me | Me | A1 | COOH | $CH_2CH_2O$ | J17 | 0 | CH |
| 754 | Me | Me | A1 | COOH | $CH_2CH_2O$ | J18 | 0 | CH |
| 755 | Me | Me | A1 | COOH | $CH_2CH_2O$ | J19 | 0 | CH |
| 756 | Me | Me | A1 | COOH | $CH_2CH_2O$ | J20 | 0 | CH |
| 757 | Me | Me | A1 | COOH | $CH_2CH_2O$ | J21 | 0 | CH |
| 758 | Me | Me | A1 | COOH | $CH_2CH_2O$ | J22 | 0 | CH |
| 759 | Me | Me | A1 | COOH | $CH_2CH_2O$ | J23 | 0 | CH |
| 760 | Me | Me | A1 | COOH | $CH_2CH_2O$ | J24 | 0 | CH |
| 761 | Me | Me | A1 | COOH | $CH_2CH_2O$ | J25 | 0 | CH |
| 762 | Me | Me | A1 | COOH | $CH_2CH_2O$ | J26 | 0 | CH |
| 763 | Me | Me | A1 | COOH | $CH_2CH_2O$ | J27 | 0 | CH |
| 764 | Me | Me | A1 | COOH | $CH_2CH_2O$ | J28 | 0 | CH |
| 765 | Me | Me | A1 | COOH | $CH_2CH_2O$ | J29 | 0 | CH |
| 766 | Me | Me | A1 | COOH | $CH_2CH_2O$ | J30 | 0 | CH |
| 767 | Me | Me | A1 | COOH | $CH_2CH_2O$ | J31 | 0 | CH |
| 768 | Me | Me | A1 | COOH | $CH_2CH_2O$ | J32 | 0 | CH |
| 769 | Me | Me | A1 | COOH | $CH_2CH_2O$ | J33 | 0 | CH |
| 770 | Me | Me | A1 | COOH | $CH_2CH_2O$ | J34 | 0 | CH |
| 771 | Me | Me | A1 | COOH | $CH_2CH_2O$ | J35 | 0 | CH |
| 772 | Me | Me | A1 | COOH | $CH_2CH_2O$ | J37 | 0 | CH |
| 773 | Me | Me | A1 | COOH | $CH_2CH_2O$ | J39 | 0 | CH |
| 774 | Me | Me | A1 | COOH | $CH_2CH_2O$ | J62 | 0 | CH |
| 775 | Me | Me | A1 | COOH | $CH_2CH_2O$ | J63 | 0 | CH |

TABLE 32

| Compound No. | R¹ | R² | A | E | G | J | m | X |
|---|---|---|---|---|---|---|---|---|
| 776 | H | H | A1 | COOH | CH₂S | J1 | 0 | CH |
| 777 | H | H | A1 | COOH | CH₂S | J2 | 0 | CH |
| 778 | H | H | A1 | COOH | CH₂S | J3 | 0 | CH |
| 779 | H | H | A1 | COOH | CH₂S | J4 | 0 | CH |
| 780 | H | H | A1 | COOH | CH₂S | J8 | 0 | CH |
| 781 | H | H | A1 | COOH | CH₂S | J9 | 0 | CH |
| 782 | H | H | A1 | COOH | CH₂S | J10 | 0 | CH |
| 783 | Me | Me | A1 | COOH | CH₂S | J1 | 0 | CH |
| 784 | Me | Me | A1 | COOH | CH₂S | J2 | 0 | CH |
| 785 | Me | Me | A1 | COOH | CH₂S | J3 | 0 | CH |
| 786 | Me | Me | A1 | COOH | CH₂S | J4 | 0 | CH |
| 787 | Me | Me | A1 | COOH | CH₂S | J8 | 0 | CH |
| 788 | Me | Me | A1 | COOH | CH₂S | J9 | 0 | CH |
| 789 | Me | Me | A1 | COOH | CH₂S | J10 | 0 | CH |
| 790 | H | H | A1 | COOH | CH₂SO₂ | J1 | 0 | CH |
| 791 | H | H | A1 | COOH | CH₂SO₂ | J2 | 0 | CH |
| 792 | H | H | A1 | COOH | CH₂SO₂ | J3 | 0 | CH |
| 793 | H | H | A1 | COOH | CH₂SO₂ | J4 | 0 | CH |
| 794 | H | H | A1 | COOH | CH₂SO₂ | J8 | 0 | CH |
| 795 | H | H | A1 | COOH | CH₂SO₂ | J9 | 0 | CH |
| 796 | H | H | A1 | COOH | CH₂SO₂ | J10 | 0 | CH |
| 797 | Me | Me | A1 | COOH | CH₂SO₂ | J1 | 0 | CH |
| 798 | Me | Me | A1 | COOH | CH₂SO₂ | J2 | 0 | CH |
| 799 | Me | Me | A1 | COOH | CH₂SO₂ | J3 | 0 | CH |
| 800 | Me | Me | A1 | COOH | CH₂SO₂ | J4 | 0 | CH |

TABLE 33

| Compound No. | R¹ | R² | A | E | G | J | m | X |
|---|---|---|---|---|---|---|---|---|
| 801 | Me | Me | A1 | COOH | CH₂SO₂ | J8 | 0 | CH |
| 802 | Me | Me | A1 | COOH | CH₂SO₂ | J9 | 0 | CH |
| 803 | Me | Me | A1 | COOH | CH₂SO₂ | J10 | 0 | CH |
| 804 | Me | Me | A1 | COOH | CH₂ | J81 | 0 | CH |
| 805 | Me | Me | A1 | COOH | CH₂ | J82 | 0 | CH |
| 806 | Me | Me | A1 | COOH | CH₂ | J83 | 0 | CH |
| 807 | Me | Me | A1 | COOH | CH₂ | J84 | 0 | CH |
| 808 | Me | Me | A1 | COOH | CH₂ | J85 | 0 | CH |
| 809 | H | H | A1 | COOH | CH₂ | J81 | 0 | CH |
| 810 | H | H | A1 | COOH | CH₂ | J82 | 0 | CH |
| 811 | H | H | A1 | COOH | CH₂ | J83 | 0 | CH |
| 812 | H | H | A1 | COOH | CH₂ | J84 | 0 | CH |
| 813 | H | H | A1 | COOH | CH₂ | J85 | 0 | CH |
| 814 | Me | Me | A1 | COOH | CH₂CH₂ | J1 | 1 | CH |
| 815 | Me | Me | A1 | COOH | CH₂ | J1 | 1 | CH |
| 816 | Me | Me | A1 | COOH | CH₂ | J37 | 1 | CH |
| 817 | Me | Me | A1 | COOH | CH₂ | J39 | 1 | CH |
| 818 | Me | Me | A1 | COOH | CH₂ | J50 | 1 | CH |
| 819 | Me | Me | A1 | COOH | CH₂ | J63 | 1 | CH |
| 820 | Me | Me | A1 | COOH | CH₂ | J64 | 1 | CH |
| 821 | Me | Me | A1 | COOH | CH₂ | J65 | 1 | CH |
| 822 | H | H | A1 | COOH | CH₂ | J37 | 1 | CH |
| 823 | H | H | A1 | COOH | CH₂ | J39 | 1 | CH |
| 824 | H | H | A1 | COOH | CH₂ | J50 | 1 | CH |
| 825 | H | H | A1 | COOH | CH₂ | J63 | 1 | CH |

TABLE 34

| Compound No. | R¹ | R² | A | E | G | J | m | X |
|---|---|---|---|---|---|---|---|---|
| 826 | H | H | A1 | COOH | CH₂ | J64 | 1 | CH |
| 827 | H | H | A1 | COOH | CH₂ | J65 | 1 | CH |
| 828 | Cl | Cl | A1 | COOH | CH₂ | J37 | 1 | CH |
| 829 | Cl | Cl | A1 | COOH | CH₂ | J39 | 1 | CH |
| 830 | Cl | Cl | A1 | COOH | CH₂ | J50 | 1 | CH |
| 831 | Cl | Cl | A1 | COOH | CH₂ | J63 | 1 | CH |
| 832 | Cl | Cl | A1 | COOH | CH₂ | J64 | 1 | CH |
| 833 | Cl | Cl | A1 | COOH | CH₂ | J65 | 1 | CH |
| 834 | H | H | A4 | COOH | CH₂ | J37 | 1 | CH |
| 835 | H | H | A4 | COOH | CH₂ | J39 | 1 | CH |
| 836 | H | H | A4 | COOH | CH₂ | J50 | 1 | CH |
| 837 | H | H | A4 | COOH | CH₂ | J63 | 1 | CH |
| 838 | H | H | A4 | COOH | CH₂ | J64 | 1 | CH |
| 839 | H | H | A4 | COOH | CH₂ | J65 | 1 | CH |
| 840 | H | H | A11 | COOH | CH₂ | J37 | 1 | CH |
| 841 | H | H | A11 | COOH | CH₂ | J39 | 1 | CH |
| 842 | H | H | A11 | COOH | CH₂ | J50 | 1 | CH |
| 843 | H | H | A11 | COOH | CH₂ | J63 | 1 | CH |
| 844 | H | H | A11 | COOH | CH₂ | J64 | 1 | CH |
| 845 | H | H | A11 | COOH | CH₂ | J65 | 1 | CH |
| 846 | H | H | A18 | COOH | CH₂ | J37 | 1 | CH |
| 847 | H | H | A18 | COOH | CH₂ | J39 | 1 | CH |
| 848 | H | H | A18 | COOH | CH₂ | J50 | 1 | CH |
| 849 | H | H | A18 | COOH | CH₂ | J63 | 1 | CH |
| 850 | H | H | A18 | COOH | CH₂ | J64 | 1 | CH |

TABLE 35

| Compound No. | R¹ | R² | A | E | G | J | m | X |
|---|---|---|---|---|---|---|---|---|
| 851 | H | H | A18 | COOH | CH₂ | J65 | 1 | CH |
| 852 | H | H | A20 | COOH | CH₂ | J37 | 1 | CH |
| 853 | H | H | A20 | COOH | CH₂ | J39 | 1 | CH |
| 854 | H | H | A20 | COOH | CH₂ | J50 | 1 | CH |
| 855 | H | H | A20 | COOH | CH₂ | J63 | 1 | CH |
| 856 | H | H | A20 | COOH | CH₂ | J64 | 1 | CH |
| 857 | H | H | A20 | COOH | CH₂ | J65 | 1 | CH |
| 858 | Me | Me | A1 | COOH | CH₂CH₂ | J1 | 2 | CH |
| 859 | Me | Me | A1 | COOH | CH₂ | J1 | 2 | CH |
| 860 | Me | Me | A1 | COOH | CH₂ | J37 | 2 | CH |
| 861 | Me | Me | A1 | COOH | CH₂ | J39 | 2 | CH |
| 862 | Me | Me | A1 | COOH | CH₂ | J50 | 2 | CH |
| 863 | Me | Me | A1 | COOH | CH₂ | J63 | 2 | CH |
| 864 | Me | Me | A1 | COOH | CH₂ | J64 | 2 | CH |
| 865 | Me | Me | A1 | COOH | CH₂ | J65 | 2 | CH |
| 866 | H | H | A1 | COOH | CH₂ | J37 | 2 | CH |
| 867 | H | H | A1 | COOH | CH₂ | J39 | 2 | CH |
| 868 | H | H | A1 | COOH | CH₂ | J50 | 2 | CH |
| 869 | H | H | A1 | COOH | CH₂ | J63 | 2 | CH |
| 870 | H | H | A1 | COOH | CH₂ | J64 | 2 | CH |
| 871 | H | H | A1 | COOH | CH₂ | J65 | 2 | CH |
| 872 | Cl | Cl | A1 | COOH | CH₂ | J37 | 2 | CH |
| 873 | Cl | Cl | A1 | COOH | CH₂ | J39 | 2 | CH |
| 874 | Cl | Cl | A1 | COOH | CH₂ | J50 | 2 | CH |
| 875 | Cl | Cl | A1 | COOH | CH₂ | J63 | 2 | CH |

TABLE 36

| Compound No. | R¹ | R² | A | E | G | J | m | X |
|---|---|---|---|---|---|---|---|---|
| 876 | Cl | Cl | A1 | COOH | CH₂ | J64 | 2 | CH |
| 877 | Cl | Cl | A1 | COOH | CH₂ | J65 | 2 | CH |
| 878 | H | H | A1 | COOH | CH₂ | J37 | 2 | N |
| 879 | H | H | A1 | COOH | CH₂ | J39 | 2 | N |
| 880 | H | H | A1 | COOH | CH₂ | J50 | 2 | N |
| 881 | H | H | A1 | COOH | CH₂ | J63 | 2 | N |
| 882 | H | H | A1 | COOH | CH₂ | J64 | 2 | N |
| 883 | H | H | A1 | COOH | CH₂ | J65 | 2 | N |
| 884 | Me | H | A1 | COOH | CH₂ | J37 | 2 | CH |
| 885 | Me | H | A1 | COOH | CH₂ | J63 | 2 | CH |
| 886 | Me | H | A1 | COOH | CH₂ | J64 | 2 | CH |
| 887 | Me | H | A1 | COOH | CH₂ | J65 | 2 | CH |
| 888 | H | H | A4 | COOH | CH₂ | J37 | 2 | CH |
| 889 | H | H | A4 | COOH | CH₂ | J63 | 2 | CH |
| 890 | H | H | A4 | COOH | CH₂ | J64 | 2 | CH |
| 891 | H | H | A4 | COOH | CH₂ | J65 | 2 | CH |
| 892 | Me | Me | A4 | COOH | CH₂ | J37 | 2 | CH |
| 893 | Me | Me | A4 | COOH | CH₂ | J63 | 2 | CH |
| 894 | Me | Me | A4 | COOH | CH₂ | J64 | 2 | CH |
| 895 | Me | Me | A4 | COOH | CH₂ | J65 | 2 | CH |
| 896 | Cl | Cl | A4 | COOH | CH₂ | J37 | 2 | CH |
| 897 | Cl | Cl | A4 | COOH | CH₂ | J63 | 2 | CH |
| 898 | Cl | Cl | A4 | COOH | CH₂ | J64 | 2 | CH |

TABLE 36-continued

| Compound No. | R¹ | R² | A | E | G | J | m | X |
|---|---|---|---|---|---|---|---|---|
| 899 | Cl | Cl | A4 | COOH | CH₂ | J65 | 2 | CH |
| 900 | H | H | A4 | COOH | CH₂ | J37 | 2 | N |

TABLE 37

| Compound No. | R¹ | R² | A | E | G | J | m | X |
|---|---|---|---|---|---|---|---|---|
| 901 | H | H | A4 | COOH | CH₂ | J63 | 2 | N |
| 902 | H | H | A4 | COOH | CH₂ | J64 | 2 | N |
| 903 | H | H | A4 | COOH | CH₂ | J65 | 2 | N |
| 904 | H | H | A11 | COOH | CH₂ | J37 | 2 | CH |
| 905 | H | H | A11 | COOH | CH₂ | J63 | 2 | CH |
| 906 | H | H | A11 | COOH | CH₂ | J64 | 2 | CH |
| 907 | H | H | A11 | COOH | CH₂ | J65 | 2 | CH |
| 908 | Me | Me | A11 | COOH | CH₂ | J37 | 2 | CH |
| 909 | Me | Me | A11 | COOH | CH₂ | J63 | 2 | CH |
| 910 | Me | Me | A11 | COOH | CH₂ | J64 | 2 | CH |
| 911 | Me | Me | A11 | COOH | CH₂ | J65 | 2 | CH |
| 912 | Cl | Cl | A11 | COOH | CH₂ | J37 | 2 | CH |
| 913 | Cl | Cl | A11 | COOH | CH₂ | J63 | 2 | CH |
| 914 | Cl | Cl | A11 | COOH | CH₂ | J64 | 2 | CH |
| 915 | Cl | Cl | A11 | COOH | CH₂ | J65 | 2 | CH |
| 916 | H | H | A11 | COOH | CH₂ | J37 | 2 | N |
| 917 | H | H | A11 | COOH | CH₂ | J63 | 2 | N |
| 918 | H | H | A11 | COOH | CH₂ | J64 | 2 | N |
| 919 | H | H | A11 | COOH | CH₂ | J65 | 2 | N |
| 920 | Me | Me | A18 | COOH | CH₂ | J37 | 2 | CH |
| 921 | Me | Me | A18 | COOH | CH₂ | J63 | 2 | CH |
| 922 | Me | Me | A18 | COOH | CH₂ | J64 | 2 | CH |
| 923 | Me | Me | A18 | COOH | CH₂ | J65 | 2 | CH |
| 924 | H | H | A18 | COOH | CH₂ | J37 | 2 | CH |
| 925 | H | H | A18 | COOH | CH₂ | J63 | 2 | CH |

TABLE 38

| Compound No. | R¹ | R² | A | E | G | J | m | X |
|---|---|---|---|---|---|---|---|---|
| 926 | H | H | A18 | COOH | CH₂ | J64 | 2 | CH |
| 927 | H | H | A18 | COOH | CH₂ | J65 | 2 | CH |
| 928 | Cl | Cl | A18 | COOH | CH₂ | J37 | 2 | CH |
| 929 | Cl | Cl | A18 | COOH | CH₂ | J63 | 2 | CH |
| 930 | Cl | Cl | A18 | COOH | CH₂ | J64 | 2 | CH |
| 931 | Cl | Cl | A18 | COOH | CH₂ | J65 | 2 | CH |
| 932 | H | H | A18 | COOH | CH₂ | J37 | 2 | N |
| 933 | H | H | A18 | COOH | CH₂ | J63 | 2 | N |
| 934 | H | H | A18 | COOH | CH₂ | J64 | 2 | N |
| 935 | H | H | A18 | COOH | CH₂ | J65 | 2 | N |
| 936 | Me | Me | A20 | COOH | CH₂ | J37 | 2 | CH |
| 937 | Me | Me | A20 | COOH | CH₂ | J63 | 2 | CH |
| 938 | Me | Me | A20 | COOH | CH₂ | J64 | 2 | CH |
| 939 | Me | Me | A20 | COOH | CH₂ | J65 | 2 | CH |
| 940 | H | H | A20 | COOH | CH₂ | J37 | 2 | CH |
| 941 | H | H | A20 | COOH | CH₂ | J63 | 2 | CH |
| 942 | H | H | A20 | COOH | CH₂ | J64 | 2 | CH |
| 943 | H | H | A20 | COOH | CH₂ | J65 | 2 | CH |
| 944 | Cl | Cl | A20 | COOH | CH₂ | J37 | 2 | CH |
| 945 | Cl | Cl | A20 | COOH | CH₂ | J63 | 2 | CH |
| 946 | Cl | Cl | A20 | COOH | CH₂ | J64 | 2 | CH |
| 947 | Cl | Cl | A20 | COOH | CH₂ | J65 | 2 | CH |
| 948 | H | H | A20 | COOH | CH₂ | J37 | 2 | N |
| 949 | H | H | A20 | COOH | CH₂ | J63 | 2 | N |
| 950 | H | H | A20 | COOH | CH₂ | J64 | 2 | N |

TABLE 39

| Compound No. | R¹ | R² | A | E | G | J | m | X |
|---|---|---|---|---|---|---|---|---|
| 951 | H | H | A20 | COOH | CH₂ | J65 | 2 | N |
| 952 | Me | Me | A1 | tetrazol | CH₂ | J37 | 0 | CH |
| 953 | Me | Me | A1 | tetrazol | CH₂ | J63 | 0 | CH |

TABLE 39-continued

| Compound No. | R¹ | R² | A | E | G | J | m | X |
|---|---|---|---|---|---|---|---|---|
| 954 | Me | Me | A1 | tetrazol | CH₂ | J64 | 0 | CH |
| 955 | Me | Me | A1 | tetrazol | CH₂ | J65 | 0 | CH |
| 956 | H | H | A1 | tetrazol | CH₂ | J37 | 0 | CH |
| 957 | H | H | A1 | tetrazol | CH₂ | J63 | 0 | CH |
| 958 | H | H | A1 | tetrazol | CH₂ | J64 | 0 | CH |
| 959 | H | H | A1 | tetrazol | CH₂ | J65 | 0 | CH |
| 960 | Cl | Cl | A1 | tetrazol | CH₂ | J37 | 0 | CH |
| 961 | Cl | Cl | A1 | tetrazol | CH₂ | J63 | 0 | CH |
| 962 | Cl | Cl | A1 | tetrazol | CH₂ | J64 | 0 | CH |
| 963 | Cl | Cl | A1 | tetrazol | CH₂ | J65 | 0 | CH |
| 964 | H | H | A1 | tetrazol | CH₂ | J37 | 0 | N |
| 965 | H | H | A1 | tetrazol | CH₂ | J63 | 0 | N |
| 966 | H | H | A1 | tetrazol | CH₂ | J64 | 0 | N |
| 967 | H | H | A1 | tetrazol | CH₂ | J65 | 0 | N |
| 968 | H | H | A4 | tetrazol | CH₂ | J37 | 0 | CH |
| 969 | H | H | A4 | tetrazol | CH₂ | J63 | 0 | CH |
| 970 | H | H | A4 | tetrazol | CH₂ | J64 | 0 | CH |
| 971 | H | H | A4 | tetrazol | CH₂ | J65 | 0 | CH |
| 972 | H | H | A18 | tetrazol | CH₂ | J37 | 0 | CH |
| 973 | H | H | A18 | tetrazol | CH₂ | J63 | 0 | CH |
| 974 | H | H | A18 | tetrazol | CH₂ | J64 | 0 | CH |
| 975 | H | H | A18 | tetrazol | CH₂ | J65 | 0 | CH |

TABLE 40

| Compound No. | R¹ | R² | A | E | G | J | m | X |
|---|---|---|---|---|---|---|---|---|
| 976 | Me | Me | A19 | tetrazol | CH₂ | J37 | 0 | CH |
| 977 | Me | Me | A19 | tetrazol | CH₂ | J63 | 0 | CH |
| 978 | Me | Me | A19 | tetrazol | CH₂ | J64 | 0 | CH |
| 979 | Me | Me | A19 | tetrazol | CH₂ | J65 | 0 | CH |
| 980 | H | H | A19 | tetrazol | CH₂ | J37 | 0 | CH |
| 981 | H | H | A19 | tetrazol | CH₂ | J63 | 0 | CH |
| 982 | H | H | A19 | tetrazol | CH₂ | J64 | 0 | CH |
| 983 | H | H | A19 | tetrazol | CH₂ | J65 | 0 | CH |
| 984 | Me | Me | A20 | tetrazol | CH₂ | J37 | 0 | CH |
| 985 | Me | Me | A20 | tetrazol | CH₂ | J63 | 0 | CH |
| 986 | Me | Me | A20 | tetrazol | CH₂ | J64 | 0 | CH |
| 987 | Me | Me | A20 | tetrazol | CH₂ | J65 | 0 | CH |
| 988 | H | H | A20 | tetrazol | CH₂ | J37 | 0 | CH |
| 989 | H | H | A20 | tetrazol | CH₂ | J63 | 0 | CH |
| 990 | H | H | A20 | tetrazol | CH₂ | J64 | 0 | CH |
| 991 | H | H | A20 | tetrazol | CH₂ | J65 | 0 | CH |

The thiobenzimidazole derivative (1) of the present invention in which E is COOH and m is 0 can be prepared by the synthetic method (A) or (B) shown below:

Synthetic method (A)

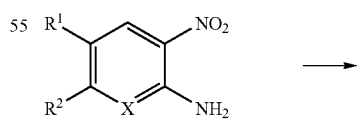

(a1)

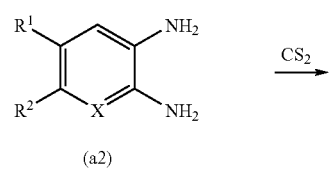

(a2)

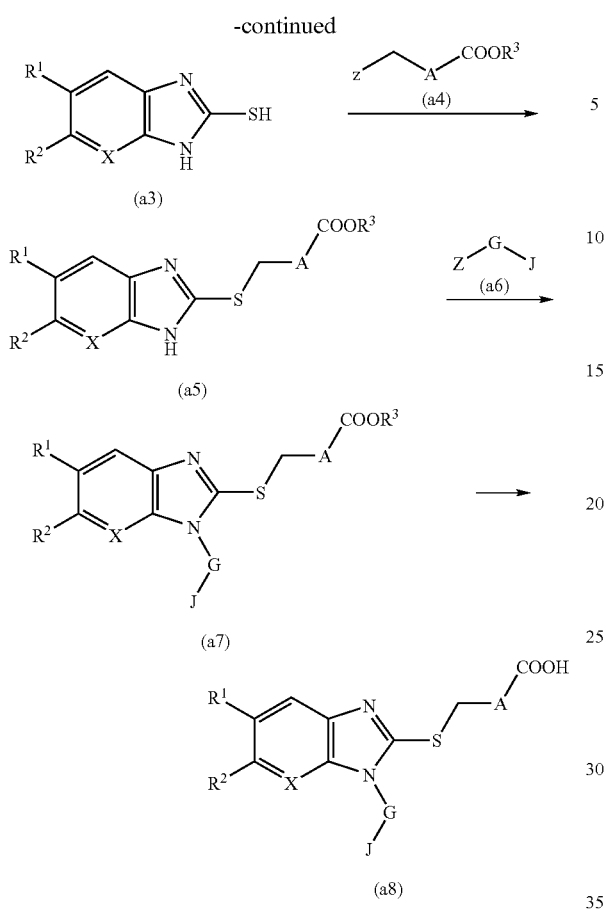

(a3)

(a5)

(a7)

(a8)

wherein Z represents a halogen, $R^1$, $R^2$, $R^3$, A, G, J, and x are as defined above.

Thus, the nitro group of a 2-nitroaniline derivative (a1) is reduced to give an orthophenylene diamine (a2). $CS_2$ is reacted with this diamine to produce a compound (a3), with which a halide ester derivative (a4) is reacted to obtain (a5). A halide derivative (a6) is reacted therewith to obtain (a7), which is hydrolyzed to yield a benzimidazole derivative (a8) of the present invention.

The reduction of the nitro group may be carried out under a standard condition for catalytic reduction. For example, a reaction is carried out with hydrogen gas in the presence of a catalyst such as Pd—C at a temperature of room temperature to 100° C. Alternatively, a method of treatment using zinc or tin under an acidic condition, or a method of using zinc powder at a neutral or alkaline condition can be used.

The reaction of an orthophenylene diamine derivative (a2) with $CS_2$ may be carried out using, for example, a method as described in J. Org. Chem. 19:631-637, 1954, or J. Med. Chem. 36: 1175-1187, 1993 (EtOH solution).

The reaction of a thiobenzimidazole (a3) and a halide ester (a4) may be carried out according to the condition of the conventional S-alkylation, for example in the presence of a base such as NaH, $Et_3N$, NaOH, or $K_2CO_3$ at a temperature of 0° C. to 200° C. under stirring.

The reaction of a thiobenzimidazole (a5) and a halide derivative (a6) may be carried out according to the condition for the conventional N-alkylation or N-acylation, for example in the presence of a base such as NaH, $Et_3N$, NaOH, or $K_2CO_3$ at a temperature of 0° C. to 200° C. under stirring.

As the elimination reaction of the carboxy protecting group $R^3$, preferably a method of hydrolysis is employed using an alkali such as lithium hydroxide or an acid such as trifluoroacetic acid.

Synthetic method (B)

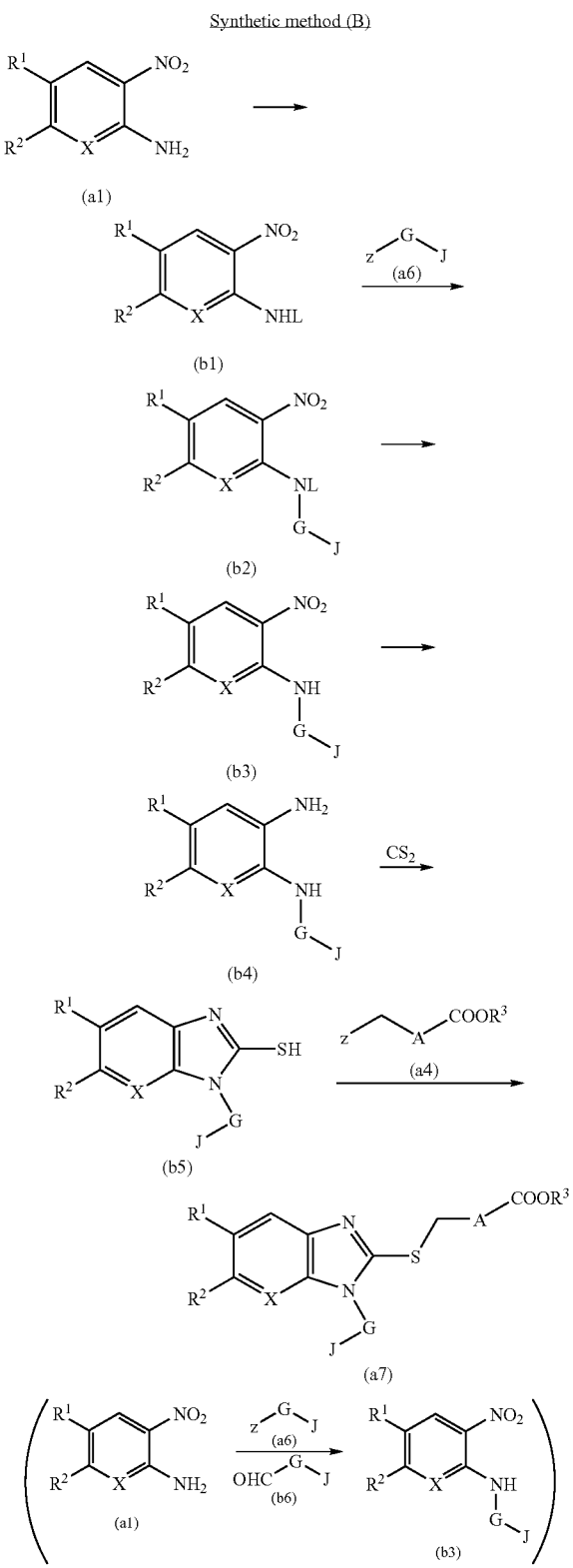

Thus, the amino group of a 2-nitroaniline derivative (a1) can be protected with L to give (b1). A halide derivative (a6) is reacted therewith to obtain (b2), from which L is deprotected to obtain (b3). The nitro group of (b3) is reduced to obtain an orthophenylene diamine derivative (b4). $CS_2$ is reacted therewith to yield a compound (b5), with which a halide ester derivative (a4) is reacted to obtain (a7) which may be hydrolyzed to yield a benzimidazole derivative of the present invention. Alternatively, it is also possible to obtain a compound (b3) directly by allowing the 2-nitroaniline derivative (a1) as it is unprotected to be reacted to a halide derivative (a6) or an aldehyde derivative (b6). As the protecting group L, there can be mentioned a trifluoroacetic acetyl group, an acetyl group, a t-butoxycarbonyl group, a benzyl group, and the like. The reaction of the 2-nitroaniline derivative (a1) and the aldehyde derivative (b6) may be carried out according to the conditions of the conventional reductive amination using a reducing agent such as a complex hydrogen compound, for example $LiAlH_4$, $NaBH_4$, $NaB_3CN$, $NaBH(OAc)_3$, etc. or diborane, in a solvent such as ethanol, methanol, and dichloromethane at a temperature condition of 0° C. to 200° C. The other reactions may be carried out as in the Synthetic method (A).

The thiobenzimidazole derivative (1) of the present invention in which E is COOH, m is 0, and G is an amide bond can be prepared by the synthetic method (C) shown below:

Synthetic method (C)

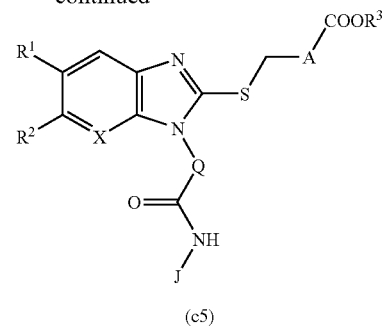

(c5)

wherein Q represents a methylene group, a phenylene group, etc., and Z represents a halogen. $R^1$, $R^2$, $R^3$, A, J, and X are as defined above, provided that $R^3$ is a protecting group such as an ethyl group, a methyl group, etc. inactive in an acid.

Thus, a tert-butyl ester halide derivative (c1) is reacted with a thiobenzimidazole compound (a5) to obtain a compound (c2), which is subjected to hydrolysis under an acidic condition to yield (c3). An amine derivative (c4) is reacted therewith to yield (c5), which is subjected to hydrolysis to obtain the benzimidazole derivative of the present invention.

The condensation amidation may be carried out by a conventional method using a condensing agent. As the condensing agent, there can be mentioned DCC, DIPC, EDC=WSCI, WSCIHCl, BOP, DPPA, etc., which may be used alone or in combination with HONSu, HOBt, HOOBt, etc. The reaction may be carried out in a appropriate solvent such as THF, chloroform, t-butanol, etc. at a temperature condition of 0° C. to 200° C. The other reactions may be carried out as in the Synthetic method (A).

The thiobenzimidazole derivative (1) of the present invention in which E is COOH, m is 0, and G is an ether bond can be prepared by the synthetic method (D) shown below:

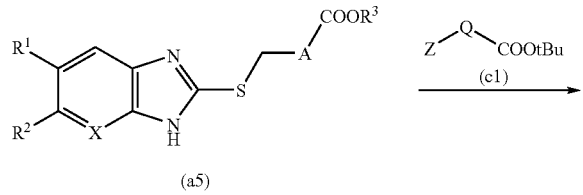

Synthetic method (D)

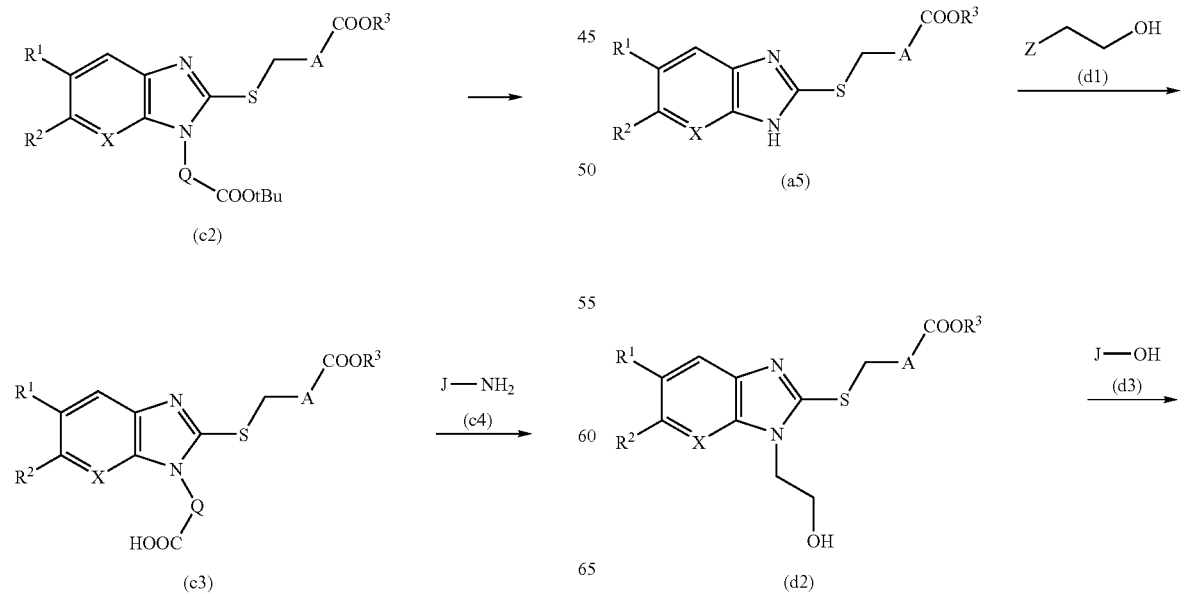

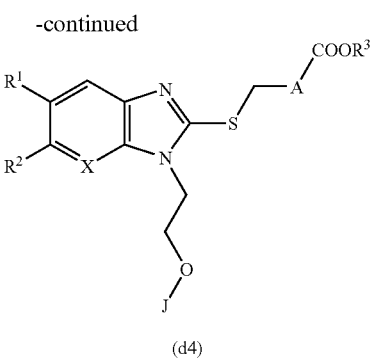

(d4)

wherein Z represents a halogen, $R^1$, $R^2$, $R^3$, A, J, and X are as defined above.

Thus, a thiobenzimidazole compound (a5) is reacted with, for example, a halide alcohol derivative (d1) to yield a compound (d2). A phenol derivative (d3) is reacted therewith to yield an ether (d4), which is subjected to hydrolysis to yield a benzimidazole derivative (a8) of the present invention.

The etherification may be carried out using a phosphine compound such as triphenyl phosphine and tributyl phosphine and an azo compound such as DEAD and TMAD in a suitable solvent such as N-methylmorpholine and THF at a temperature of 0° C. to 200° C. in a Mitsunobu reaction or a related reaction thereof. The other reactions may be carried out as in the Synthetic method (A).

The thiobenzimidazole derivative (1) of the present invention in which E is a tetrazole and m is 0 can be prepared by the synthetic method (E) shown below:

Synthetic method (E)

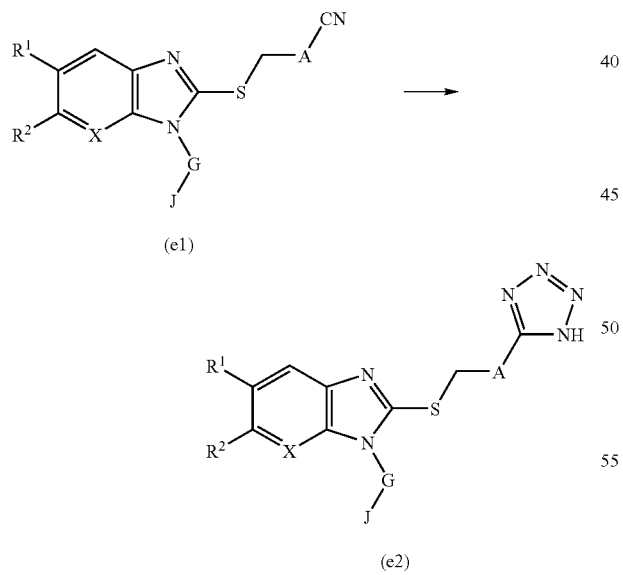

wherein $R^1$, $R^2$, A, G, J, and X are as defined above.

A nitrile (e1) is reacted with various azi compounds to be converted to a tetrazole (e2).

As the azi compound, there can be mentioned a trialkyltin azide compound such as trimethyltin azide, and hydrazoic acid or an ammonium salt thereof. When an organic tin azide compound is used, 1-4 fold molar amount is used relative to the compound (e1). When hydrazoic acid or an ammonium salt thereof is used, 1-5 fold molar amount of sodium azide or a tertiary amine such as ammonium chloride and triethylamine may be used relative to the compound (e1). Each reaction may be carried out at at temperature of 0° C. to 200° C. in a solvent such as toluene, benzene and DMF.

The thiobenzimidazole derivative (1) of the present invention in which m is 1 or 2 can be prepared by the synthetic method (F) shown below:

Synthetic method (F)

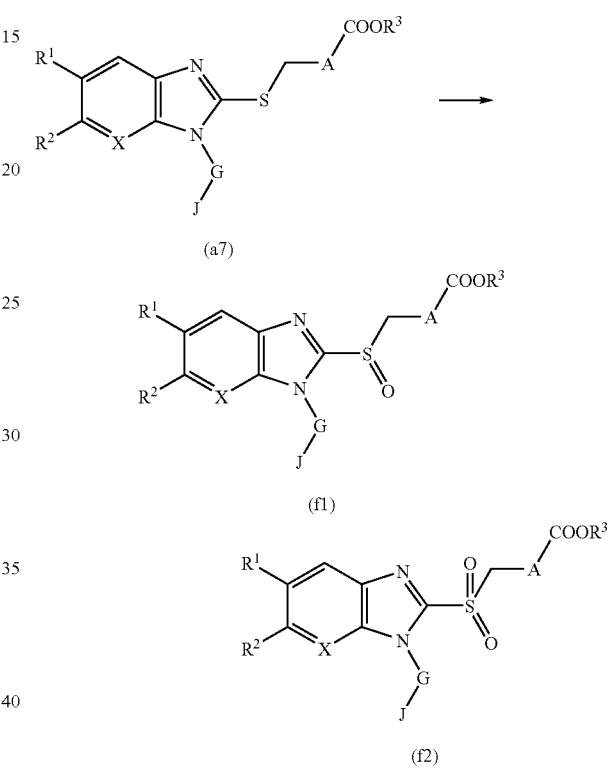

wherein $R^1$, $R^2$, $R^3$, A, G, J, and X are as defined above.

Thus, a thiobenzimidazole compound (a7) may be reacted with a peroxide compound in a suitable medium to yield a sulfoxide derivative (f1) and/or a sulfone derivative (f2). As the peroxide compound used, there can be mentioned perbenzoic acid, m-chloroperbenzoic acid, peracetic acid, hydrogeny peroxide, and the like, and as the solvent used, there can be mentioned chloroform, dichloromethane, and the like. The ratio of the compound (a7) to the peroxide compound used is selected from, but not limited to, a broad range as appropriate, and generally 1.2 to 5 fold molar amount, for example, may be preferably used. Each reaction is carried out generally at about 0 to 50° C., and preferably at 0° C. to room temperature, and is generally complete in about 4-20 hours.

The benzimidazole derivatives of the present invention can be converted, as needed, to medically acceptable non-toxic cation salts. As such a salt, there can be mentioned an alkali metal ion such as $Na^+$ and $K^+$; an alkaline earth metal ion such as $Mg^{2+}$ and $Ca^{2+}$; a metal ion such as $Al^{3+}$ and $Zn^{2+}$; or an organic base such as ammonia, triethylamine, ethylenediamine, propanediamine, pyrrolidine, piperidine, piperadine, pyridine, lysine, choline, ethanolamine, N,N- diethylethanolamine, 4-hydroxypiperidine, glucosamine, and N-methylglucamine. Among them, Na$^+$, Ca$^{2+}$, lysine, choline, N,N-dimethylethanolamine and N-methylglucamine are preferred.

The benzimidazole derivatives of the present invention inhibit human chymase activity. Specifically, their IC50 is not greater than 1000, preferably not smaller than 0.01 and less than 1000, and more preferably not smaller than 0.05 and less than 500. The benzimidazole derivatives of the present invention having such excellent inhibitory action on human chymase can be used as clinically applicable preventive and/or therapeutic agents for various diseases.

The benzimidazole derivatives of the present invention can be administered as pharmaceutical compositions together with pharmaceutically acceptable carriers by oral or parenteral routes after being shaped into various dosage forms. As the parenteral administration, there can be mentioned intravenous, subcutaneous, intramuscular, percutaneous, rectal, nasal, and eye drop administration.

Dosage forms for said pharmaceutical compositions include the following. For example, in the case of oral administration, there can be mentioned dosage forms such as tablets, pills, granules, powders, solutions, suspensions, syrups, and capsules.

As used herein, tablets are shaped by a conventional method using a pharmaceutically acceptable carrier such as an excipient, a binder, and a disintegrant. Pills, granules, and powders can also be shaped by a conventional method using an excipient etc. Solutions, suspensions, and syrups may be shaped by a conventional method using glycerin esters, alcohols, water, vegetable oils, and the like. Capsules can be shaped by filling a granule, a powder, and a solution into a capsule made of gelatin etc.

Among the parenteral preparations, those for intravenous, subcutaneous, and intramuscular administration can be administered as an injection. As injections, a benzoic acid derivative is dissolved in a water soluble liquid such as physiological saline, or in a non-water soluble liquid comprising an organic ester such as propylene glycol, polyethylene glycol, and a vegetable oil.

In the case of percutaneous administration, dosage forms such as ointments and creams can be used. Ointments can be prepared by mixing a benzoic acid derivative with a fat or lipid, vaseline, etc., and creams can be prepared by mixing a benzoic acid derivative with an emulsifier.

In the case of rectal administration, gelatin soft capsules can be used to prepare suppositories.

In the case of nasal administration, they can be used as a formulation comprising a liquid or powder composition. As the base for liquid formulations, water, saline, a phosphate buffer, an acetate buffer etc. can be used, and furthermore they may include a surfactant, an antioxidant, a stabilizer, a preservative, and a thickening agent. As the base for powder formulations, there can be mentioned polyacrylic acid salts that are readily solubule in water, cellulose lower alkyl ethers, polyethylene glycol, polyvinylpyrrolidone, amylose, pullulan, etc. that are water-absorptive, or celluloses, starches, proteins, gums, crosslinked vinyl polymers, etc. that are hardly water-soluble, and preferably they are water-absorptive. Alternatively, they may be combined. Furthermore, for powder formulations, an antioxidant, a colorant, a preservative, a disinfectant, a corrigent, etc. can be added. Such liquid formulations and powder formulations can be administered using, for example, a spraying device etc.

For eye drop administration, they can be used as aqueous or non-aqueous eye drops. For the aqueous eye drops, sterile purified water, physiological saline etc. can be used as a solvent. When sterile purified water is used as the solvent, a suspending agent such as a surfactant and a polymer thickener may be added to prepare an aqueous eye drop suspension. Alternatively, a solubilizing agent such as a nonionic surfactant may be added to prepare a soluble eye drop solution. The non-aqueous eye drop can use a non-aqueous solvent for injection as a solvent, and can be used as a non-aqueous eye drop solution.

In the case where administration to the eye is performed by a method other than the eye drop, dosage forms such as an eye ointment, an application solution, an epipastic, and an insert can be used.

In the case of nasal or oral inhalation, they are inhaled as a solution or a suspension of the benzimidazole derivatives of the present invention with a commonly used pharmaceutical excipient using, for example, an aerosol spray for inhalation, etc. Alternatively, the benzimidazole derivatives of the present invention in a lyophilized powder form can be administered to the lung using an inhaling device that permits direct contact to the lung.

To such various formulations, pharmaceutically acceptable carriers such as an isotonic agent, a preservative, a disinfectant, a wetting agent, a buffering agent, an emulsifier, a dispersant, a stabilizer, etc. can be added as needed.

To these formulations, blending of an antimicrobial agent, a treatment such as filtration through a bacteria-retaining filter, heating, radiation, etc. can be carried out for sterilization. Alternatively, sterile solid formulations can be prepared, which may be used by dissolving or suspending them in an appropriate sterile solution immediately prior to use.

The dosages of the benzimidazole derivatives of the present invention vary depending on the type of diseases, route of administration, the condition, age, sex, body weight etc. of the patient, but they are generally in the range of about 1 to 500 mg/day/patient for oral administration, and preferably 1 to 300 mg/day/patient. In the case of parenteral administration such as intravenous, subcutaneous, intramuscular, percutaneous, rectal, nasal, eye drop, and inhalation administration, they are about 0.1 to 100 mg/day/patient, and preferably 0.3 to 30 mg/day/patient.

When the benzimidazole derivatives of the present invention are used as a preventive agent, they can be administered according to a known method depending on each condition.

As the target diseases for the preventive and/or therapeutic agents of the present invention, there can be mentioned, for example, diseases of respiratory organs such as bronchial asthma, inflammatory/allergic diseases such as allergic rhinitis, atopic dermatitis, and urticaria; diseases of circulatory organs such as sclerosing vascular lesions, intravascular stenosis, disturbances of peripheral circulation, renal failure, and cardiac failure; diseases of bone/cartilage metabolism such as rheumatoid arthritis and osteoarthritis.

EXAMPLES

The present invention will now be explained in more detail with reference to Preparation Examples, Working Examples, and Test Examples. It should be noted, however, that these examples do not limit the scope of the invention in any way.

Reference Example 1

Preparation of 5,6-dimethylbenzimidazole-2-thiol

To 5,6-dimethylorthophenylene diamine (4.5 g, 33 mmol) in pyridine (40 ml) was added carbon disulfide (40 ml, 0.66 mol). The resulting solution was heated to reflux under stirring for 18 hours, to which was added water, followed by extraction with ethyl acetate. After drying the ethyl acetate phase with anhydrous magnesium sulfate, it was concentrated, and dried under reduced pressure at 80° C. for 6 hours to obtain the title compound (4.1 g, yield 70%).

Reference Example 2

Preparation of 2-((5,6-dimethylbenzimidazole-2-ylthio)methyl)benzoic acid methyl ester To the resulting 5,6-dimethylbenzimidazole-2-thiol (89 mg, 0.50 mmol) in dimethylformamide (2 ml), triethylamine (84 µl, 0.6 mmol) and 2-bromomethyl benzoic acid methyl ester (137 mg, 0.6 mmol) were added. After the resulting solution was stirred at 80° C. for 1.5 hours, water was added, followed by extraction with ethyl acetate. After drying the ethyl acetate phase with anhydrous magnesium sulfate, it was concentrated, and the residue was purified by silica gel column chromatography (hexane:ethyl acetate=3:1) to obtain the title compound (146 mg, yield 90%). The compound was confirmed by identification of molecular weight using LC-MS. Calculated M=326.11, measured $(M+H)^+$ =327.2

Reference Example 3

In a similar manner to Reference Example 2, the following compounds were synthesized. The compounds were confirmed by identification of molecular weight using LC-MS.

3-((5,6-dimethylbenzimidazole-2-ylthio)methyl)pyridine-2-carboxylic acid ethyl ester
Calculated M=341.12, found $(M+H)^+$=342.2
2-((5,6-dimethylbenzimidazole-2-ylthio)methyl)furane-3-carboxylic acid methyl ester
Calculated M=316.09, found $(M+H)^+$=317.2
3-((5,6-dimethylbenzimidazole-2-ylthio)methyl)thiphene-2-carboxylic acid methyl ester
Calculated M=332.07, found $(M+H)^+$=333.2
2-(benzimidazole-2-ylthiomethyl)benzoic acid methyl ester
Calculated M=298.08, found $(M+H)^+$=299.2
3-(benzimidazole-2-ylthiomethyl)pyridine-2-carboxylic acid ethyl ester
Calculated M=313.09, found $(M+H)^+$=314.2
3-(benzimidazole-2-ylthiomethyl)thiophene-2-carboxylic acid methyl ester
Calculated M=304.03, found $(M+H)^+$=305.2
2-(benzimidazole-2-ylthiomethyl)furane-3-carboxylic acid methyl ester
Calculated M=288.06, found $(M+H)^+$=289.2
4-benzimidazole-2-ylthiobutanoic acid methyl ester
Calculated M=264.09, found $(M+H)^+$=265.2
2-((5,6-dichlorobenzimidazole-2-ylthio)methyl)-5-chlorobenzoic acid methyl ester
Calculated M=399.96, found $(M+H)^+$=401.2
2-(benzimidazole-2-ylthiomethyl)-5-chlorobenzoic acid methyl ester
Calculated M=332.04, found $(M+H)^+$=333.2
4-((5,6-dimethylbenzimidazole-2-ylthio)butanoic acid ethyl ester
Calculated M=292.12, found $(M+H)^+$=293.40
2-((5,6-dichlorobenzimidazole-2-ylthio)methyl)-benzoic acid methyl ester
Calculated M=366.00, found $(M+H)^+$=367.0
2-((5,6-dichlorobenzimidazole-2-ylthio)methyl)pyridine-3-carboxylic acid methyl ester
Calculated M=366.99, found $(M+H)^+$=368.0

Example 1

Preparation of Compound No. 143

Sodium hydride (1.1 mg, 0.306 mmol) and 2 ml of tetrahydrofuran was added to a previously dried reaction vessel. To the mixture were added 2-((5,6-dimethylbenzimidazole-2-ylthio)methyl)benzoic acid methyl ester (50 mg, 0.153 mmol) and 1-chloromethylnaphthalene (69 µl, 0.459 mmol), which was then stirred at 60° C. for 45 minutes. Water was added thereto, followed by extraction with ethyl acetate. After drying the ethyl acetate phase with anhydrous sodium sulfate, it was concentrated, and the residue was purified by silica gel column chromatography (hexane:ethyl acetate=4:1) to obtain 2-((5,6-dimethyl-1-(1-naphthylmethyl)benzimidazole-2-ylthio)methyl)benzoic acid methyl ester (yield 32%).

To 2-((5,6-dimethyl-1-(1-naphthylmethyl)benzimidazole-2-ylthio)methyl)benzoic acid methyl ester (23 mg, 0.08 mmol) in tetrahydrofuran (1 ml) and methanol (0.5 ml), 4N aqueous sodium hydroxide solution (0.25 ml) was added. After stirring at room temperature for 5 hours, 6N hydrochloric acid was added to stop the reaction, followed by extraction with ethyl acetate. The ethyl acetate phase was washed with saturated saline, and then dried in anhydrous sodium sulfate. The solvent was evaporated under reduced pressure to obtain the title compound (24 mg, yield quantitative).

The compound was confirmed by identification of molecular weight using LC-MS.
Calculated M=452.16, found $(M+H)^+$=453.2

Example 2

In a similar manner to Working Example 1, the compounds in Tables 41 to 45 were synthesized using the compounds in Reference Examples 2 or 3 and various halide derivatives. The compounds were confirmed by identification of molecular weight using LC-MS.

TABLE 41

| Compound No. | Calculated M | Found $(M + H)^+$ | Recovery (overall) % |
|---|---|---|---|
| 390 | 406.14 | 407.2 | 29 |
| 391 | 422.11 | 423.2 | 16 |
| 315 | 417.15 | 418.2 | 32 |
| 376 | 406.14 | 407.2 | 25 |
| 333 | 417.15 | 418.2 | 6 |
| 82 | 416.16 | 417.2 | 12 |
| 83 | 416.16 | 417.2 | 9 |
| 84 | 416.16 | 417.2 | 33 |
| 97 | 432.15 | 433.2 | 18 |
| 98 | 432.15 | 433.2 | 26 |
| 99 | 432.15 | 433.2 | 8 |
| 94 | 470.13 | 471.2 | 14 |
| 95 | 470.13 | 471.2 | 10 |
| 96 | 470.13 | 471.2 | 13 |
| 100 | 486.12 | 487.2 | 26 |
| 101 | 486.12 | 487.2 | 8 |
| 85 | 420.13 | 421.2 | 9 |
| 86 | 420.13 | 421.0 | 12 |
| 87 | 420.13 | 421.2 | 44 |
| 88 | 436.10 | 437.2 | 42 |
| 89 | 436.10 | 437.2 | 40 |

TABLE 41-continued

| Compound No. | Calculated M | Found (M + H)+ | Recovery (overall) % |
| --- | --- | --- | --- |
| 90 | 436.10 | 437.2 | 28 |
| 91 | 480.07 | 481.0 | 12 |
| 103 | 427.14 | 428.2 | 12 |
| 104 | 427.14 | 428.2 | 6 |
| 105 | 427.14 | 428.2 | 11 |
| 784 | 434.11 | 435.2 | 36 |

TABLE 42

| Compound No. | Calculated M | Found (M + H)+ | Recovery (overall) % |
| --- | --- | --- | --- |
| 787 | 468.07 | 469.2 | 31 |
| 112 | 418.14 | 419.2 | 40 |
| 141 | 480.12 | 481.0 | 72 |
| 138 | 494.17 | 495.2 | 34 |
| 135 | 446.13 | 447.2 | 19 |
| 137 | 478.17 | 479.2 | 6 |
| 143 | 452.16 | 453.2 | 35 |
| 142 | 452.16 | 453.0 | 30 |
| 139 | 428.16 | 429.4 | 22 |
| 140 | 458.20 | 459.2 | 5 |
| 63 | 424.12 | 425.2 | 25 |
| 311 | 453.15 | 454.5 | 21 |
| 115 | 430.17 | 431.5 | 68 |
| 116 | 430.17 | 431.5 | 52 |
| 117 | 430.17 | 431.5 | 41 |
| 118 | 430.17 | 431.5 | 56 |
| 125 | 462.16 | 463.0 | 59 |
| 126 | 462.16 | 463.0 | 25 |
| 128 | 492.17 | 493.0 | 27 |
| 134 | 446.13 | 447.0 | 34 |
| 108 | 446.17 | 447.0 | 75 |
| 107 | 446.17 | 447.0 | 57 |
| 119 | 470.06 | 471.0 | 36 |
| 120 | 470.06 | 471.0 | 57 |
| 121 | 470.06 | 471.0 | 60 |
| 122 | 470.06 | 471.0 | 37 |
| 123 | 430.17 | 431.3 | 57 |

TABLE 43

| Compound No. | Calculated M | Found (M + H)+ | Recovery (overall) % |
| --- | --- | --- | --- |
| 124 | 462.16 | 463.3 | 67 |
| 127 | 462.16 | 463.3 | 62 |
| 129 | 446.17 | 447.3 | 47 |
| 130 | 446.17 | 447.3 | 40 |
| 319 | 425.12 | 426.3 | 30 |
| 506 | 466.17 | 467.2 | 16 |
| 505 | 466.17 | 467.0 | 14 |
| 93 | 480.07 | 481.0 | 45 |
| 136 | 478.17 | 479.2 | 60 |
| 37 | 402.14 | 403.4 | 25 |
| 39 | 442.03 | 443.0 | 51 |
| 317 | 403.14 | 404.0 | 56 |
| 318 | 443.03 | 444.0 | 46 |
| 380 | 442.14 | 443.2 | 51 |
| 377 | 420.15 | 421.2 | 34 |
| 378 | 460.04 | 461.0 | 30 |
| 386 | 414.10 | 415.2 | 37 |
| 383 | 392.12 | 393.2 | 30 |
| 384 | 432.01 | 433.0 | 29 |
| 395 | 458.11 | 459.2 | 23 |
| 392 | 436.13 | 437.2 | 15 |
| 393 | 476.02 | 477.0 | 15 |
| 401 | 430.08 | 431.2 | 50 |
| 398 | 408.10 | 409.2 | 20 |
| 399 | 447.99 | 449.0 | 7 |

TABLE 44

| Compound No. | Calculated M | Found (M + H)+ | Recovery (overall) % |
| --- | --- | --- | --- |
| 544 | 476.18 | 377.2 | 62 |
| 50 | 418.14 | 419.2 | 42 |
| 459 | 382.08 | 383.2 | 65 |
| 402 | 436.04 | 437.2 | 50 |
| 1 | 388.12 | 389.0 | 38 |
| 161 | 456.05 | 457.0 | 54 |
| 81 | 402.14 | 403.3 | 57 |
| 154 | 444.13 | 445.0 | 32 |
| 160 | 408.10 | 409.0 | 72 |
| 159 | 421.15 | 422.2 | 84 |
| 148 | 482.17 | 483.5 | 64 |
| 149 | 453.15 | 454.5 | 71 |
| 155 | 459.11 | 460.0 | 64 |
| 150 | 453.15 | 454.2 | 36 |
| 151 | 487.11 | 488.1 | 62 |
| 153 | 460.10 | 461.0 | 69 |
| 152 | 454.15 | 455.0 | 62 |
| 64 | 430.08 | 431.2 | 85 |
| 455 | 410.11 | 411.2 | 17 |
| 596 | 430.14 | 431.2 | 56 |
| 539 | 418.17 | 419.2 | 20 |
| 349 | 436.10 | 437.1 | 50 |
| 352 | 458.09 | 459.2 | 74 |
| 168 | 470.06 | 471.1 | 57 |
| 355 | 504.02 | 505.0 | 26 |
| 174 | 492.05 | 493.0 | 89 |
| 358 | 526.01 | 527.1 | 38 |

TABLE 45

| Compound No. | Calculated M | Found (M + H)+ | Recovery (overall) % |
| --- | --- | --- | --- |
| 324 | 493.04 | 494.2 | 32 |
| 320 | 431.08 | 432.1 | 15 |
| 147 | 466.17 | 467.2 | 72 |
| 616 | 490.16 | 491.2 | 22 |
| 805 | 382.17 | 383.2 | 52 |
| 804 | 368.16 | 369.2 | 56 |
| 66 | 438.14 | 440.2 | 54 |
| 592 | 430.14 | 432.3 | 5 |
| 811 | 380.16 | 382.2 | 72 |
| 582 | 436.06 | 437.1 | 59 |
| 580 | 436.06 | 437.1 | 59 |
| 584 | 480.03 | 483.1 | 37 |
| 583 | 480.03 | 483.0 | 52 |
| 578 | 420.09 | 421.2 | 30 |
| 574 | 416.12 | 417.2 | 39 |
| 595 | 452.12 | 453.2 | 22 |
| 594 | 478.14 | 479.1 | 23 |
| 588 | 432.11 | 433.1 | 65 |
| 587 | 432.11 | 433.2 | 48 |
| 586 | 432.11 | 433.1 | 50 |
| 590 | 427.10 | 428.2 | 24 |
| 589 | 427.10 | 428.3 | 17 |

Example 3

Preparation of Compound No. 547

Triethylamine (276 µl, 1.98 mmol) and 2-(bromoethyl) benzoic acid t-butyl ester (538 mg, 1.99 mmol) were added to 5,6-dimethylbenzimidazole-2-thiol (236 mg, 1.32 mmol) in 2 ml of dimethylformamide, which was then stirred at 80° C. for 3 hours. After the reaction was complete, water was added, followed by extraction with ethyl acetate. After drying the ethyl acetate phase with anhydrous sodium sulfate, it was concentrated, and the residue was purified by silica gel column chromatography (hexane:ethyl acetate=3:

1) to obtain 2-((5,6-dimethylbenzimidazole-2-ylthio)methyl)benzoic acid t-butyl ester (288 mg, yield 59%).

2-((5,6-dimethylbenzimidazole-2-ylthio)methyl)benzoic acid t-butyl ester (30 mg, 0.082 mmol) was dissolved in 3 ml of chloroform, to which triethylamine (17 µl, 0.123 mmol) and benzoyl chloride (14 µl, 0.123 mmol) were sequentially added and the mixture was stirred at room temperature for 2 hours. After the reaction was complete, water was added, followed by extraction with ethyl acetate. After drying the ethyl acetate phase with anhydrous sodium sulfate, it was concentrated, and 2-((5,6-dimethyl-1-(phenylcarbonyl)benzimidazole-2-ylthio)methyl)benzoic acid t-butyl ester was obtained (38 mg, yield quantitative).

2-((5,6-dimethyl-1-(phenylcarbonyl)benzimidazole-2-ylthio)methyl)benzoic acid t-butyl ester was dissolved in 1 ml of dichloromethane, to which trifluoroacetic acid (1 ml) was added and the mixture was stirred at room temperature for 6 hours. After the reaction was complete, the solvent was evaporated under reduced pressure and dried overnight to obtain the title compound (33 mg, yield quantitative).

The compound was confirmed by identification of molecular weight using LC-MS.
Calculated M=416.12, found $(M+H)^+$=417.0

Example 4

Preparation of Compound No. 561

The title compound was obtained in a similar manner to Working Example 3.

The compound was confirmed by identification of molecular weight using LC-MS.
Calculated M=452.09, found $(M+H)^+$=453.2

Reference Example 4

Preparation of 3-(naphthylmethyl)imidazolo(5,4-b)pyridine-2-thiol

To 2-amino-3-nitropyridine (1680 mg, 12 mmol) in a dimethylformamide (20 ml), sodium hydride (75 mg, 0.55 mmol) and 1-chloromethylnaphthalene (74 µl, 0.55 mmol) were added. After the resulting solution was stirred at 80° C. for 17 hours, water was added thereto, followed by extraction with ethyl ether. After drying the ethyl ether phase with anhydrous magnesium sulfate, it was concentrated, and the residue was purified by silica gel column chromatography (hexane:ethyl acetate=4:1) to obtain of naphthylmethyl(3-nitro(2-pyridil))amine (903 mg, yield 27%).

To naphthylmethyl(3-nitro(2-pyridil))amine (900 mg, 3.2 mmol) in ethanol (40 ml), 90.0 mg of 10% Pd—C was added. After the resulting solution was stirred in a hydrogen atmosphere at 50° C. for 8 hours, it was filtered through celite to remove Pd—C. The resulting solution was concentrated to obtain (3-amino(2-pyridil))naphthylmethylamine (860 mg, yield 99%). To the resulting (3-amino(2-pyridil))naphthylmethylamine (860 mg, 3.2 mmol) in ethanol (20 ml), carbon disulfide (6.1 ml, 102 mmol) was added. After the resulting solution was heated to reflux under stirring for 12 hours, it was allowed to stand at room temperature for 5 hours. The precipitate that deposited was filtered, and was washed three times with ethanol (5 ml). It was dried at 80° C. under reduced pressure for 5 hours to obtain the title compound (555 mg, yield 56%)

The compound was confirmed by identification of molecular weight using LC-MS.
Calculated M=291.08, found $(M+H)^+$=292.3

Reference Example 5

Preparation of 3-((2,5-dimethylphenyl)methyl)imidazolo(5,4-b)pyridine-2-thiol

The title compound was synthesized in a similar manner to Reference Example 4.

The compound was confirmed by identification of molecular weight using LC-MS.
Calculated M=269.01, found $(M+H)^+$=270.2

Example 5

Preparation of Compound No. 256

Using 3-(naphthylmethyl)imidazolo(5,4-b)pyridine-2-thiol (30 mg, 0.1 mmol) obtained in Reference Example 4 in a similar manner to Reference Example 2,2-((3-(naphthylmethyl)imidazolo(5,4-b)pyridine-2-ylthio)methyl)benzoic acid methyl ester was obtained (30 mg, yield 70%).

The 2-((3-(naphthylmethyl)imidazolo(5,4-b)pyridine-2-thio)methyl)benzoic acid methyl ester (30 mg, 0.068 mmol) thus obtained was subjected to hydrolysis in a similar manner to Example 1 to obtain the title compound (18.3 mg, yield 66%).

The compound was confirmed by identification of molecular weight using LC-MS.
Calculated M=425.12, found $(M+H)^+$=426.1

Example 6

The compounds in Table 46 were synthesized using the compounds obtained in Reference Examples 4 and 5 and various halide ester derivatives in a similar manner to Example 5.

The compounds were confirmed by identification of molecular weight using LC-MS.

TABLE 46

| Compound No. | Calculated M | Found $(M + H)^+$ | Yield (Overall) % |
|---|---|---|---|
| 253 | 403.14 | 407.2 | 67 |
| 327 | 404.13 | 423.2 | 46 |
| 329 | 426.12 | 418.2 | 58 |
| 361 | 437.10 | 438.0 | 52 |
| 364 | 459.08 | 460.0 | 66 |

TABLE 47

| Compound No. | Calculated M | Found $(M + H)^+$ | Yield (Overall) % |
|---|---|---|---|
| 321 | 428.13 | 429.2 | 27 |
| 354 | 461.10 | 462.2 | 20 |
| 460 | 379.14 | 380.2 | 19 |

TABLE 48

| Compound No. | Calculated M | Found $(M + H)^+$ | Yield (Overall) % |
|---|---|---|---|
| 52 | 493.15 | 494.2 | 12 |
| 53 | 493.15 | 494.2 | 11 |

Example 7

Preparation of Compound No. 264

4-methyl-2-nitroaniline (913 mg, 6 mmol) was dissolved in acetonitrile (18 ml), to which anhydrous trifluoroacetic acid (1.00 ml, 7.2 mmol) was added and the mixture was subjected to reflux for 1.5 hours. After cooling to room temperature, it was concentrated under reduced pressure and dried to obtain 4-methyl-2-nitro trifluoroacetanilide (1.396 g, yield 94%).

4-methyl-2-nitro trifluoroacetanilide (1.396 g, 5.63 mmol) was dissolved in dimethylformamide (14 ml), and then potassium carbonate (940 mg, 6.80 mmol) and 1-chloromethylnaphthalene (1.15 g, 6.51 mmol) were sequentially added at room temperature and heated to 100° C. After 1 hour and 40 minutes, 5N aqueous sodium hydroxide solution (7.5 ml) was added and refluxed as it was for 15 minutes. After 15 minutes, it was cooled to room temperature, and water (180 ml) was added and stored at 4° C. overnight. The crystals that deposited were filtered and were dried to obtain ((1-naphthyl)methyl)(4-methyl-2-nitro-phenyl)amine (1.587 g, yield 96%).

To (1-naphthyl)methyl)(4-methyl-2-nitro-phenyl)amine (1.0021 g, 3.43 mmol), ethanol (5 ml) and 1,4-dioxane (5 ml) were added, and 2.058 M aqueous sodium hydroxide solution (1 ml) was further added, and refluxed in an oil bath. After 15 minutes, it was removed from the oil bath, and zinc powder (897 mg, 13.72 mmol) was fed thereto in portions. Then it was refluxed again in the oil bath for 2 hours. After 2 hours, it was concentrated under reduced pressure, and dissolved in ethyl acetate (50 ml), and washed twice with saturated saline (25 ml). After drying with magnesium sulfate, it was concentrated under reduced pressure and dried to obtain a brown oil of ((1-naphthyl)methyl) (2-amino-4-methyl-phenyl)amine (943.1 mg).

Subsequently, ((1-naphthyl)methyl)(2-amino-4-methyl-phenyl)amine (943.1 mg, 3.59 mmol) was dissolved in ethanol (6.4 ml), to which carbon bisulfide (7 ml, 116 mmol) was added, and then refluxed. After 10 hours, it was returned to room temperature, concentrated under reduced pressure. Ethanol (2 ml) was added to the residue, which was stirred at room temperature for 30 minutes, and was further stirred on ice for 30 minutes. The resulting crystals were filtered, and dried to obtain 1-((1-naphthyl)methyl)-6-methyl-benzimidazole-2-thiol (459.1 mg, yield 44%, 2 steps).

1-((1-naphthyl)methyl)-6-methyl-benzimidazole-2-thiol (431.1 mg, 1.42 mmol) was dissolved in dimethylformamide (12 ml), to which triethylamine (0.296 ml, 2.12 mmol) and 2-bromomethyl benzoic acid methyl ester (390.1 mg, 1.70 mmol) were added and heated to 80° C. After 5 hours and 50 minutes, triethylamine (0.296 ml, 2.12 mmol) and 2-bromomethyl benzoic acid methyl ester (325 mg, 1.42 mmol) were added, and heated for 1 hour and 10 minutes. Thereafter, it was concentrated under reduced pressure, and dissolved in ethyl acetate (80 ml), washed twice with water (30 ml), and dried in magnesium sulfate. The solvent was concentrated under reduced pressure. The residue was crystallized in ethyl acetate-hexane to obtain 410 mg, and the mother liquor was purified by silica gel column chromatography (hexane:ethyl acetate=6:1) to recover 87 mg of the same fraction as the crystals, with a total of 497 mg of 2-((1-((1-naphthyl)methyl)-6-methyl-benzimidazole-2-ylthio)methyl)benzoic acid methyl ester (yield 78%).

2-((1-((1-naphthyl)methyl)-6-methyl-benzimidazole-2-ylthio)methyl)benzoic acid methyl ester (497 mg, 1.098 mmol) was dissolved in methanol (10 ml) and tetrahydrofuran (10 ml), to which 4N aqueous lithium hydroxide solution (6.86 ml) was added. After stirring at room temperature for 2 hours and 30 minutes, saturated aqueous citric acid solution (10 ml) was added thereto to stop the reaction, and the mixture was concentrated under reduced pressure to reduce the amount of the solvent to about ⅓, which was dissolved in ethyl acetate (80 ml) and washed five times with water (20 ml). After concentrating the organic layer under reduced pressure, acetonitrile (10 ml) was added to the residue, which was again concentrated under reduced pressure, and the resulting crystals were filtered off and dried to obtain the title compound (439.1 mg, yield 91%).

The compound was confirmed by identification of molecular weight using LC-MS.

Calculated M=438.14, found $(M+H)^+$=439.3

Example 8

Preparation of Compound No. 272

In a similar method to Working Example 7, the title compound was obtained.

The compound was confirmed by identification of molecular weight using LC-MS.

Calculated M=454.14, found $(M+H)^+$=455.3

Example 9

Preparation of Compound No. 65

2-nitroaniline (829 mg, 6 mmol) and 1-methylindole carboxaldehyde (1242 mg, 7.8 mmol) were dissolved in 20 ml of tetrahydrofuran, to which acetic acid (200 μl) and NaBH(OAc)$_3$ (5087 mg, 24 mmol) were sequentially added and stirred at room temperature overnight. A saturated aqueous sodium hydrogen carbonate solution was added thereto, followed by extraction with ethyl acetate, dried with anhydrous sodium sulfate, and the solvent was evaporated. After purification by silica gel column chromatography (hexane:ethyl acetate=95:5), ((1-methylindole-3-yl)methyl) (2-nitrophenyl)amine was obtained (264 mg, yield 18%).

((1-methylindole-3-yl)methyl)(2-aminophenyl)amine (264 mg, 0.939 mmol) was dissolved in ethanol (10 ml), and Pd—C (50 mg, 10% Pd, 0.047 mmol) was added thereto, and stirred in hydrogen atmosphere at room temperature for 6 hours. After the reaction was complete, Pd—C was filtered off and the solvent was evaporated to obtain ((1-methylindole-3-yl)methyl)(2-aminophenyl)amine (212 mg, yield 90%).

((1-methylindole-3-yl)methyl)(2-aminophenyl)amine (212 mg, 0.845 mmol) was dissolved in pyridine (1 ml), and carbon bisulfide (1 ml, 16.9 mmol) was added thereto. The mixture was refluxed in nitrogen atmosphere for 1 hour. After the solvent was evaporated, it was purified by silica gel column chromatography (hexane:ethyl acetate=2:1) to obtain ((1-methylindole-3-yl)methyl)benzimidazole-2-thiol (96 mg, yield 39%).

Sodium hydride (12 mg, 0.342 mmol) and dimethylformamide (2 ml) were added to a previously dried reaction vessel. To the mixture were added ((1-methylindole-3-yl) methyl)benzimidazole-2-thiol (50 mg, 0.171 mmol) and 2-bromomethyl benzoic acid methyl ester (59 mg, 0.257 mmol), and then the mixture was stirred at 60° C. for 1 hour. Water was added thereto, followed by extraction with ethyl acetate. After the ethyl acetate phase was dried with anhydrous sodium sulfate, it was concentrated, and the residue was purified by silica gel column chromatography (hexane:

ethyl acetate=2:1) to obtain 2-((1-((-methylindole-3-yl)methyl)benzimidazole-2-ylthio)methyl)benzoic acid methyl ester (54 mg, yield 74%).

To 2-((1-((1-methylindole-3-yl)methyl)benzimidazole-2-ylthio)methyl)benzoic acid methyl ester (54 mg, 0.122 mmol) in tetrahydrofuran (2 ml) and methanol (1 ml), 4N aqueous lithium hydroxide solution (0.5 ml) was added. After stirring at room temperature overnight, 6N hydrochloric acid was added to stop the reaction, followed by extraction with ethyl acetate. After washing the ethyl acetate phase with saturated saline, it was dried with anhydrous sodium sulfate. The solvent was evaporated under reduced pressure to obtain the title compound (48 mg, yield 92%).

The compound was confirmed by identification of molecular weight using LC-MS.

Calculated M=427.14, found $(M+H)^+$=428.2

Example 10

The compounds in the above Table 47 were synthesized using various halide ester derivatives in a similar manner to Working Example 9. The compounds were confirmed by identification of molecular weight using LC-MS.

Example 11

Preparation of Compound No. 51

Sodium hydride (104 mg, 2.86 mmol) and tetrahydrofuran (16 ml) were added to a previously dried reaction vessel. To the mixture were added 2-(benzimidazole-2-ylthiomethyl)benzoic acid methyl ester (428 mg, 1.43 mmol) and 2-(bromomethyl)benzoic acid t-butyl ester (466 mg, 3.46 mmol), and then the mixture was stirred at 60° C. for 50 minutes. Water was added thereto, followed by extraction with ethyl acetate. After the ethyl acetate phase was dried with anhydrous sodium sulfate, it was concentrated, and the residue was purified by silica gel column chromatography (hexane: ethyl acetate=3:1) to obtain 2-((1-((2-((t-butyl)oxycarbonyl)phenyl)methyl)benzimidazole-2-ylthio)methyl)benzoic acid methyl ester (495 mg, yield 71%).

To 2-((1-((2-((t-butyl)oxycarbonyl)phenyl)methyl)benzimidazole-2-ylthio)methyl)benzoic acid methyl ester (248 mg, 0.51 mmol), 4N hydrochloric acid in dioxane (1.28 ml, 5.1 mmol) was added, and stirred at room temperature overnight. After the solvent was evaporated, it was dried under reduced pressure to obtain 2-((2-((2-(methoxycarbonyl)phenyl)methylthio)benzimidazolyl)methyl) benzoic acid (220 mg, yield quantitative).

2-((2-((2-(methoxycarbonyl)phenyl)methylthio)benzimidazolyl)methyl) benzoic acid (180 mg, 0.42 mmol) was dissolved in chloroform (6 ml), to which HOBT (68 mg, 0.504 mmol), aniline (46 µl, 0.504 mmol), t-butanol (1.2 ml) and EDCI (97 mg, 0.504 mmol) were sequentially added and stirred overnight at room temperature. Water was added thereto, followed by extraction with dichloromethane. After drying with anhydrous sodium sulfate, it was filtered, and the solvent was evaporated. It was purified by silica gel column chromatography (hexane:ethyl acetate=3:2) to obtain 2-((1-((2-(N-phenylcarbamoyl)phenyl)methylthio)benzimidazole-2-ylthio)methyl)benzoic acid methyl ester (86 mg, yield 40%).

To the thus obtained 2-((1-((2-(N-phenylcarbamoyl)phenyl)methylthio)benzimidazole-2-ylthio)methyl)benzoic acid methyl ester (86 mg, 0.169 mmol) in tetrahydrofuran (2 ml) and methanol (1 ml), 4N aqueous lithium hydroxide solution (0.5 ml) was added, and stirred at 60° C. for about 2 hours. 6N aqueous hydrochloric acid solution was added to stop the reaction, which was extracted with ethyl acetate. After washing the ethyl acetate phase with saturated saline, it was dried with anhydrous sodium sulfate. The solvent was evaporated under reduced pressure to obtain the title compound (83 mg, yield quantitative).

The compound was confirmed by identification of molecular weight using LC-MS.

Calculated M=493.15, found $(M+H)^+$=494.2

Example 12

In a similar method to Working Example 11, the compounds shown in the above Table 48 were obtained using various benzoic acid ester derivatives.

The compounds were confirmed by identification of molecular weight using LC-MS.

Example 13

Preparation of Compound No. 619

Sodium hydride (400 mg, 10.0 mmol) and dimethylformamide (30 ml) were added to a previously dried reaction vessel. To the mixture were added 2-(benzimidazole-2-ylthiomethyl)benzoic acid methyl ester (1500 mg, 5.0 mmol) and bromoacetate t-butyl ester (1463 mg, 7.5 mmol), and the mixture was stirred at 80° C. for 2 hours. Water was added thereto, followed by extraction with ether. After the ether phase was dried with anhydrous sodium sulfate, it was concentrated, and the residue was purified by silica gel column chromatography (hexane:ethyl acetate=5:1) to obtain 2-(2-((2-(methoxycarbonyl)phenyl)methylthio)benzimidazolyl)acetic acid t-butyl ester (1298 mg, yield 63%).

To 2-(2-((2-(methoxycarbonyl)phenyl)methylthio)benzimidazolyl)acetic acid t-butyl ester (1290 mg, 3.13 mmol), trifluoroacetic acid (15 ml) was added, and stirred at room temperature overnight. After the solvent was evaporated, it was dried under reduced pressure to obtain 2-(2-((2-(methoxycarbonyl)phenyl)methylthio)benzimidazolyl)acetic acid (715 mg, yield 64%).

2-(2-((2-(methoxycarbonyl)phenyl)methylthio)benzimidazolyl)acetic acid (35 mg, 0.1 mmol) was dissolved in tetrahydrofuran (3 ml), to which aniline (11.2 mg, 0.12 mmol) and EDCI (23 mg, 0.12 mmol) were added, and then the mixture was stirred overnight at room temperature. Water was added thereto, followed by extraction with ethyl acetate. After drying with anhydrous sodium sulfate, it was filtered, the solvent was evaporated. The residue was purified by silica gel column chromatography (hexane: ethyl acetate=3:2) to obtain 2-((1-((N-phenylcarbamoyl)methyl)benzimidazole-2-ylthio)methyl)benzoic acid methyl ester (27.5 mg, yield 64%).

2-((1-((N-phenylcarbamoyl)methyl)benzimidazole-2-ylthio)methyl)benzoic acid methyl ester (20 mg, 0.046 mmol) thus obtained was subjected to hydrolysis as in Working Example 1 to obtain the title compound (6.9 mg, yield 36%).

The compound was confirmed by identification of molecular weight using LC-MS.

Calculated M=417.11, found $(M+H)^+$=418.0

Example 14

In a similar method to Example 13, the compounds shown in the above Table 49 were obtained using various aniline derivatives.

The compounds were confirmed by identification of molecular weight using LC-MS.

TABLE 49

| Compound No. | Calculated M | Found (M + H)+ | Yield (Overall) % |
|---|---|---|---|
| 622 | 431.13 | 432.3 | 5 |
| 621 | 431.13 | 432.3 | 5 |
| 620 | 431.13 | 432.3 | 21 |
| 637 | 447.13 | 448.2 | 13 |
| 636 | 117.13 | 448.1 | 23 |
| 635 | 447.13 | 448.3 | 44 |
| 642 | 442.11 | 443.2 | 27 |
| 657 | 467.13 | 488.1 | 19 |

TABLE 50

| Compound No. | Calculated M | Found (M + H)+ | Yield (Overall) % |
|---|---|---|---|
| 765 | 457.15 | 458.2 | 5 |
| 767 | 457.15 | 458.2 | 32 |

TABLE 51

| Compound No. | Calculated M | Found (M + H)+ | Yield (Overall) % |
|---|---|---|---|
| 866 | 434.13 | 435.2 | 76 |
| 869 | 456.11 | 457.3 | 83 |
| 904 | 468.09 | 469.1 | 52 |
| 937 | 436.15 | 437.2 | 61 |

TABLE 52

| Compound No. | Calculated M | Found (M + H)+ | Yield (Overall) % |
|---|---|---|---|
| 953 | 476.18 | 477.2 | 36 |
| 985 | 428.18 | 429.2 | 67 |
| 977 | 400.15 | 401.4 | 2 |

Reference Example 6

Preparation of 2-((1-(2-hydroxyethyl)-5,6-dimethyl-benzimidazole-2-ylthio)]methyl)benzoic acid methyl ester To 2-((5,6-dimethylbenzimidazole-2-ylthio)methyl) benzoic acid methyl ester (326 mg, 1 mmol) obtained in Reference Example 2 in dimethylformamide, potassium carbonate (207 mg, 1.5 mmol) and 2-bromoethanol (150 mg, 1.2 mmol) were added, and the resulting solution was stirred at 80° C. for 12 hours. After the reaction was complete, it was extracted with ether and the solvent was evaporated. The residue was purified by a flash column chromatography (hexane:ethyl acetate=4:1) to obtain the the title compound (248 mg, yield 67%).

The compound was confirmed by identification of molecular weight using LC-MS.

Calculated M=370.14, found (M+H)+=371.2

Example 15

Preparation of Compound No. 736

To 2-((1-(2-hydroxyethyl)-5,6-dimethylbenzimidazole-2-ylthio)methyl)benzoic acid methyl ester (45 mg, 0.23 mmol) in N-methylmorpholine (3 ml), Pph$_3$ (62 mg, 0.24 mmol) and DEAD (10.6 ml, 40% in toluene, 0.24 mmol) were added and the mixture was stirred at room temperature. After 10 minutes, phenol (11.3 mg, 0.12 mmol) was added thereto, which was stirred at room temperature for 12 hours. The solvent was evaporated and the residue was purified by thin layer chromatography (hexane:ethyl acetate=1:1) to obtain 2-((5,6-dimethyl-1-(2-phenoxyethyl)benzimidazole-2-ylthio)methyl)benzoic acid methyl ester (44 mg, yield 81%).

Using 2-((5,6-dimethyl-1-(2-phenoxyethyl)benzimidazole-2-ylthio)methyl)benzoic acid methyl ester (35 mg, 0.078 mmol) in a similar method to Example 1, a hydrolysis reaction was carried out to obtain the title compound (31 mg, yield 94%). The compound was confirmed by identification of molecular weight using LC-MS.

Calculated M=432.15, found (M+H)+=433.2

Example 16

In a similar method to Example 15, the compounds shown in the above Table 50 were obtained using various phenol derivatives.

The compounds were confirmed by identification of molecular weight using LC-MS.

Example 17

Preparation of Compound No. 825

To an ester (33 mg, 0.075 mmol) of compound No. 68 obtained in Example 2 in dichloromethane, 50 to 60% m-chloroperbenzoic acid (26 mg, 0.083 mmol) was added while cooling on ice. After the resulting solution was stirred on ice for 2 hours, a saturated sodium hydrogen carbonate solution was poured and the solution obtained was extracted with chloroform. After washing the chloroform phase with water, it was concentrated and the residue was purified by thin layer chromatography (hexane:ethyl acetate=1:1) to obtain 2-(((5,6-dimethyl-1-(1-naphthylmethyl)benzimidazole-2-yl)sulfinyl)methyl)benzoic acid methyl ester (7.1 mg, yield 21%).

In a manner similar to Example 1, this was subjected to hydrolysis to obtain the title compound (5.2 mg, yield 76%).

The compound was confirmed by identification of molecular weight using LC-MS.

Calculated M=440.12, found (M+H)+=441.3

Example 18

Preparation of Compound No. 869

To an ester (39 mg, 0.094 mmol) of compound No. 37 obtained in Example 2 in dichloromethane (5 ml), 50 to 60% m-chloroperbenzoic acid (64 mg, 0.374 mmol) was added while cooling on ice. After the resulting solution was stirred at room temperature for 4 hours, a saturated sodium hydrogen carbonate solution was poured and the solution obtained was extracted with chloroform. After washing the chloroform phase with water, it was concentrated and the residue was purified by flash layer chromatography (hexane:ethyl acetate=5:1) to obtain 2-(((1-((2,5-dimethylphenyl)methyl)benzimidazole-2-yl)sulfonyl)methyl)benzoic acid methyl ester (37 mg, yield 87%).

In a manner similar to Example 1,2-(((1-((2,5-dimethylphenyl)methyl)benzimidazole-2-yl)sulfonyl)methyl)benzoic acid methyl ester (64 mg, 0.14 mmol) was subjected to hydrolysis to obtain the title compound (53 mg, yield 87%).

The compound was confirmed by identification of molecular weight using LC-MS.
Calculated M=434.13, measured (M+H)$^+$=435.2

Example 19

In a manner similar to Example 18, the compounds shown in the above Table 51 were synthesized using the esters of the compounds obtained in Working Example 2. The compounds were confirmed by identification of molecular weight using LC-MS.

Example 20

Preparation of Compound No. 952

To 5,6-dimethylbenzimidazole-2-thiol (713 mg, 4 mmol) in dimethylformamide (10 ml), triethylamine (836 µl, 6 mmol) and 2-bromomethylbenzonitrile (1176 mg, 6 mmol) were added. After stirring at 80° C. overnight, water was added to the mixture, followed by extraction with ethyl acetate. After the ethyl acetate phase was dried with anhydrous sodium sulfate, it was concentrated and the residue was purified by silica gel column chromatography (hexane:ethyl acetate=3:2) to obtain 2-((5,6-dimethylbenzimidazole-2-ylthio)methyl)benzenecarbonitrile (1159 mg, yield 99%).

Sodium hydride (178 mg, 4.90 mmol) and tetrahydrofuran (30 ml) were added to a previously dried reaction vessel. To the mixture were added 2-((5,6-dimethylbenzimidazole-2-ylthio)methyl)benzenecarbonitrile (719 mg, 2.45 mmol) and 2,5-dichlorobenzyl chloride (543 µl, 4.90 mmol), and the mixture was stirred at 60° C. for 40 minutes. Water was added thereto, followed by extraction with ethyl acetate. After the ethyl acetate phase was dried with anhydrous sodium sulfate, it was concentrated, and the residue was purified by silica gel column chromatography (hexane:ethyl acetate=3:1) to obtain 2-((1-((2,5-dimethylphenyl)methyl)-5,6-dimethylbenzimidazole-2-ylthio)methyl)benzenecarbonitrile (370 mg, yield 37%).

2-((1-((2,5-dimethylphenyl)methyl)-5,6-dimethylbenzimidazole-2-ylthio)methyl)benzenecarbonitrile (165 mg, 0.401 mmol) was dissolved in toluene (3 ml), to which Me$_3$SnN$_3$ (124 mg, 0.602 mmol) was added, and refluxed in nitrogen atmosphere overnight. After the reaction was complete, the solvent was evaporated, and the residue was purifed by silica gel column chromatography (dichloromethane:methanol=19:1) to obtain the title compound (75 mg, yield 41%).

The compound was confirmed by identification of molecular weight using LC-MS.
Calculated M=454.19, found (M+H)$^+$=455.2

Example 21

In a manner similar to Example 20, the compounds shown in the above Table 52 were obtained.
The compounds were confirmed by identification of molecular weight using LC-MS.

Example 22

Preparation of Recombinant Human Mast Cell Chymase

Recombinant pro-type human mast cell chymase was prepared according to the method reported by Urada et al. (Journal of Biological Chemistry 266: 17173, 1991). Thus, a culture supernatant of the insect cell (Tn5) infected with a recombinant baculovirus containing cDNA encoding human mast cell chymase was purified by heparin Sepharose (Pharmacia). After it was further activated by the method reported by Murakami et al. (Journal of Biological Chemistry 270: 2218, 1995), it was purified with heparin Sepharose to obtain an activated human mast cell chymase.

Example 23

Determination of the Activity of Inhibiting Recombinant Human Mast Cell Chymase

After a DMSO solution (2 µl) containing the compound of the present invention was added to 50 µl of buffer A (0.5-3.0 M NaCl, 50 mM Tris-HCl, pH 8.0) containing 1-5 ng of the activated human mast cell chymase obtained in Working Example 22, 50 µl of buffer A containing, as a substrate, 0.5 mM succinyl-alanyl-histidyl-prolyl-phenylalanylparanitroanilide (Bacchem) was added thereto and the mixture was allowed to react at room temperature for 5 minutes. Changes in absorbance at 405 nm with time were measured to evaluate the inhibitory activity.

As a result, IC50=not smaller than 1 nM and less than 10 nM was observed in compounds No. 63, 64, 65, 143, 174, 256, 264, 272, 311, 354, 319, 349, 358, 395, 401, and 402, and IC50=not smaller than 10 nM and not greater than 100 nM was observed in compounds No. 37, 50, 84, 115, 117, 119,, 121, 123, 130, 147, 168, 256, 320, 321, 324, 352, 355, 364, 380, 392, 398, 444, 455, 459, 460, 506, 863, 866, and 869.

As hereinabove described, the benzimidazole derivatives of the present invention exhibit a potent chymase inhibitory activity. Thus, it was revealed that the benzimidazole derivatives of the present invention are clinically applicable inhibitory substances for human chymase activity and can be used for prevention and/or therapy of various diseases in which human chymase is involved.

Example 24

Manufacture of Tablets

Tablets comprising, per tablet, the following were manufactured:

| | |
|---|---|
| Compound (No. 37) | 50 mg |
| Lactose | 230 mg |
| Potato starch | 80 mg |
| Polyvinylpyrrolidone | 11 mg |
| Magnesium stearate | 5 mg |

The compound of the present invention (the compound in working Example 2), lactose and potato starch were mixed, and the mixture was evenly soaked in 20% polyvinylpyrrolidone in ethanol. The mixture was filtered through a 20 nm mesh, dried at 45° C., and filtered again through a 15 nm mesh. Granules thus obtained were mixed with magnesium stearate and were compressed into tablets.

INDUSTRIAL APPLICABILITY

The thiobenzimidazole derivatives of the present invention and the medically acceptable salts thereof exhibit a potent activity of inhibiting human chymase. Thus, said thiobenzimidazole derivatives and the medically acceptable salts thereof can be used, as a human chymase inhibitor, as clinically applicable preventive and/or therapeutic agents for inflammatory diseases, allergic diseases, diseases of respiratory organs, diseases of circulatory organs, or diseases of bone/cartilage metabolism.

The invention claimed is:

1. A thiobenzimidazole compound or medically acceptable salt thereof represented by the following formula (1):

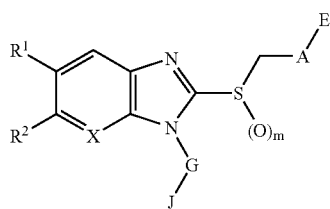

(1)

wherein,

R$^1$ and R$^2$ simultaneously or respectively independently represent a hydrogen atom, halogen atom, trifluoromethyl group, cyano group, hydroxyl group, methyl group, ethyl group, (n- or i-)propyl group, (n-, i-, s- or t-)butyl group, methoxy group, ethoxy group, (n- or i-)propyloxy group, (n-, i-, s- or t-)butyloxy group, or R$^1$ and R$^2$ together represent —O—CH$_2$—O—, —O—CH$_2$—CH$_2$—O— or —CH$_2$—CH$_2$—CH$_2$— in this case, the carbon atoms may be substituted with one or a plurality of methyl groups, ethyl groups, (n- or i-)propyl groups or (n-, i-, s- or t-)butyl groups;

A represents a single bond, a substituted or non-substituted methylene group, ethylene group, (n- or i-)propylene group or (n-, i- or t-)butylene group, substituted or non-substituted phenylene group, indenylene group or naphthylene group, substituted or non-substituted pyridylene group, furanylene group, thiophenylene group, pyrimidylene group, benzophenylene group, benzimidazolene group, quinolylene group, indolene group or benzothiazolene group and substitution groups here are represented by a halogen atom, OH, NO$_2$, CN, methyl group, ethyl group (n- or i-)propyl group, (n-, i-, s- or t-)butyl group, methoxy group, ethoxy group, (n- or i-)propyloxy group, (n-, i-, s- or t-)butyloxy group, in this case, substitution groups may be acetal-bonded at mutually adjacent sites, methylthio group, ethylthio group, (n- or i-)propylthio group, (n-, i-, s- or t-)butylthio, methylsulfonyl group, ethylsulfonyl group, (n- or i-)propylsulfonyl group, (n-, i-, s- or t-)butylsulfonyl group, acetyl group, ethylcarbonyl group, (n- or i-)propylcarbonyl group, acetylamino group, ethylcarbonylamino group, (n- or i-) propylcarbonylamino group, (n-, i-, s- or t-)butylcarbonylamino group, trifluoromethyl group or trifluoromethoxy group, and one or a plurality of these may be respectively and independently substituted at an arbitrary location of a ring or alkylene group;

E represents COOR$^3$, SO$_3$R$^3$, CONHR$^3$, SO$_2$NHR$^3$, a tetrazole group, 5-oxo-1,2,4-oxadiazole group or 5-oxo-1,2,4-thiadiazole group wherein, R$^3$ represents a hydrogen atom, methyl group, ethyl group, (n- or i-)propyl group or (n-, i-, s- or t-)butyl group;

G represents a substituted or non-substituted methylene group, ethylene group, (n- or i-) propylene group or (n-, i- or t-)butylene group, and one or a plurality of O, S, SO$_2$ or NR$^3$ may be intermediately contained therein, wherein R$^3$ is the same as previously defined, and substitution groups here are represented by a halogen atom, OH, NO$_2$, CN, methyl group, ethyl group, (n- or i-)propyl group, (n-, i-, s- or t-)butyl group, methoxy group, ethoxy group, (n- or i-)propyloxy group, (n-, i-, s- or t-)butyloxy group, trifluoromethyl group, trifluoromethoxy group or oxo group;

m represents an integer of 0-2;

when m is 0 and A is a substituted or non-substituted methylene group, ethylene group, (n- or i-)propylene group or (n-, i- or t-)butylene group, J represents a substituted or non-substituted (n- or i-)propyl group, (n-, i-, s- or t-)butyl group, (n-, i-, ne- or t-)pentyl group, cyclohexyl group, indenyl group, furanyl group, thiophenyl group, pyrimidyl group, benzofuranyl group, benzimidazolyl group, quinolyl group, isoquinolyl group, quinoxalyl group, benzooxadiazolyl group, benzothiadiazolyl group, indolyl group, N-methylindolyl group, benzothiazolyl group, benzothiophenyl group or benzoisooxazolyl group substituted naphthyl group, when m is 0 and A is a substituted or non-substituted phenylene group, indenylene group or naphthylene group, or a substituted or non-substituted pyridylene group, furanylene group, thiophenylene group, pyrimidylene group, benzophenylene group, benzimidazolene group, quinolylene group, indolene group or benzothiazolene group, J represents a substituted or non-substituted cyclohexyl group, phenyl group, indenyl group, naphthyl group, furanyl group, thiophenyl group, pyrimidyl group, benzofuranyl group, benzimidazolyl group, quinolyl group, isoquinolyl group, quinoxalyl group, benzooxadiazolyl group, benzothiadiazolyl group, indolyl group, N-methylindolyl group, benzothiazolyl group, benzothiophenyl group or benzoisooxazolyl group;

when m is 0 and A is a single bond or when m is 1 or 2, J represents a substituted or non-substituted cyclohexyl group, phenyl group, indenyl group, naphthyl group, furanyl group, thiophenyl group, pyrimidyl group, benzofuranyl group, benzimidazolyl group, quinolyl group, isoquinolyl group, quinoxalyl group, benzooxadiazolyl group, benzothiadiazolyl group, indolyl group, N-methylindolyl group, benzothiazolyl group, benzothiophenyl group or benzoisooxazolyl group; substitution groups here are represented by a halogen atom, OH, NO$_2$, CN, methyl group, ethyl group (n- or i-)propyl group, (n-, i-, s- or t-)butyl group, methoxy group, ethoxy group, (n- or i-)propyloxy group, (n-, i-, s- or t-)butyloxy group, methylthio group, ethylthio group, (n- or i-)propylthio group, (n-, i-, s- or t-)butylthio group, methylsulfonyl group, ethylsulfonyl group, (n- or i-)propylsulfonyl group, (n-, i-, s- or t-)butylsulfonyl group, acetyl group, ethylcarbonyl group, (n- or i-)propylcarbonyl group, acetylamino group, ethylcarbonylamino group, (n- or i-) propylcarbonylamino group, (n-, i-, s- or t-)butylcarbonylamino group, trifluoromethyl group or trifluoromethoxy group, and one or a plurality of these may be respectively and independently substituted at an arbitrary location of a ring or alkyl group; and, X represents CH or a nitrogen atom.

2. The thiobenzimidazole compound or medically acceptable salt thereof according to claim 1, wherein, in the above formula (1), A is a substituted or non-substituted methylene group, ethylene group, (n- or i-) propylene group or (n-, i or t-)butylene group, a substituted or non-substituted phenylene group, indenylene group, naphthylene group, or a substituted or non-substituted pyridylene group, furanylene group, thiophenylene group, pyrimidylene group, benzophenylene group, benzimidazolene group, quinolylene group, indolene group or benzothiazolene group.

3. The thiobenzimidazole compound or medically acceptable salt thereof according to claim 1, wherein in the above formula (1), A is a substituted or non-substituted pyridylene group, furanylene group, thiophenylene group, pyrimidylene group, benzophenylene group, benzimidazolene group, quinolylene group, indolene group or benzothiazolene group.

4. The thiobenzimidazole compound or medically acceptable salt thereof according to claim 1, wherein, in the above formula (1), m is 1.

5. The thiobenzimidazole compound or medically acceptable salt thereof according to claim 1, wherein, in the above formula (1), m is 2.

6. The thiobenzimidazole compound or medically acceptable salt thereof according to claim 1, wherein, in the above formula (1), m is 0, A is a substituted or non-substituted methylene group, ethylene group, (n- or i-)propylene group or (n-, i- or t-)butylene group, and J is a substituted or non-substituted indenyl group or substituted naphthyl group.

7. The thiobenzimidazole compound or medically acceptable salt thereof according to claim 1, wherein, in the above formula (1), m is 0, A is a substituted or non-substituted methylene group, ethylene group, (n- or i-)propylene group or (n-, i- or t-)butylene group, and J is a substituted or non-substituted furanyl group, thiophenyl group, pyrimidyl group, benzofuranyl group, benzimidazolyl group, quinolyl group, isoquinolyl group, quinoxalyl group, benzooxadiazolyl group, benzothiadiazolyl group, indolyl group, N-methylindolyl group, benzothiazolyl group, benzothiophenyl group or benzoisooxazolyl group.

8. The thiobenzimidazole compound or medically acceptable salt thereof according to claim 1, wherein, in the above formula (1), m is 0, A is a substituted or non-substituted phenylene group, indenylene group or naphthylene group, a substituted or non-substituted pyridylene group, furanylene group, thiophenylene group, pyrimidylene group, benzophenylene group, benzimidazolene group, quinolylene group, indolene group or benzothiazolene group, and J is a substituted or non-substituted phenyl group, indenyl group or naphthyl group, or a substituted or non-substituted furanyl group, thiophenyl group, pyrimidyl group, benzofuranyl group, benzimidazolyl group, quinolyl group, isoquinolyl group, quinoxalyl group, benzooxadiazolyl group, benzothiadiazolyl group, indolyl group, N-methylindolyl group, benzothiazolyl group, benzothiophenyl group or benzoisooxazolyl group.

9. The thiobenzimidazole compound or medically acceptable salt thereof according to claim 1, wherein, in the above formula (1), G is —$CH_2$—, —$CH_2CH_2$—, —$CH_2CO$—, —$CH_2CH_2O$—, —$CH_2CONH$—, —CO—, —$SO_2$—, —$CH_2SO_2$—, —$CH_2S$— or —$CH_2S$—.

10. The thiobenzimidazole compound or medically acceptable salt thereof according to claim 1, wherein, in the above formula (1), $R^1$ and $R^2$ are simultaneously a hydrogen atom, halogen atom, methyl group, ethyl group, (n- or i-)propyl group, (n-, i-, s- or t-) butyl group, methoxy group, ethoxy group, (n- or i-)propyloxy group or (n-, i-, s- or t-)butyloxy group, or $R^1$ and $R^2$ are respectively and independently a hydrogen atom, halogen atom, methyl group, ethyl group, (n- or i-)propyl group, (n-, i-, s- or t-)butyl group, methoxy group, ethoxy group, (n- or i-)propyloxy group, (n-, i-, s-, or t-)butyloxy group, trifluoromethyl group, cyano group or hydroxyl group.

11. The thiobenzimidazole compound or medically acceptable salt thereof according to claim 1, wherein, in the above formula (1), E is COOH or a tetrazole group.

12. The thiobenzimidazole compound or medically acceptable salt thereof which is a human chymase inhibitor according to any one of claims 1 through 11 wherein, in the above formula (1), X is CH.

13. A pharmaceutical composition comprising a therapeutically effective amount of at least one thiobenzimidazole compound or medically acceptable salt thereof according to claim 1, and a pharmaceutically acceptable carrier.

* * * * *